US009828413B2

(12) United States Patent
Ge

(10) Patent No.: US 9,828,413 B2
(45) Date of Patent: Nov. 28, 2017

(54) VANCOMYCIN DERIVATIVE, AND PREPARATION METHOD AND APPLICATION THEREOF

(71) Applicant: ACESYS PHARMA INC., Nanjing (CN)

(72) Inventor: Min Ge, Nanjing (CN)

(73) Assignee: ACESYS PHARMA INC., Nanjing (CN)

(*) Notice: Subject to any disclaimer, the term of this patent is extended or adjusted under 35 U.S.C. 154(b) by 0 days.

(21) Appl. No.: 14/912,573

(22) PCT Filed: Apr. 22, 2014

(86) PCT No.: PCT/CN2014/075905
§ 371 (c)(1),
(2) Date: Feb. 17, 2016

(87) PCT Pub. No.: WO2015/024389
PCT Pub. Date: Feb. 26, 2015

(65) Prior Publication Data
US 2016/0200768 A1 Jul. 14, 2016

(30) Foreign Application Priority Data

Aug. 19, 2013 (CN) .......................... 2013 1 03615770

(51) Int. Cl.
*A61K 38/14* (2006.01)
*C07K 9/00* (2006.01)
*A61K 38/00* (2006.01)

(52) U.S. Cl.
CPC .............. *C07K 9/008* (2013.01); *A61K 38/14* (2013.01); *A61K 38/00* (2013.01)

(58) Field of Classification Search
None
See application file for complete search history.

(56) References Cited

U.S. PATENT DOCUMENTS 5,840,684 A * 11/1998 Cooper ................. C07K 9/008
514/2.4

FOREIGN PATENT DOCUMENTS

| CN | 1119649 A | 4/1996 |
| WO | 9630401 A1 | 10/1996 |
| WO | 200004044 A1 | 1/2000 |
| WO | 2002036612 A1 | 5/2002 |
| WO | 2003018608 A2 | 3/2003 |
| WO | 2009067177 A2 | 5/2009 |

OTHER PUBLICATIONS

Master's thesis of Lei Li, Nanjing university of technology, 2011.*
Patent Cooperation Treaty, International Searching Authority, Search Report and Written Opinion for PCT/CN2014/075905, 10 pages, Jul. 28, 2014.
Thompson, et al., "Reconstruction of Vancomycin by Chemical Glycosylation of the Pseudoaglycon", J Am Chem Soc 120, 11014-11015 (1998).
Thompson, et al., "Synthesis of Vancomycin from the Aglycon", J. Am. Chem. Soc., 121 (6), 1237-1244 (1999).
Adachi, et al., "Degradation and Reconstruction of Moenomycin A and Derivatives: Dissecting the Function of the Isoprenoid Chain", J Am Chem Sac 128(43), 14012-14013 (2006).

* cited by examiner

*Primary Examiner* — Fred Reynolds
(74) *Attorney, Agent, or Firm* — Viksnins Harris Padys Malen LLP

(57) ABSTRACT

The present invention provides a vancomycin derivative, and a preparation method and an application thereof. The vancomycin derivative of the present invention is obtained by introducing a glycerate moiety between a vancomycin derivative and a liposoluble modification group and has reduced liposolubility and improved water solubility, thereby reducing a side effect in the cardiovascular aspect.

12 Claims, No Drawings

VANCOMYCIN DERIVATIVE, AND PREPARATION METHOD AND APPLICATION THEREOF

RELATED APPLICATIONS

This application is a National Stage Application under 35 U.S.C. §371 of International Application Number PCT/CN2014/075905, filed on Apr. 22, 2014, which claims priority to Chinese Application Number 2013103615770, filed on Aug. 19, 2013.

FIELD OF THE INVENTION

The invention relates to vancomycin derivatives and preparation processes thereof.

BACKGROUND OF THE INVENTION

After penicillin was used clinically in 1940, thousands of antibiotics have been developed, and also hundreds are commonly used in clinical practice. In 2006, among the 500 best-selling drugs in the world, there were 77 anti-infective drugs, which were the first of 19 categories of drugs. Due to wide use of antibiotics in clinical practice, drug resistance has been gradually evolved in bacteria, causing that more and more antibiotics lose their effectiveness gradually.

Vancomycin is a glycopeptide antibiotic produced by the *Streptomyces orientalis* strain. It was approved by US FDA for clinical use in 1958, effective mainly against Gram-positive bacteria with strong antibacterial activity, and was ever deemed as the last line of defense for human being against bacterial infections. Until 1990s, i.e. after vancomycin had been used for nearly 40 years, bacteria resistant to vancomycin were found and caused panic in the medical field. Therefore, there is an urgent need for discovery and modification of antibiotics.

During modification of vancomycin in a lone time period, scientists from Eli Lilly found in WO9630401A1 that introduction of an aliphatic or aromatic chain into the polysaccharide moiety of such compounds can improve their activities greatly and even show a very good inhibitory effect against drug-resistant bacteria, e.g. Oritavancin as shown by the following formula:

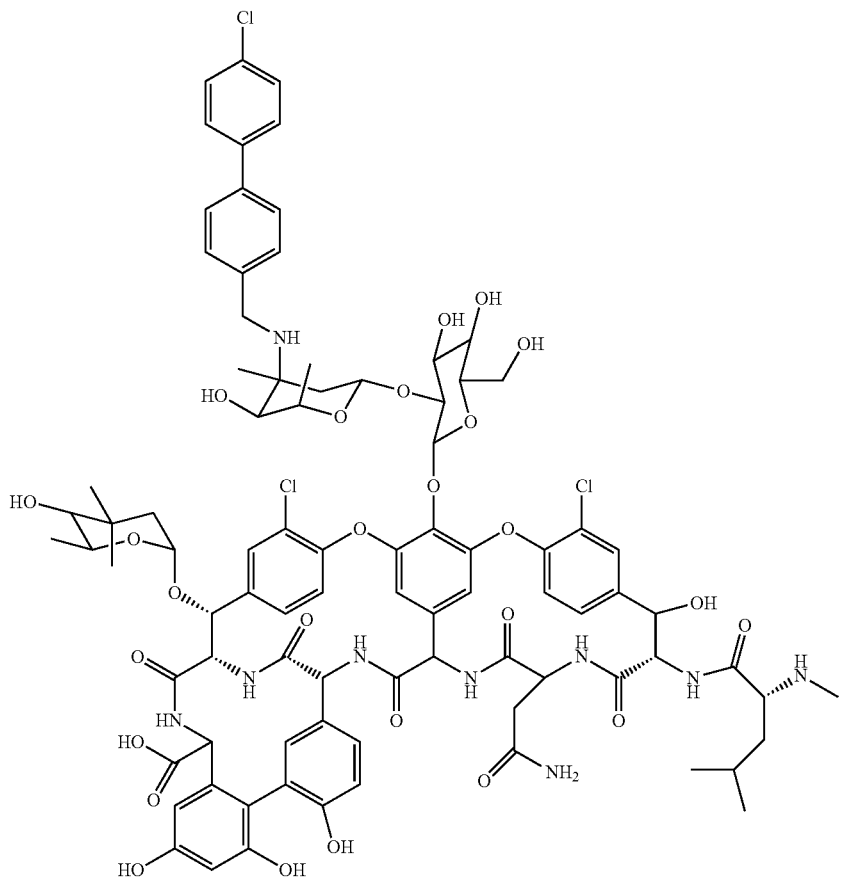

"Synthesis of Vancomycin from the Aglycon." J. Am. Chem. Soc. 1999, 121, 1237-1244 demonstrated that vancomycin derivatives modified by a long chain show dual mechanisms of action in the bacteria-killing process: in addition to the original binding mechanism of the polypeptide moiety, the polysaccharide moiety is able to inhibit the glycosyl transferase involved in the process of synthesizing cell wall. These two mechanisms are complementary each other so as to reach the objective of enhancing the activity significantly.

However, with introduction of the aliphatic and aromatic chains, the liposolubility (Log P) of such novel compounds increases greatly, and thus binding to ion channels as well as toxic and side effects on the cardiovascular system also increase, which may be adverse to the cardiovascular system.

SUMMARY OF THE INVENTION

The present invention provides vancomycin derivatives and preparation processes thereof, which derivatives have effectively increased water-solubility and reduced liposolubility, thereby solving the problem resulted from high liposolubility.

Specifically, provided is compounds having the following formula:

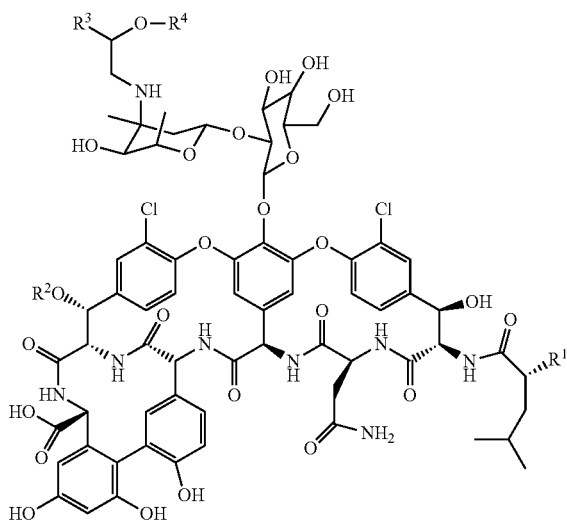

(I)

wherein:
$R^1$ is —NHCH$_3$ or —NH$_2$;
$R^2$ is H or 4-epi-vancosaminyl;
$R^3$ is —(R)COOR$^a$ or —(S)COOR$^a$ or —(R/S)COOR$^a$, and R$^a$ is H, C1-C20 alkyl, C5-C12 aryl, C2-C12 alkenyl or C2-C12 alkynyl;
$R^4$ is hydrogen, C1-C20 alkyl, C5-C12 aryl, C2-C12 alkenyl, C2-C12 alkynyl, (C1-C20 alkyl)-R$^5$ or (C1-C20 alkyl)-O—R$^5$, and R$^5$ has the structure as listed below:
(a) unsubstituted C5-C12 aryl or mono-substituted C5-C12 aryl or poly-substituted C5-C12 aryl, wherein the substituent independently is:
(I) hydroxyl
(II) halogen
(III) nitro
(IV) amino
(V) C1-C20 alkyl
(b) the following structure:

$A^1$ is —OC(A$^2$)2-C(A$^2$)2-O— or —O—C(A$^2$)2-O— or —C(A$^2$)2-O— or —C(A$^2$)2-N— or —C(A$^2$)2-C(A$^2$)2-C(A$^2$)2-C(A$^2$)2-, wherein A$^2$ independently is hydrogen or C1-C20 alkyl
(c) the following structure:

p is 1-5, wherein $R^7$ independently is the following group:
(I) hydrogen
(II) hydroxyl
(III) halogen
(IV) nitro
(V) amino
(VI) C1-C20 alkyl
(d) the following structure:

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

Provided is a vancomycin derivative as shown in formula (I):

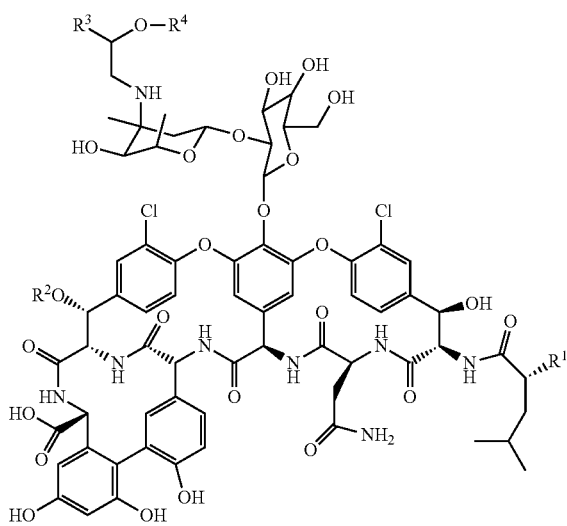

wherein:
R¹ is —NHCH₃ or —NH₂;
R² is H or 4-epi-vancosaminyl;
R³ is —(R)COOR$^a$ or —(S)COOR$^a$ or —(R/S)COOR$^a$; wherein R$^a$ is H, C1-C20 alkyl, C5-C12 aryl, C2-C12 alkenyl or C2-C12 alkynyl;
R⁴ is C1-C20 alkyl.

Provided is a vancomycin derivative as shown in formula (I):

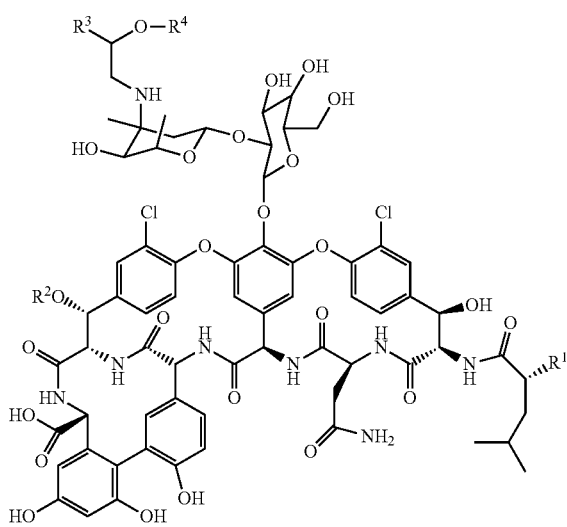

wherein:
R¹ is —NHCH₃ or —NH₂;
R² is H or 4-epi-vancosaminyl;
R³ is —(R)COOR$^a$ or —(S)COOR$^a$ or —(R/S)COOR$^a$; wherein R$^a$ is H, C1-C20 alkyl, C5-C12 aryl, C2-C12 alkenyl or C2-C12 alkynyl;
R⁴ is (C1-C20 alkyl)-R⁵, wherein R⁵ has the following structure:

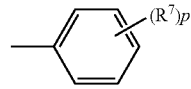

p is 1-5, wherein R⁷ independently is the following group:
(I) hydrogen
(II) hydroxyl
(III) halogen
(IV) nitro
(V) amino
(VI) C1-C20 alkyl.

Provided is a vancomycin derivative as shown in formula (I):

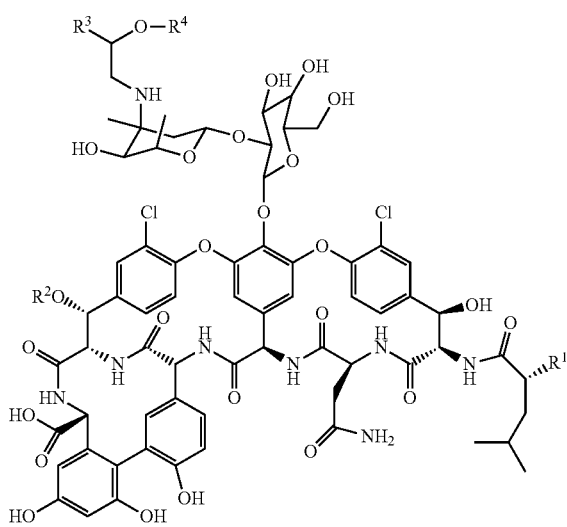

wherein:
R¹ is —NHCH₃ or —NH₂;
R² is H or 4-epi-vancosaminyl;
R³ is —(R)COOR$^a$ or —(S)COOR$^a$ or —(R/S)COOR$^a$; wherein R$^a$ is H, C1-C20 alkyl, C5-C12 aryl, C2-C12 alkenyl or C2-C12 alkynyl;
R⁴ is (C1-C20 alkyl)-R⁵, wherein R⁵ has the following structure:

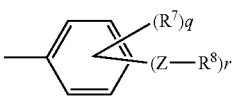

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

Provided is a vancomycin derivative as shown in formula (I):

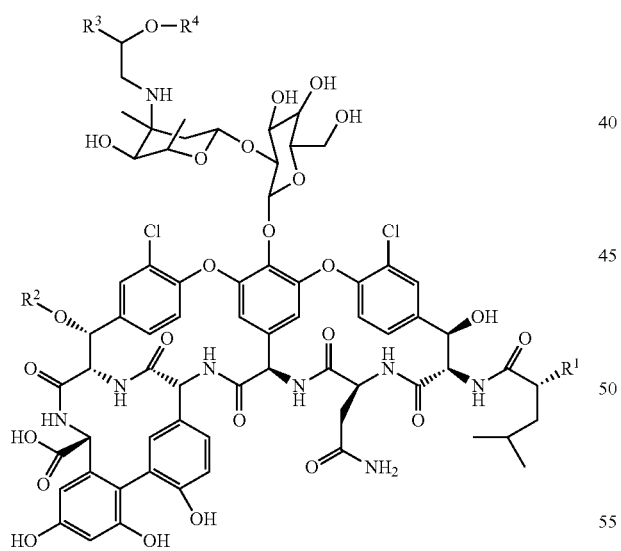

(I)

wherein:
$R^1$ is —NHCH$_3$ or —NH$_2$;
$R^2$ is H or 4-epi-vancosaminyl;
$R^3$ is —(R)COOR$^a$ or —(S)COOR$^a$ or —(R/S)COOR$^a$; wherein $R^a$ is H;
$R^4$ is (C1-C20 alkyl)-$R^5$, wherein $R^5$ has the following structure:

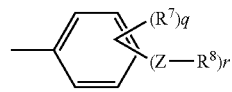

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

Provided is a medicament, which comprises the compound of formula (I) or a clinically acceptable salt thereof and is useful for treatment of infection caused by gram-positive bacteria or vancomycin-resistant bacteria.

Provided is a process for preparing vancomycin derivatives, in which
the product is obtained from reductive reaction of vancomycin or an analogue thereof and a compound of formula

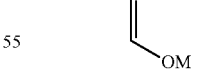

with a reductive agent in a polar solvent followed by hydrolysis, and if $R^a$ is H in the formula, the product is directly obtained after reduction without further hydrolysis;
the vancomycin and the analogue thereof are vancomycin of formula (II), norvancomycin of formula (III), 4-epi-vancosaminyl vancomycin of formula (IV) or 4-epi-vancosaminyl norvancomycin of formula (V):

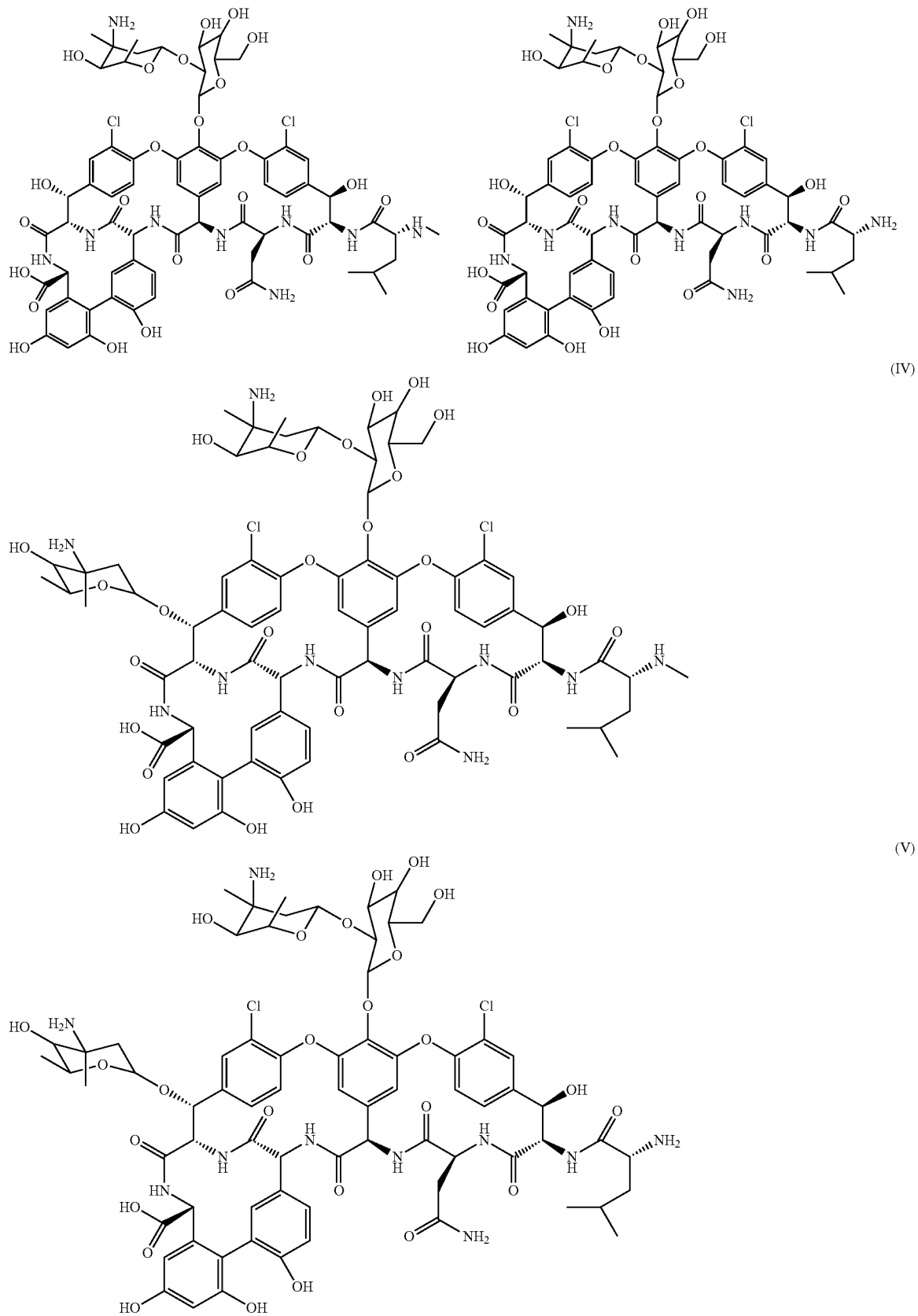

M is alkali metal or alkaline earth metal;
$R^3$ is —(R)COOR$^a$ or —(S)COOR$^a$ or —(R/S)COOR$^a$, and R$^a$ is H, C1-C20 alkyl, C5-C12 aryl, C2-C12 alkenyl, or C2-C12 alkynyl;
$R^4$ is hydrogen, C1-C20 alkyl, C5-C12 aryl, C2-C12 alkenyl, C2-C12 alkynyl, (C1-C20 alkyl)-R$^5$ or (C1-C20 alkyl)-O—R$^5$, and R$^5$ has the structure as listed below:
(a) unsubstituted C5-C12 aryl or mono-substituted C5-C12 aryl or poly-substituted C5-C12 aryl, wherein the substituent independently is:
(I) hydroxyl
(II) halogen
(III) nitro
(IV) amino
(V) C1-C20 alkyl
(b) the following structure:

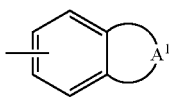

$A^1$ is —OC(A$^2$)2-C(A$^2$)2-O— or —O—C(A$^2$)2-O— or —C(A$^2$)2-O— or —C(A$^2$)2-N— or —C(A$^2$)2-C(A$^2$)2-C(A$^2$)2-C(A$^2$)2-, wherein A$^2$ independently is hydrogen or C1-C20 alkyl
(c) the following structure:

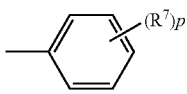

p is 1-5, wherein $R^7$ independently is the following group:
(I) hydrogen
(II) hydroxyl
(III) halogen
(IV) nitro
(V) amino
(VI) C1-C20 alkyl
(d) the following structure:

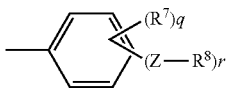

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:

(a) hydrogen
(b) hydroxyl
(c) halogen
(d) nitro
(e) amino
(f) C1-C20 alkyl.

The polar solvent is methanol, ethanol, iso-propanol, tert-butanol, N,N-dimethylformamide, N,N-dimethylacetamide; the temperature is between 0 and 80° C.; the reductive agent is sodium borohydride, potassium borohydride, borane or a complex containing borane, sodium cyano borohydride, potassium cyano borohydride, sodium triacetoxy borohydride, potassium triacetoxy borohydride; the equivalent ratio of vancomycin to the reductive agent is 1:0.8-5.0.

The present invention is described in detail as follows:
Unless otherwise stated, as used herein, halogen refers to fluorine, chlorine, bromine, iodine, represented by X.
Unless otherwise stated, as used herein, C1-C20 alkyl refers to C1-C20 hydrocarbon radical which is normal, secondary, tertiary or cyclic and contains 1, 2, 3, 4, 5, 6, 7, 8, 9, 10, 11, 12, 13, 14, 15, 16, 17, 18, 19 or 20 carbon atoms, and the examples of which include, but are not limited to, the following structures:
—CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH(CH$_3$)$_2$, —CH$_2$CH(CH$_3$)CH$_2$CH$_3$, —CH$_2$C(CH$_3$)$_3$, —CH$_2$CH$_2$CH$_2$CH$_2$CH$_2$CH$_3$, —CH(CH$_3$)CH$_2$CH$_2$CH$_2$CH$_3$, —CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$, —CH(CH$_3$)C(CH$_3$)$_3$, cyclopropyl, cyclobutyl, cyclopropylmethyl, cyclopentyl, cyclobutylmethyl, 1-cyclopropyl-1-ethyl, 2-cyclopropyl-1-yl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl and 1-cyclopropyl-2-propyl.

Unless otherwise stated, as used herein, C2-C12 alkenyl refers to C2-C12 alkene radical which is normal, secondary, tertiary or cyclic and contains 2, 3, 4, 5, 6, 7, 8, 9, 10, 11 or 12 carbon atoms, and the examples of which include, but are not limited to, —CH=CH$_2$, —CH=CHCH$_3$, —CH$_2$CH=CH$_2$, —C(=CH$_2$)(CH$_3$), —CH=CHCH$_2$CH$_3$, —CH$_2$CH=CHCH$_3$, —CH$_2$CH$_2$CH=CH$_2$, —CH=C(CH$_3$)$_2$, —CH$_2$C(=CH$_2$)(CH$_3$), —C(=CH$_2$)CH$_2$CH$_3$, —C(CH$_3$)=CHCH$_3$, —C(CH$_3$)CH=CH$_2$, —CH=CHCH$_2$CH$_2$CH$_3$, —CH$_2$CH=CHCH$_2$CH$_3$, —CH$_2$CH$_2$CH=CHCH$_3$, —CH$_2$CH$_2$CH$_2$CH=CH$_2$, —C(=CH$_2$)CH$_2$CH$_2$CH$_3$, —C(CH$_3$)=CHCH$_2$CH$_3$, —CH(CH$_3$)CH=CHCH$_3$, —CH(CH$_3$)CH$_2$CH=CH$_2$, —CH$_2$CH=C(CH$_3$)$_2$, 1-cyclopent-1-enyl, 1-cyclopent-2-enyl, 1-cyclopent-3-enyl, 1-cyclohex-1-enyl, 1-cyclohex-2-enyl and 1-cyclohexyl-3-enyl.

Unless otherwise stated, as used herein, C2-C12 alkynyl refers to C2-C12 alkyne radical which is normal, secondary, tertiary or cyclic and contains 2, 3, 4, 5, 6, 7, 8, 9, 10, 11 or 12 carbon atoms, and the examples of which include —CCH, —CCCH$_3$, —CH$_2$CCH, —CCCH$_2$CH$_3$, —CH$_2$CCCH$_3$, —CH$_2$CH$_2$CCH, —CH(CH$_3$)CCH, —CCCH$_2$CH$_2$CH$_3$, —CH$_2$CCCH$_2$CH$_3$, —CH$_2$CH$_2$CCCH$_3$ and —CH$_2$CH$_2$CH$_2$CCH.

Unless otherwise stated, as used herein, C5-C 12 aryl includes, but is not limited to, an aromatic ring containing 5, 6, 7, 8, 9, 10, 11 or 12 carbon atoms or an aromatic ring containing heteroatoms such as O, N, S and the like. The examples are:

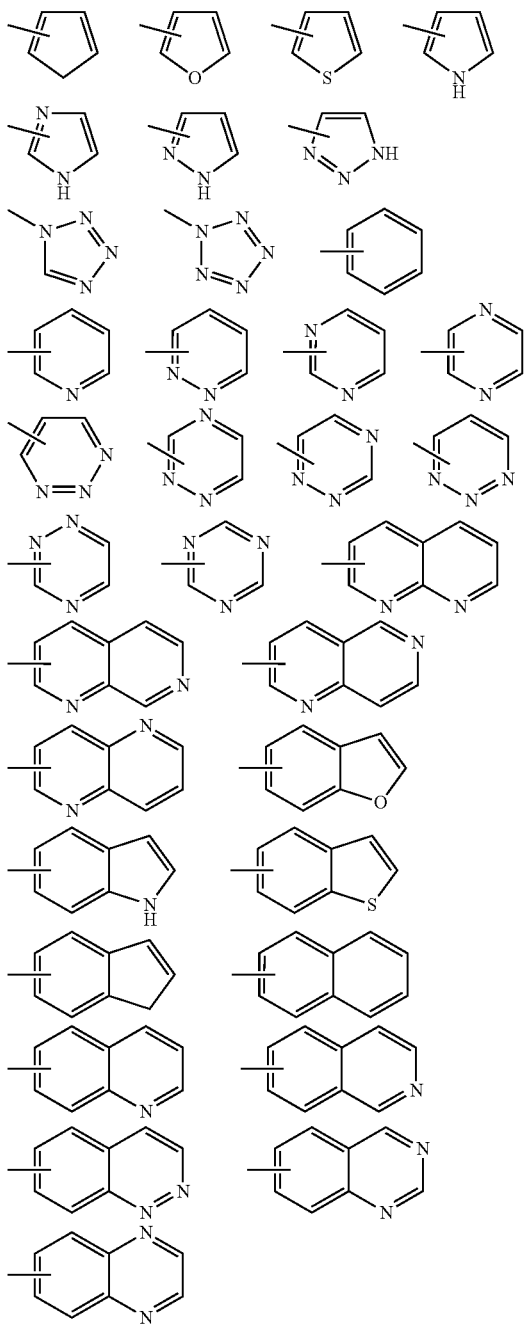

Salts include those formed with suitable anions such as the anions derived from inorganic or organic acids. Suitable acids include those which are sufficient acidic to form stable salts, preferably the acids with low toxicity. For example, the salts of the present invention can be formed by acid addition with certain inorganic or organic acids (such as HF, HCl, HBr, HI, $H_2SO_4$, $H_3PO_4$) or by addition of organic sulfonic acids or organic carboxylic acids with basic centers (typically, an amine). Organic sulfonic acids include C6-C16 aryl sulfonic acid, C6-C16 heteroaryl sulfonic acid and C1-C16 alkyl sulfonic acid such as phenyl sulfonic acid, methanesulfonic acid, ethanesulfonic acid, n-propyl sulfonic acid, isopropyl sulfonic acid, n-butyl sulfonic acid, sec-isobutyl sulfonic acid, tert-butyl sulfonic acid, pentyl sulfonic acid and hexyl sulfonic acid. Examples of organic carboxylic acids include C6-C16 aryl carboxylic acid, C4-C16 heteroaryl carboxylic acid and C1-C16 alkyl carboxylic acid such as acetic acid, glycolic acid, lactic acid, pyruvic acid, malonic acid, glutaric acid, tartaric acid, citric acid, fumaric acid, succinic acid, malic acid, maleic acid, hydroxyl maleic acid, benzoic acid, hydroxyl benzoic acid, phenylacetic acid, cinnamic acid, salicylic acid and 2-phenoxy benzoic acid. Salts also include addition salts of the compounds of the present invention with one or more amino acids. Many amino acids are suitable, especially those naturally occurring as components of proteins and however, typically those containing a basic or acidic group on the side chain (e.g. lysine, arginine or glutamic acid) or those containing a neutral group (e.g. glycine, serine, threonine, alanine, isoleucine or leucine). These salts are generally biologically compatible or pharmaceutically acceptable or non-toxic, particularly for mammals. Salts of the compounds of the present invention can be in a crystalline or amorphous form.

Unless otherwise stated, as used herein,

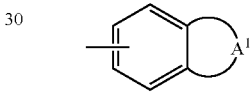

includes, but is not limited to, the following groups:

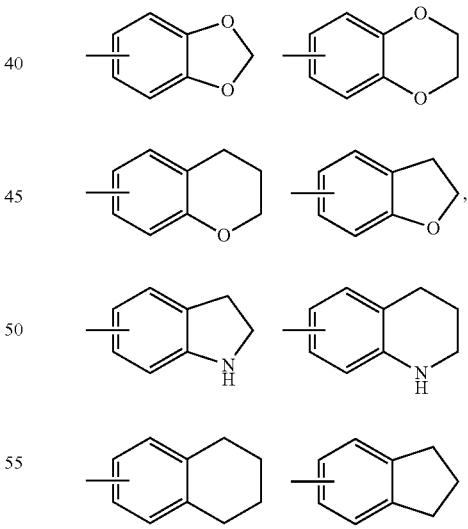

Unless otherwise stated, as used herein,

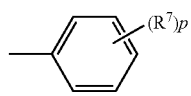

includes, but is not limited to, the following groups:
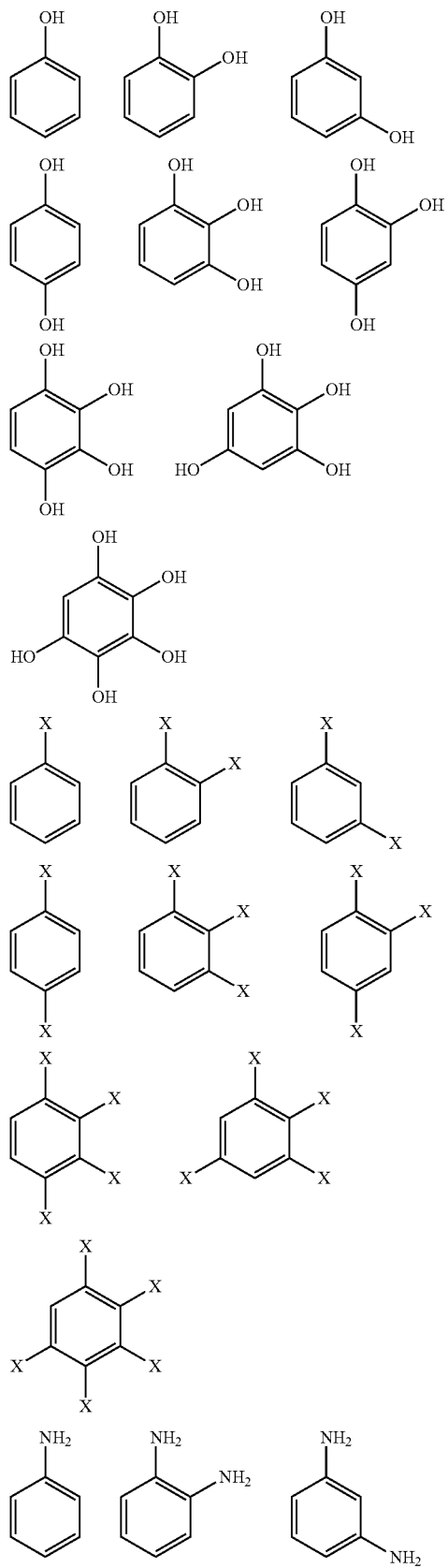
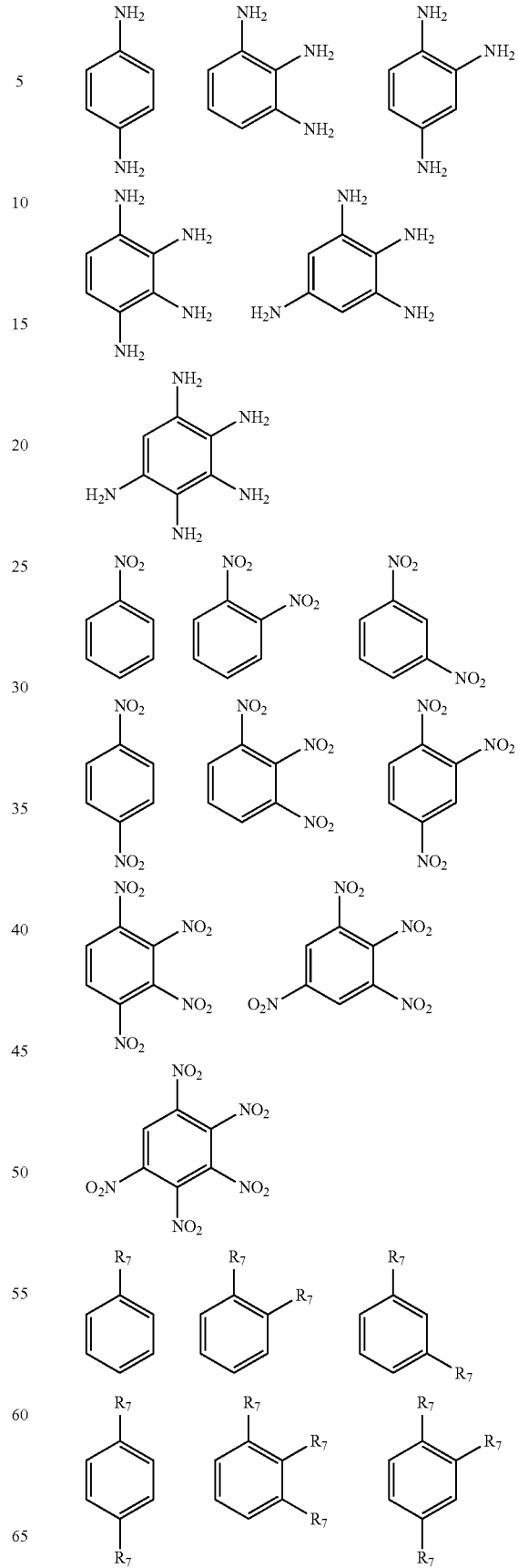

-continued

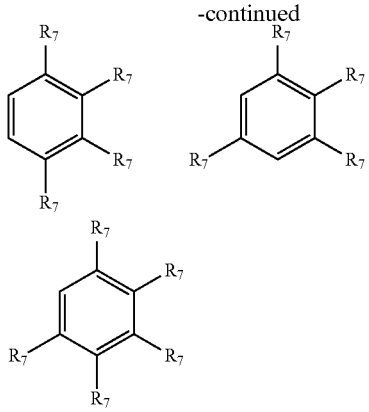

$R_7$ is $C_{1-12}$ alkyl or $C_{1-12}$ alkoxyl

Unless otherwise stated, as used herein,

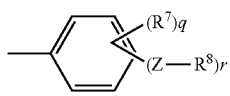

includes, but is not limited to, the following groups:

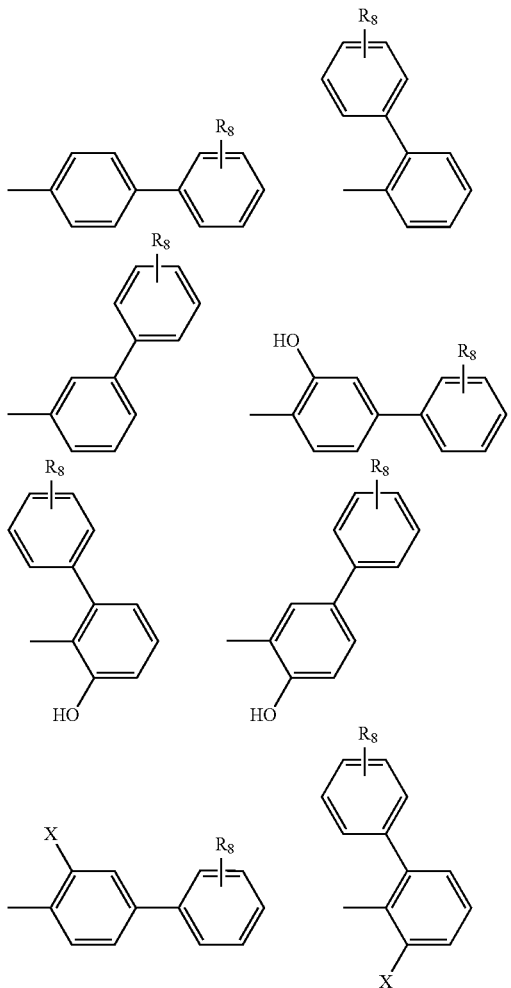

-continued

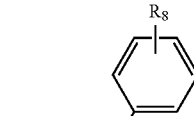

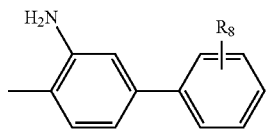

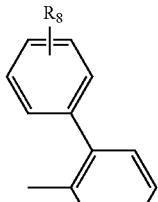

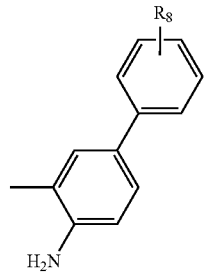

wherein $R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

Beneficial Effects:

(1) The present invention provides a group of compounds, wherein a glycerate moiety is introduced between the vancomycin derivative and the liposoluble modifying group, thereby providing the compounds with a property of high solubility in water similar to amino acids and thus effectively increasing water-solubility and reducing liposolubility of the compounds, so as to solve the problem resulted from high liposolubility and reduce the side effects on the cardiovascular system after being prepared into a medicament.

(2) The present invention provides a group of compounds, most of which exhibit varying degrees of inhibitory activity against vancomycin-sensitive bacteria, wherein aliphatic long chain and substituted biphenyl derivatives have the inhibitory activity superior to that of vancomycin, which is positive for treatment of vancomycin-resistant bacteria infection.

DETAILED DESCRIPTION OF THE INVENTION

In Vitro Activity Assay

The compound of formula 1 of the present invention or a clinically acceptable salt thereof is intended to be used for treatment of gram-positive bacteria or vancomycin-resistant bacteria infection cases.

To verify the activity, a group of the compounds of the present invention were preferably subjected to in vitro activity assay (Table 1).

TABLE 1
The compounds of formula (I)
No. Structure
V9
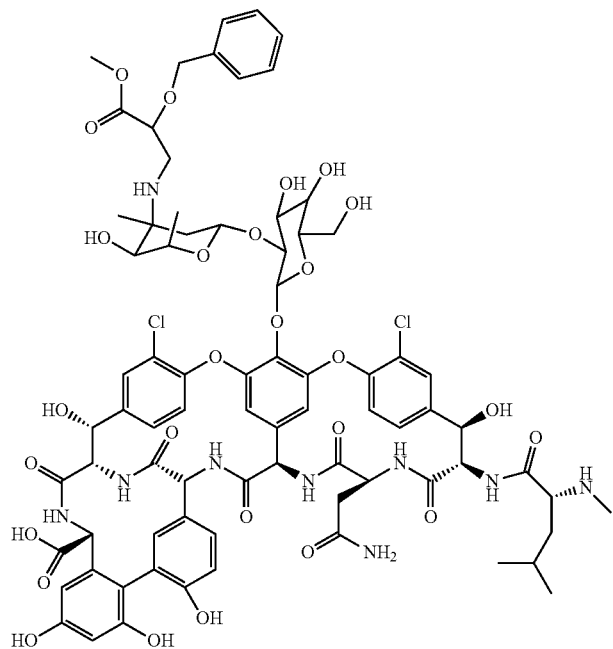
V11
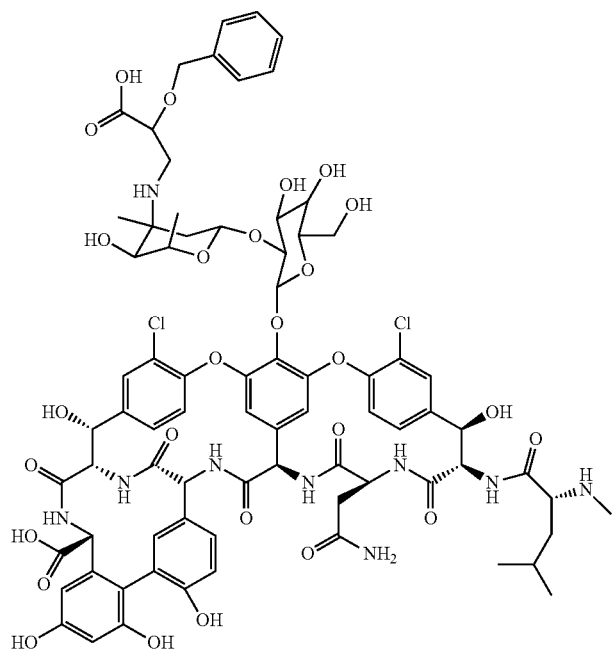

TABLE 1-continued
The compounds of formula (I)
No. Structure
V51
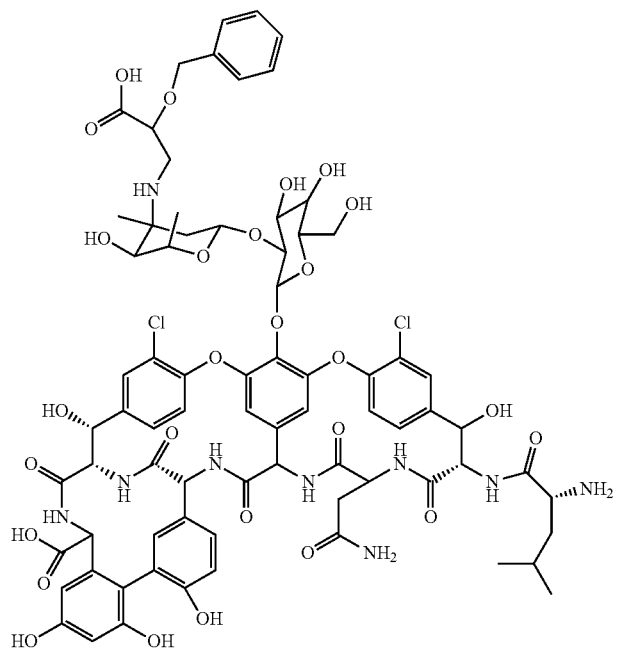
V61
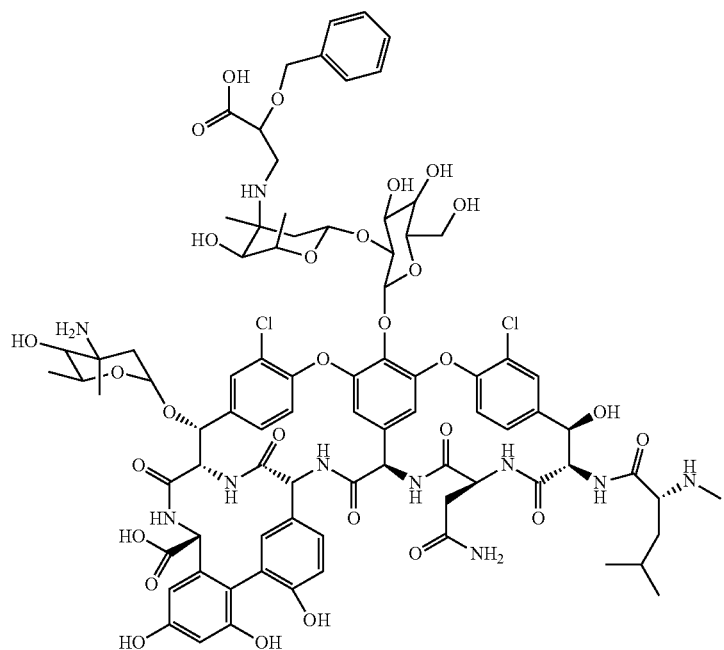

TABLE 1-continued
The compounds of formula (I)
No. Structure
V62
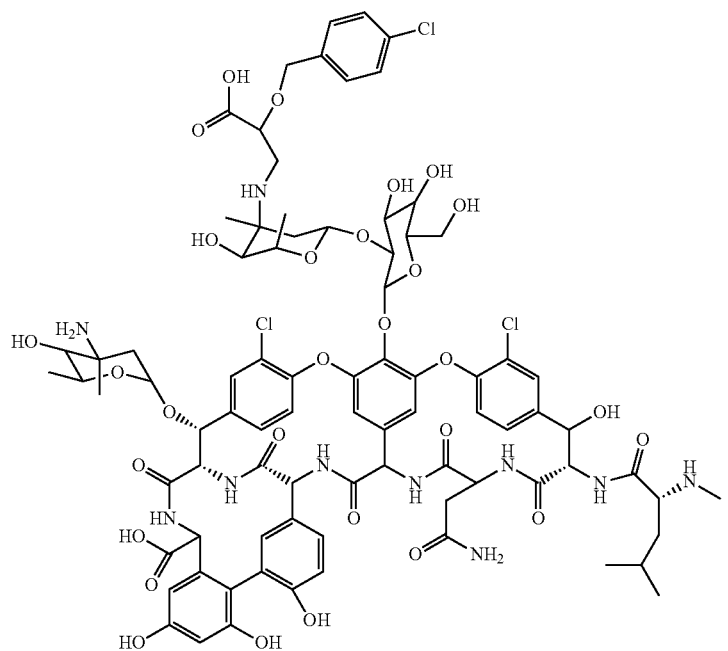
V63
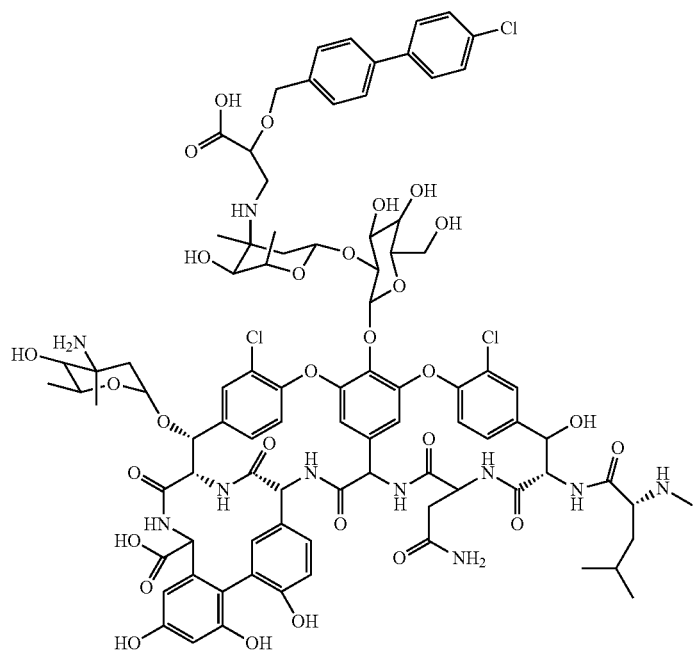

TABLE 1-continued
The compounds of formula (I)
No. Structure
V20
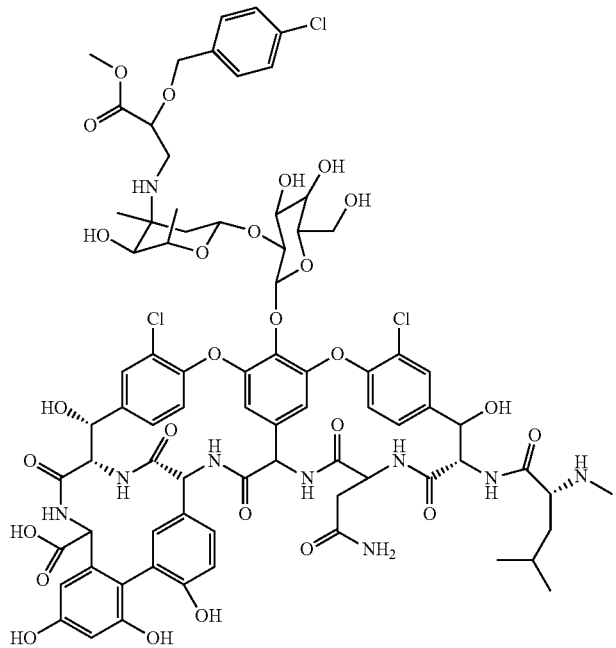
V21
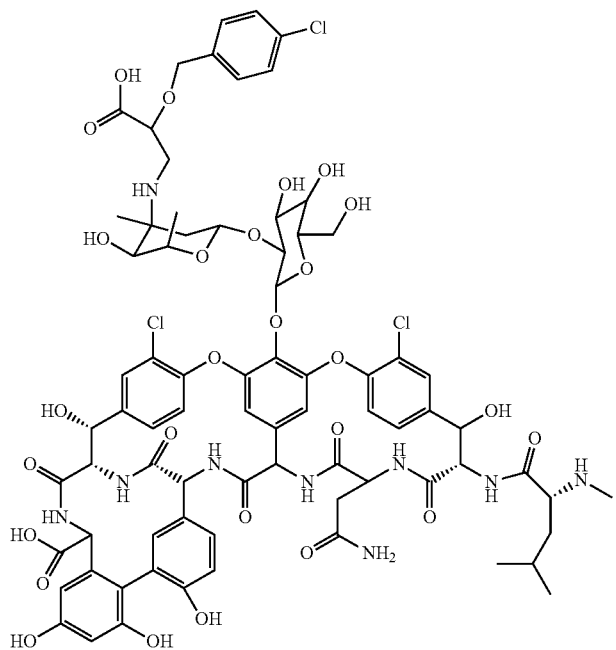

TABLE 1-continued
The compounds of formula (I)
No. Structure
V52
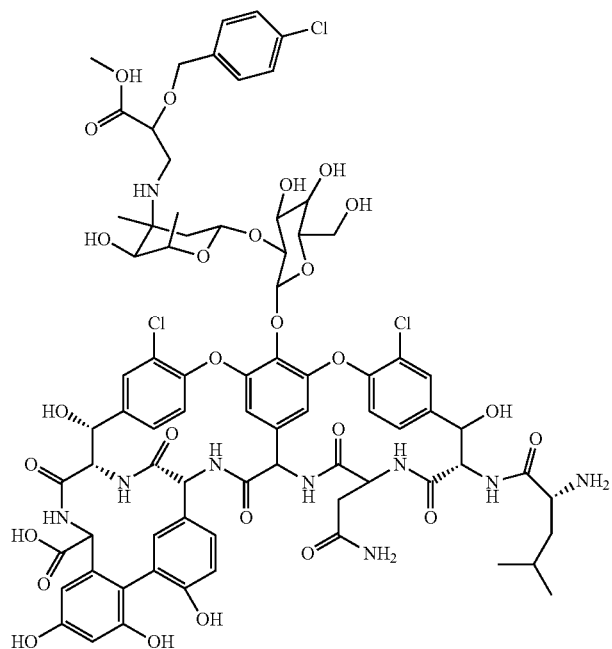
V22
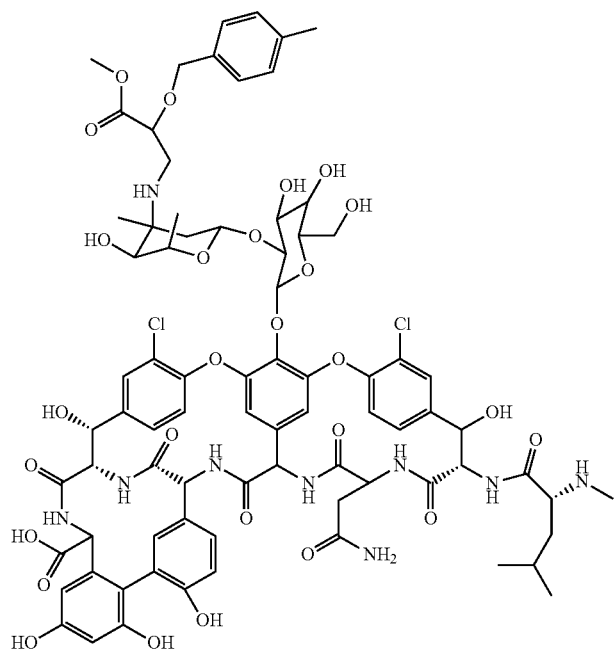

TABLE 1-continued
The compounds of formula (I)
No. Structure
V23
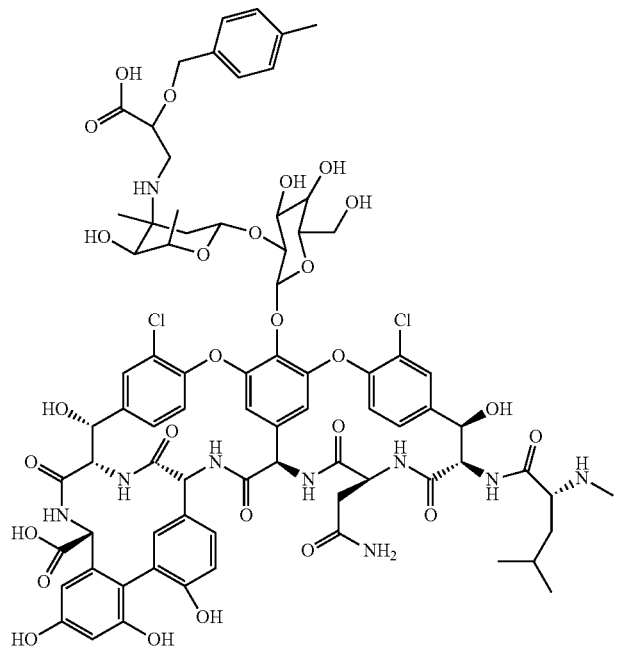
V25
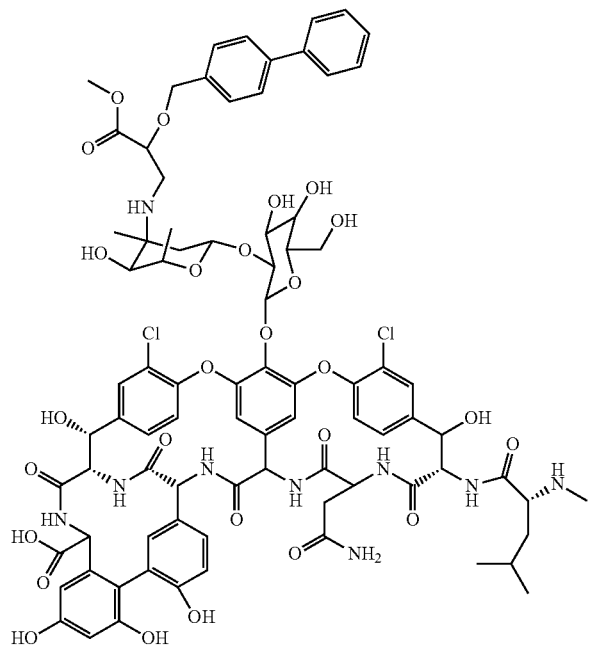

TABLE 1-continued
The compounds of formula (I)
| No. | Structure |
|---|---|
| V24 | 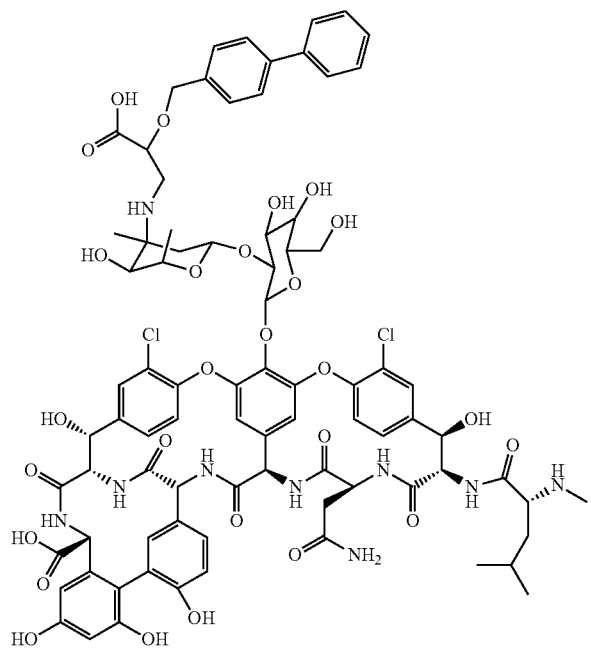 |
| V53 | 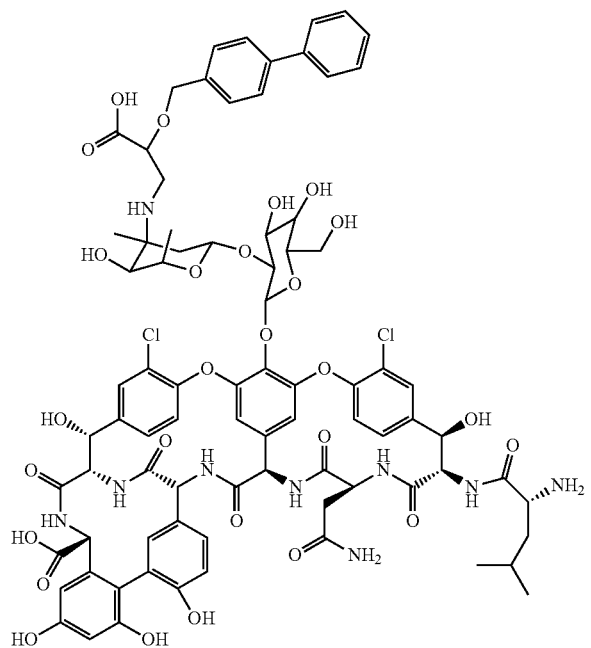 |

TABLE 1-continued
The compounds of formula (I)
No. Structure
V54
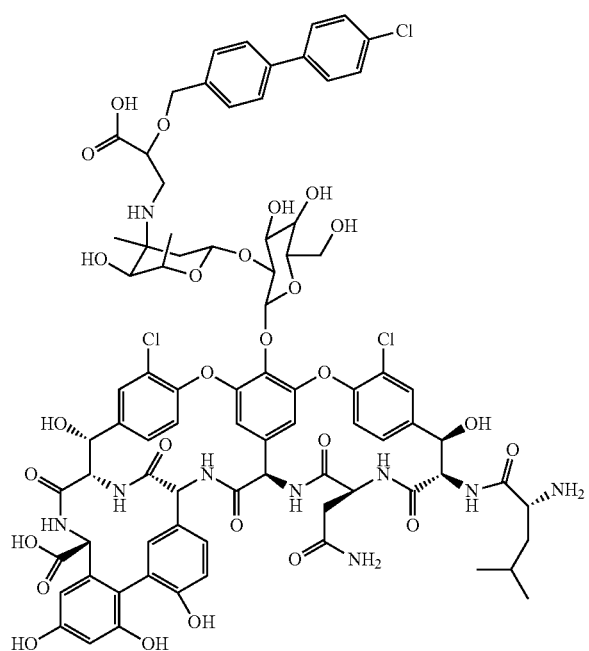
V13
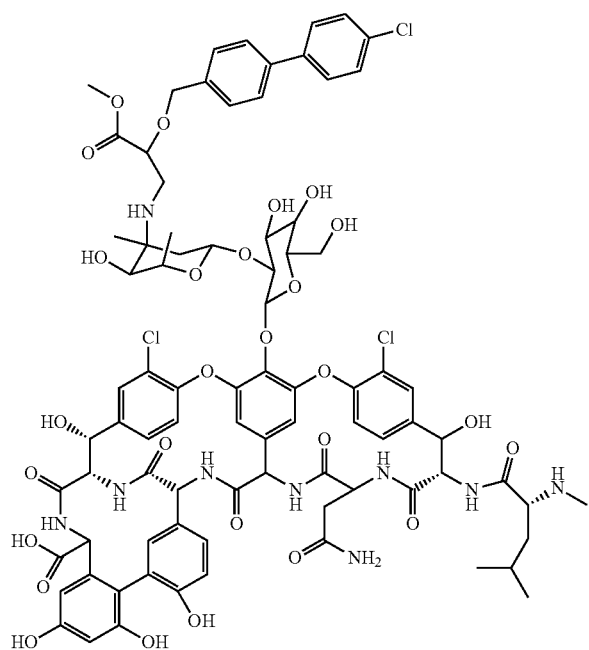

TABLE 1-continued
The compounds of formula (I)
No. Structure
V15
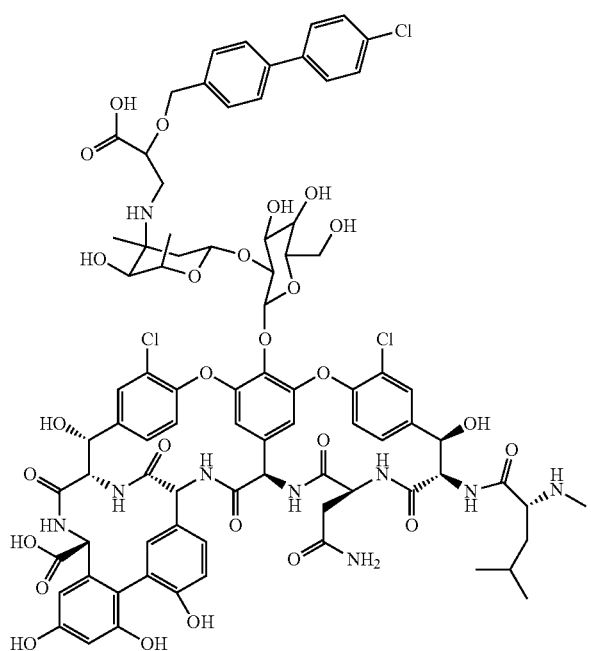
V55
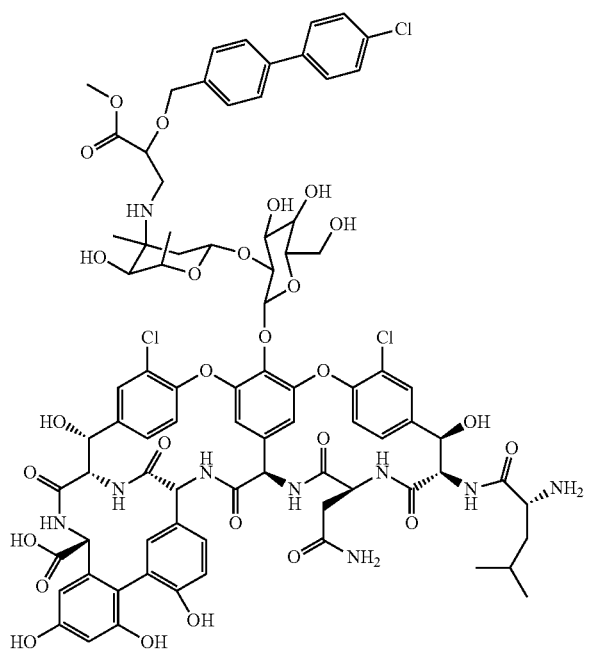

TABLE 1-continued
The compounds of formula (I)
No. Structure
V64
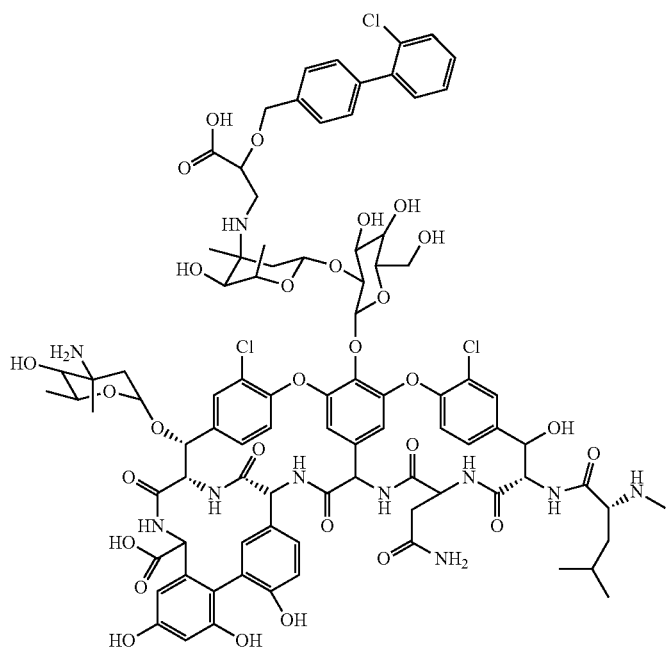
V65
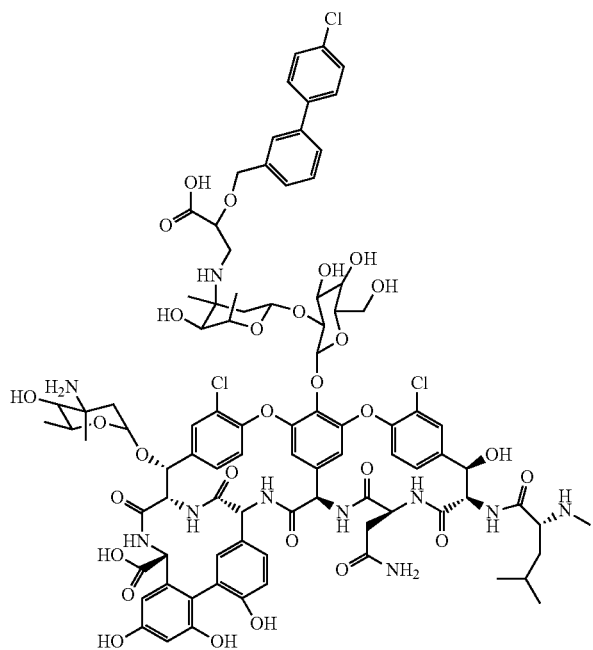

TABLE 1-continued
The compounds of formula (I)
| No. | Structure |
|---|---|
V66
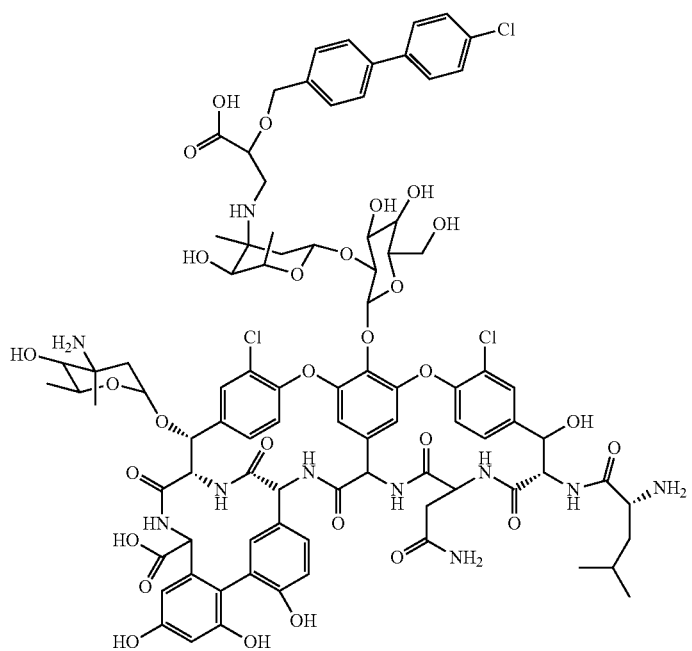
V26
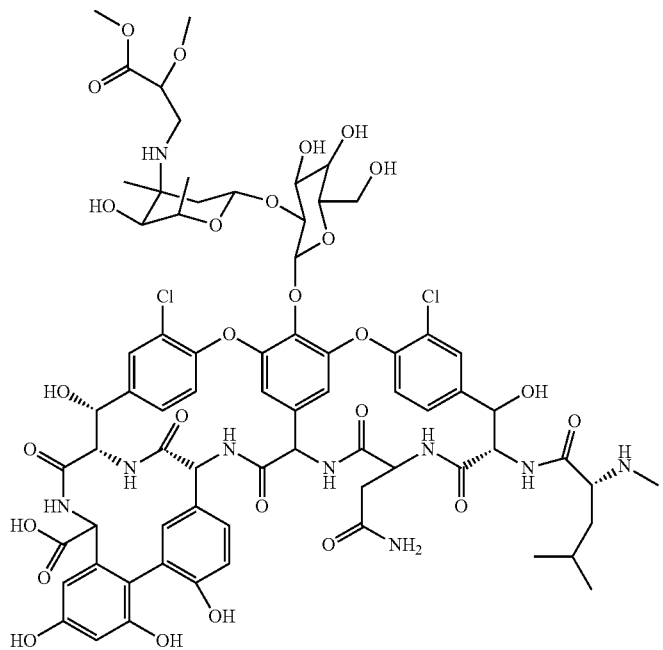

TABLE 1-continued
The compounds of formula (I)
No. Structure
V27
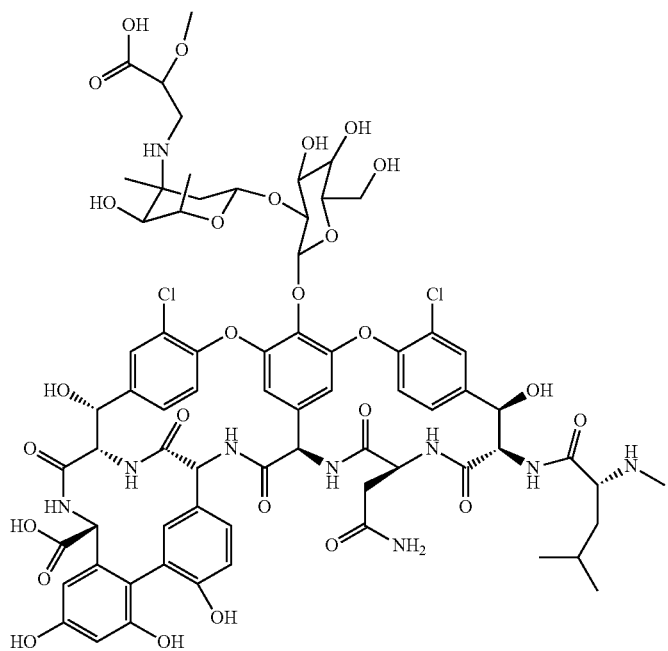
V33
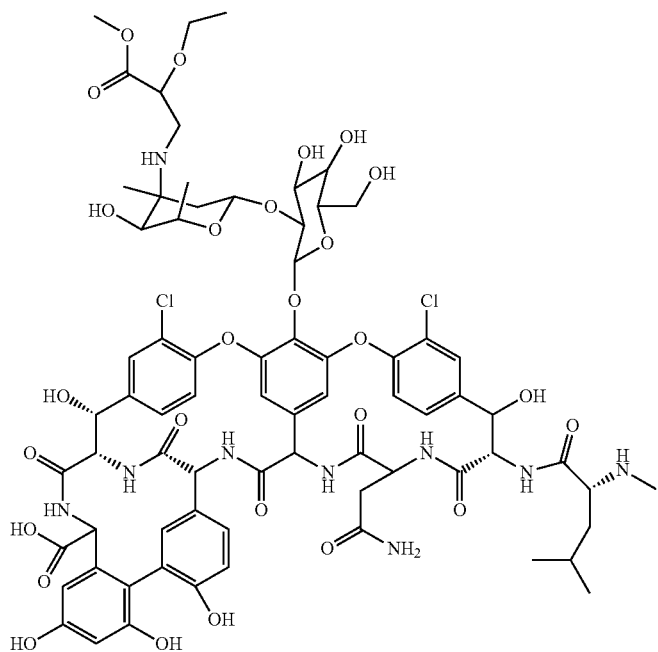

TABLE 1-continued
The compounds of formula (I)
No. Structure
V30
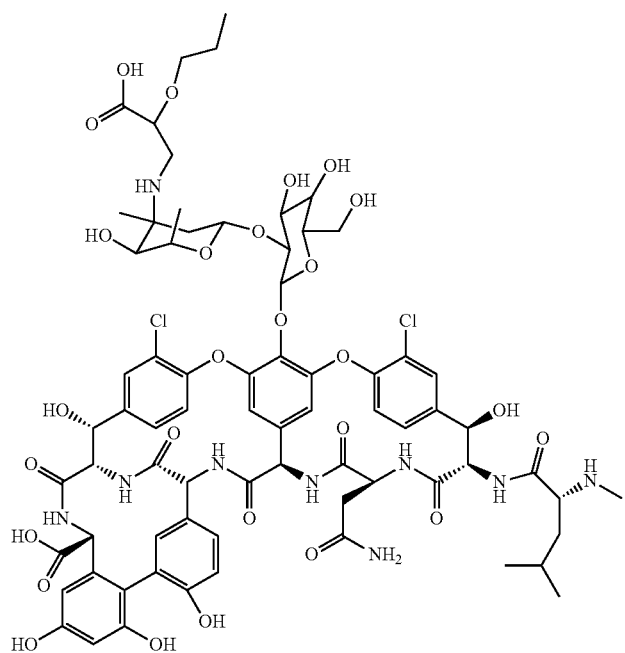
V57
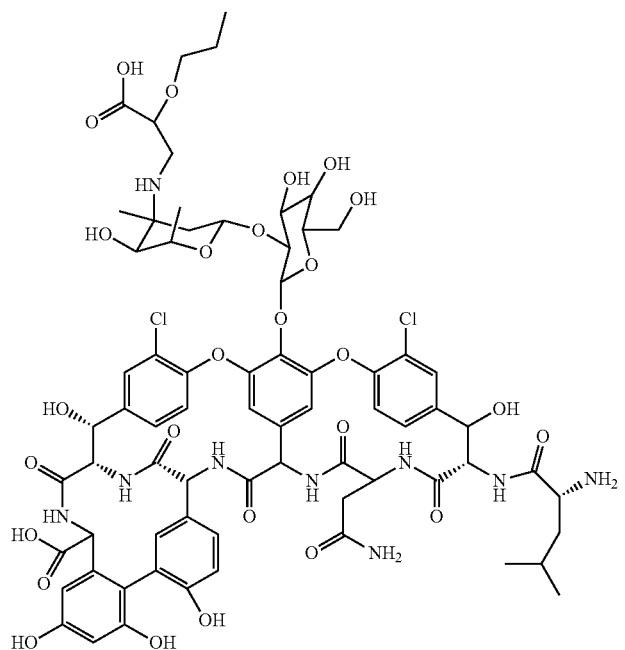

TABLE 1-continued
The compounds of formula (I)
| No. | Structure |
|---|---|
V31
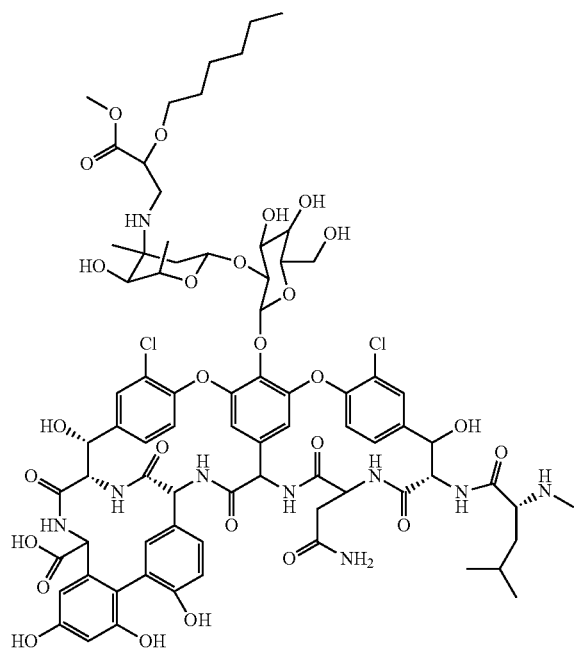
V16
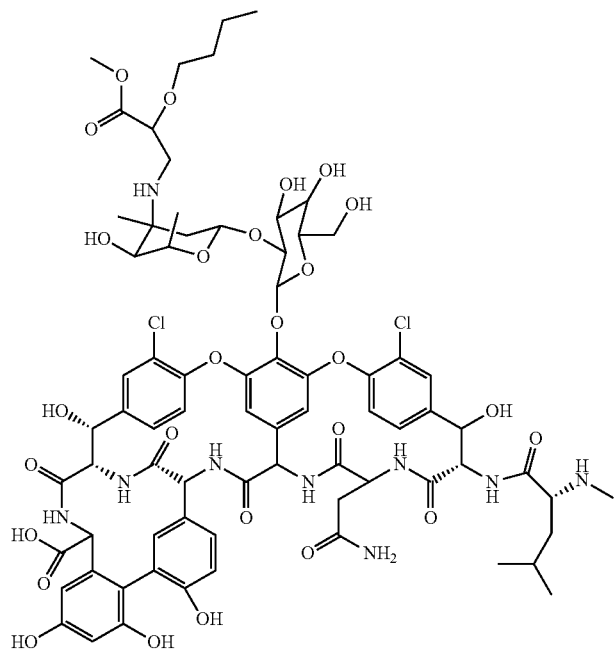

TABLE 1-continued
The compounds of formula (I)
No. Structure
V19
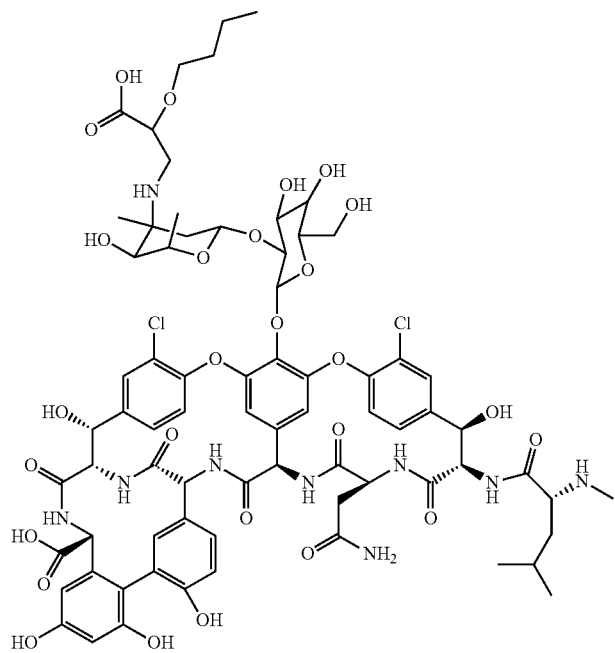
V58
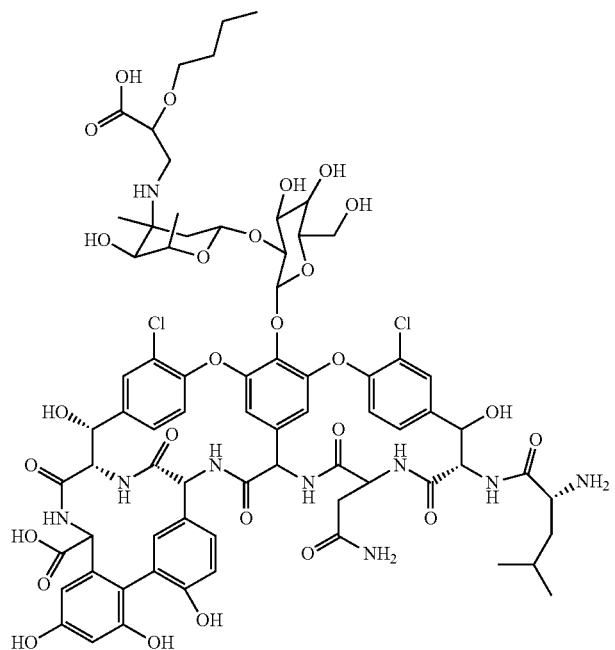

TABLE 1-continued
The compounds of formula (I)
No. Structure
V32
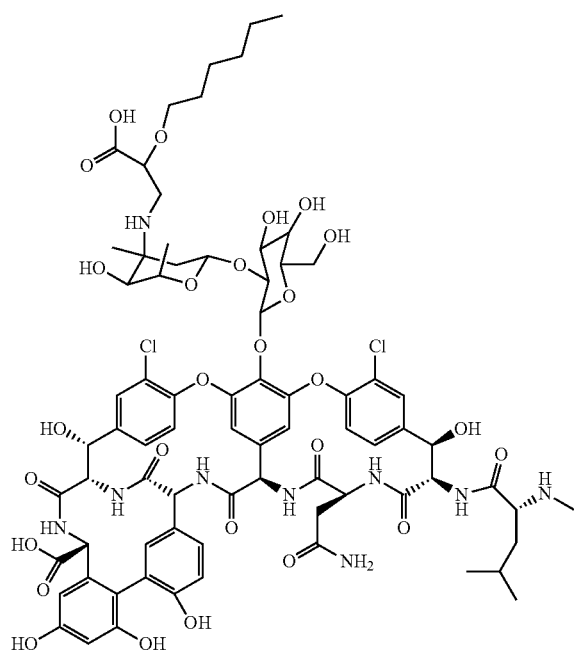
V59
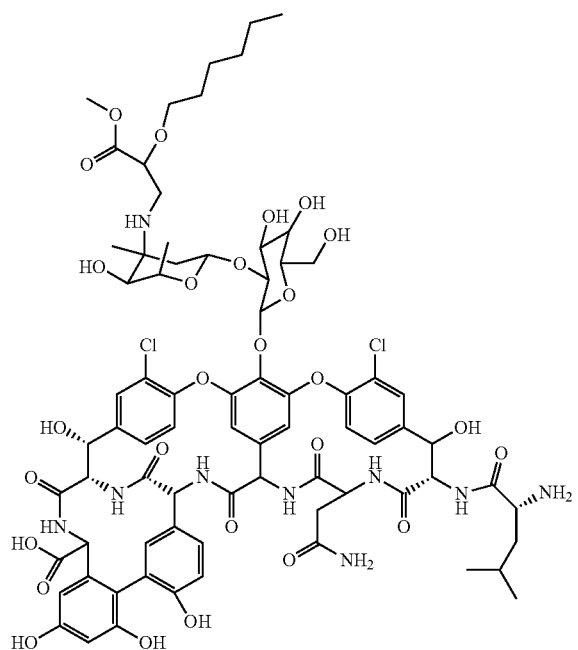

TABLE 1-continued
The compounds of formula (I)
No. Structure
V60
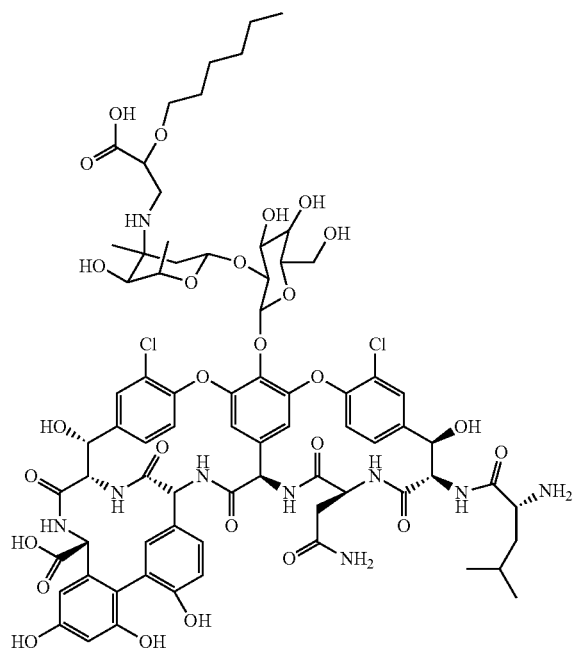
V67
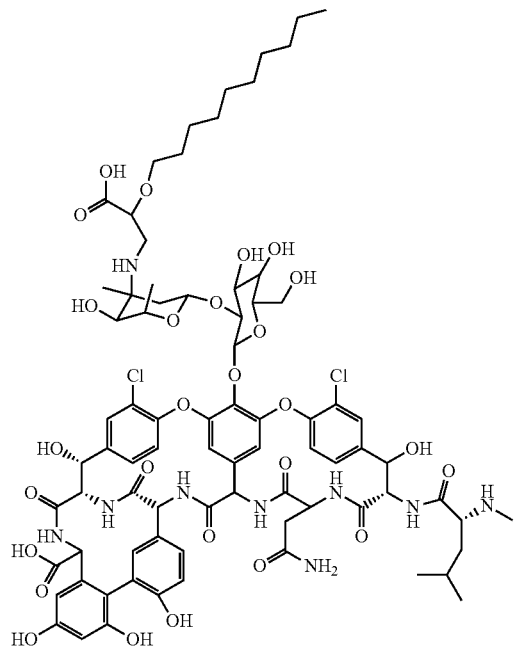

TABLE 1-continued

The compounds of formula (I)

| No. | Structure |
|---|---|
| V68 | 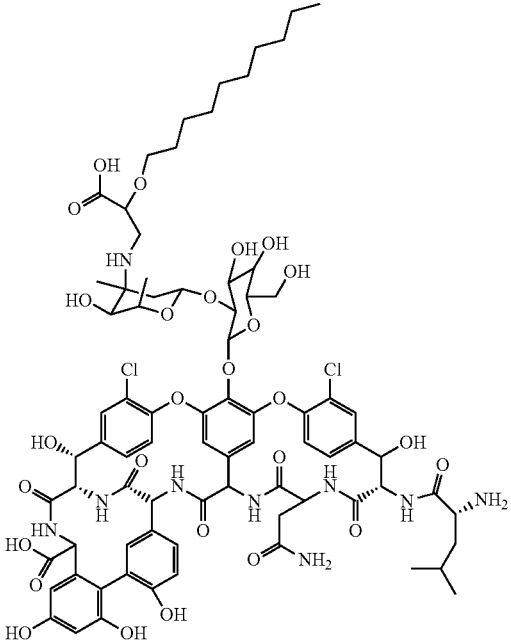 |
| V69 | 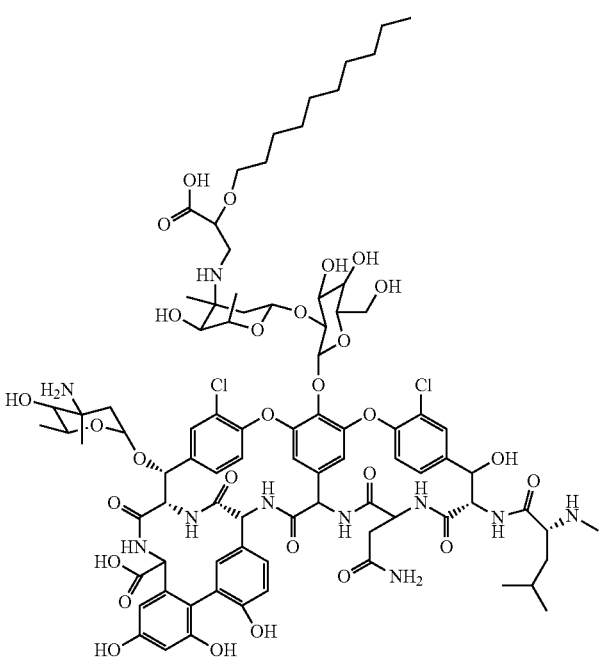 |

In vitro activity assay was performed according to Microbiological Identification of Antibiotics, Appendix XIA, Volume II, Chinese Pharmacopoeia 2010. Vancomycin-sensitive *Staphylococcus aureus* strains (Newman and Mu 50) were selected as the test strains, and trypticase soy broth was selected as the culture medium. The assay for minimum inhibitory concentration (MIC) was performed as follows: the compound to be tested was dissolved in N,N-dimethylformamide to prepare a stock solution at 1.28 mg/ml, the stock solution was diluted with the culture medium to a initial concentration of 1.28 μg/ml, which was subsequently half diluted to prepare test solutions at 64 μg/ml-0.125 μg/ml, and the assay was performed according to Cup-Plate Method, Microbiological Identification of Antibiotics, Appendix XIA, Volume II, Chinese Pharmacopoeia 2010, wherein vancomycin and blank were used as controls. The results of in vitro activity assay of the compounds of formula (I) are listed in Table 2.

TABLE 2

MIC values (μg/ml)

| | Test strains | |
|---|---|---|
| Compounds | *Staphylococcus aureus* Newman | *Staphylococcus aureus* Mu50 |
| V9 | 8 | 32 |
| V11 | 8 | 32 |
| V13 | <0.125 | 2 |
| V15 | <0.125 | 2 |
| V16 | 16 | 64 |
| V19 | 64 | >128 |
| V20 | <0.125 | 2 |
| V21 | <0.125 | 2 |
| V22 | 2 | 8 |
| V23 | 2 | 8 |
| V24 | 4 | 8 |
| V25 | 4 | 8 |
| V26 | 16 | 64 |
| V27 | 16 | 64 |
| V30 | 4 | 16 |
| V31 | 2 | 8 |
| V32 | 2 | 8 |
| V33 | 16 | 64 |
| V51 | 8 | 32 |
| V52 | <0.125 | 2 |
| V53 | <0.125 | 2 |
| V54 | <0.125 | 2 |
| V55 | <0.125 | 2 |
| V57 | 4 | 16 |
| V58 | 64 | >128 |
| V59 | 2 | 8 |
| V60 | 2 | 8 |
| V61 | 4 | 8 |
| V62 | 4 | 8 |
| V63 | <0.125 | 2 |
| V64 | <0.125 | 2 |
| V65 | <0.125 | 2 |
| V66 | <0.125 | 2 |
| V67 | 2 | 4 |
| V68 | 4 | 8 |
| V69 | 2 | 8 |
| DMSO | >128 | >128 |
| Vancomycin | 2 | 8 |

It is seen from the results that each group of the compounds exhibited varying degrees of antibacterial activity against vancomycin-sensitive *Staphylococcus aureus* strains. With increase in liposolubility of the group $R^5$, there is a trend in which the inhibitory activity of the compounds against the bacteria is enhanced.

Solubility Test of Compounds

Solubility test of each compound was performed according to the guidelines of General Notices, Volume II, Chinese Pharmacopoeia 2005: weigh out finely powdered compound, place the compound in different volumes of water, strongly shake for 30 seconds at an interval of 5 minutes; observe the solubility behavior within 30 minutes, and obtain the solubility range of the compound, wherein all the solubility data range are measured at a temperature of 25° C. Solubility of vancomycin and the analogues thereof are listed in Table 3.

TABLE 3

Solubility of the compounds in water

| Compounds | Solubility in water (mg/ml) |
|---|---|
| Vancomycin | ≥100 |
| Oritavancin | <0.1 (data from US2010/045201) |

TABLE 3-continued

Solubility of the compounds in water

| Compounds | Solubility in water (mg/ml) |
|---|---|
| V9 | <0.1 |
| V11 | 50-60 |
| V13 | 50-60 |
| V15 | ≥60 |
| V16 | ≥60 |
| V19 | 50-60 |
| V20 | <5 |
| V21 | >8 |
| V22 | <5 |
| V23 | >8 |
| V24 | >10 |
| V25 | <5 |
| V26 | 4.5 |
| V27 | 20 |
| V30 | 4 |
| V31 | <1 |
| V32 | 50-60 |
| V33 | 5 |
| V51 | 20 |
| V52 | 20 |
| V53 | 20 |
| V54 | 15-20 |
| V55 | 3 |
| V57 | >60 |
| V58 | 50-60 |
| V59 | <10 |
| V60 | >20 |
| V61 | 20 |
| V62 | 5-20 |
| V63 | 5-20 |
| V64 | 5-20 |
| V65 | 5-20 |
| V66 | 5-20 |
| V67 | 5-10 |
| V68 | 5-10 |
| V69 | 5-10 |

It is seen from the solubility data that after introducing a glycerate moiety into the structure, the solubility of the compound in water increases by 1-2 orders of magnitude as compared to Oritavancin. This result demonstrates that the glycerate moiety plays a critical role in increasing the solubility in water.

Preparation Process

Provided is a preparation process, which is a process for preparing the vancomycin derivative according to any one of claims 1-5:

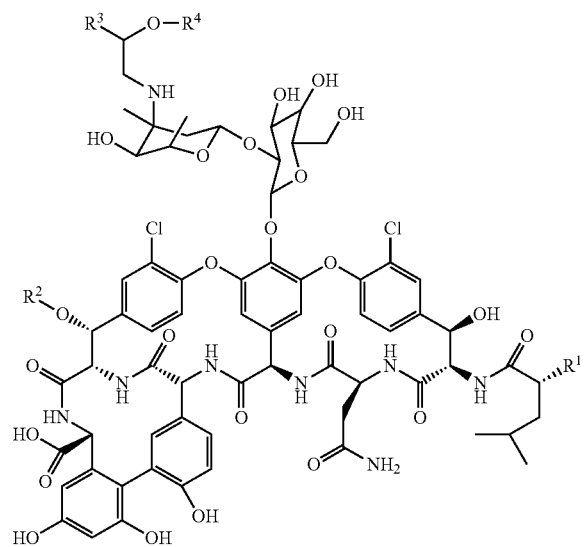
(I)
and in which the product is obtained from reductive reaction of vancomycin or an analogue thereof and a compound of formula
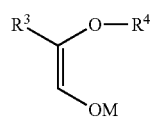
with a reductive agent in a polar solvent followed by hydrolysis, and if $R^a$ is H in the formula, the product is directly obtained after reduction without further hydrolysis;
specifically, the reaction is performed as follows:
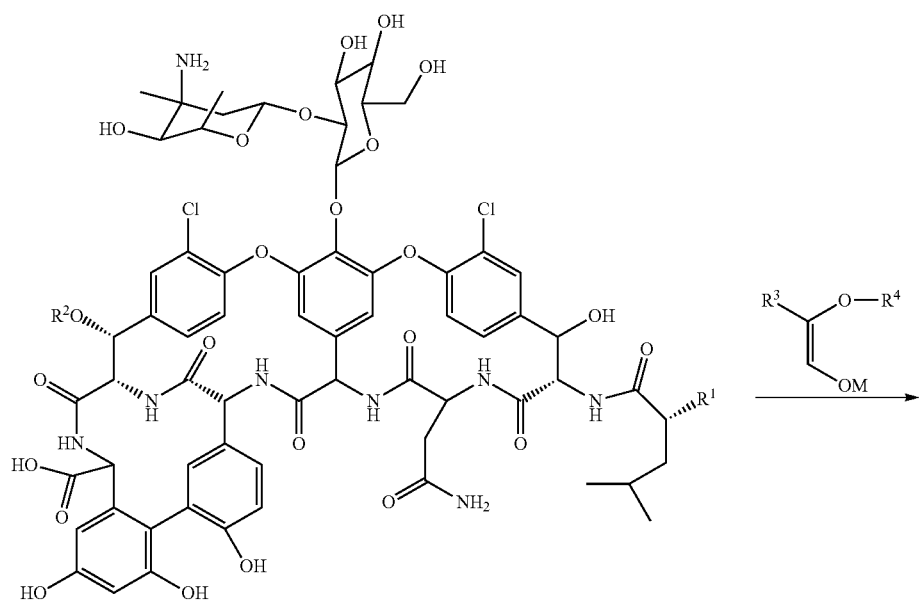

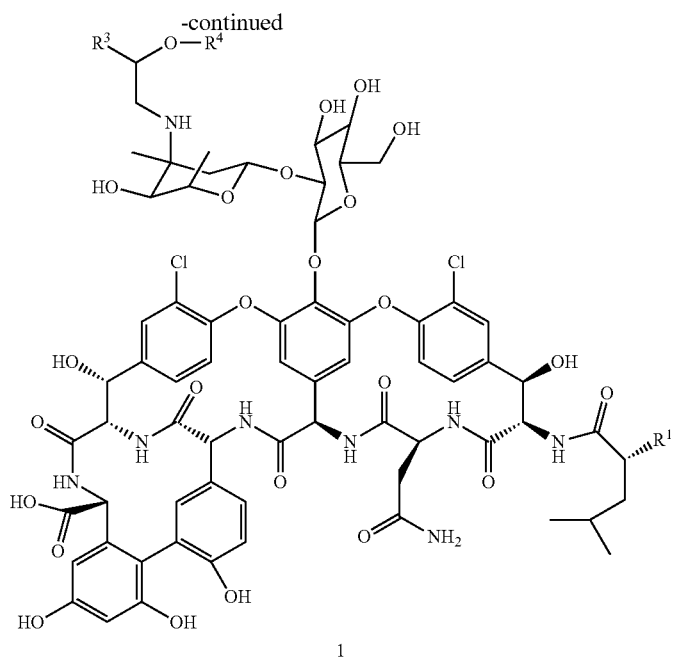
The present invention is further illustrated by the following examples, which should not be construed as limiting the present invention.
Example 1
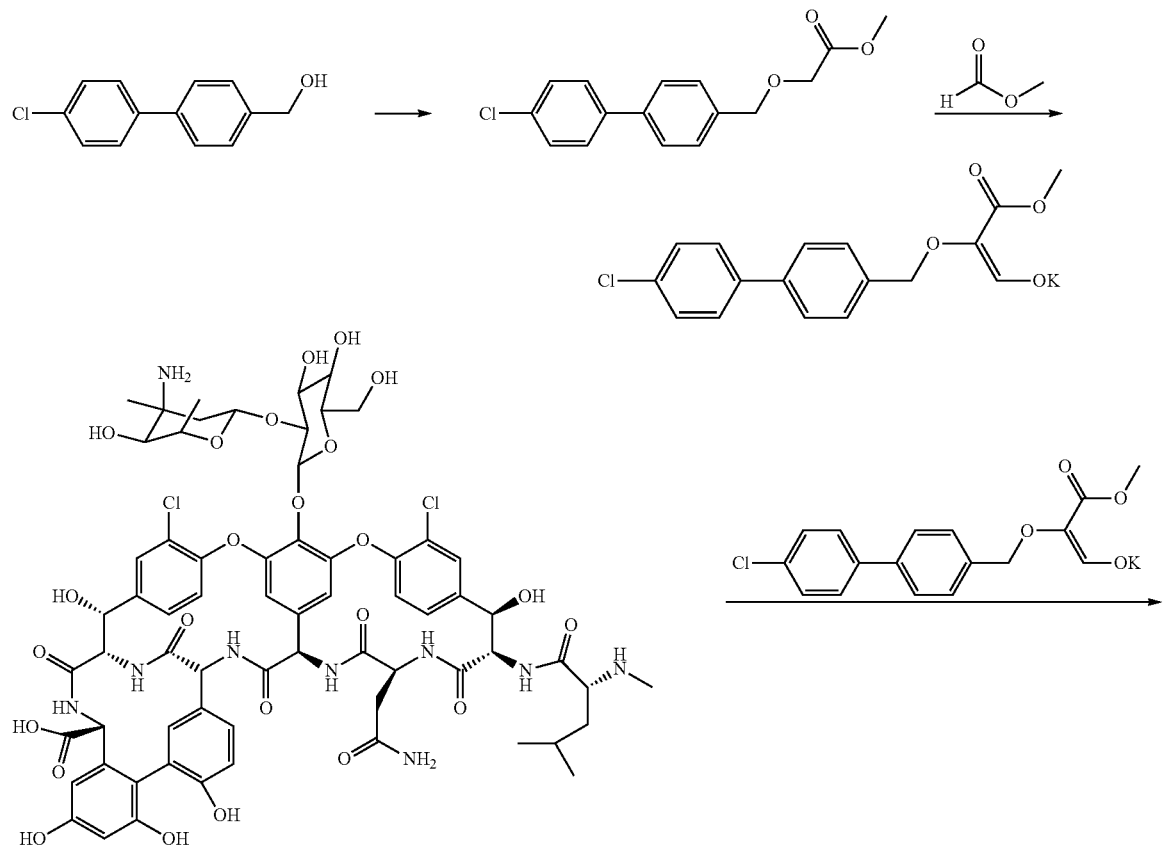

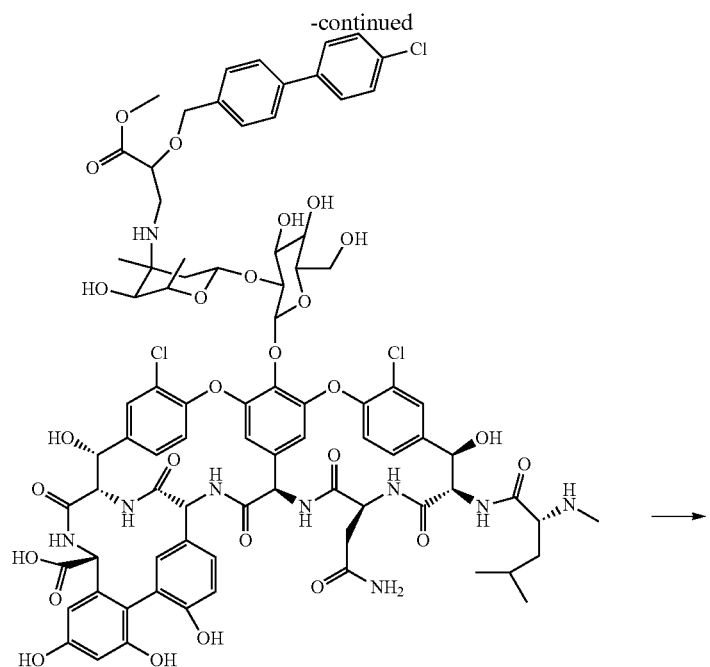
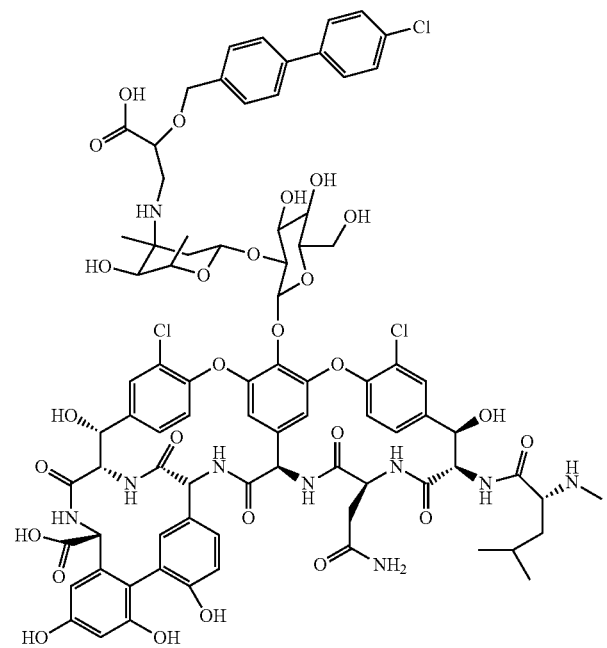
Synthetic Procedure:
Step 1:
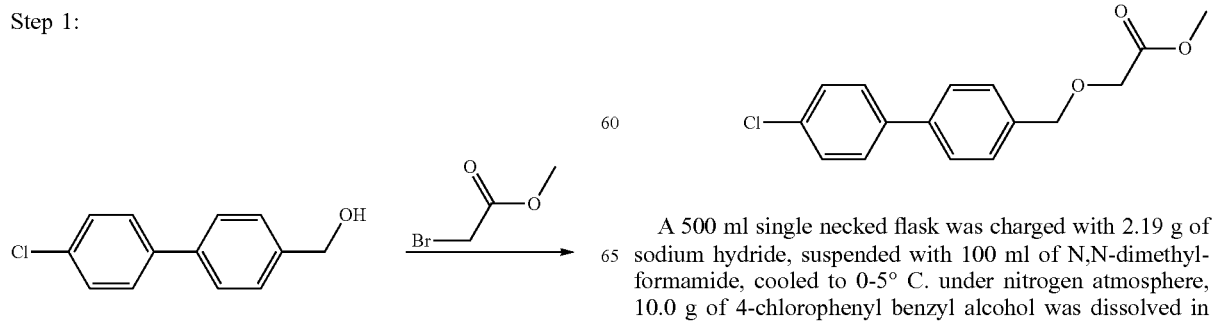
A 500 ml single necked flask was charged with 2.19 g of sodium hydride, suspended with 100 ml of N,N-dimethylformamide, cooled to 0-5° C. under nitrogen atmosphere, 10.0 g of 4-chlorophenyl benzyl alcohol was dissolved in 100 ml of N,N-dimethylformamide and was added to the reaction solution dropwise slowly, and after addition, the reaction was stirred for 0.5 hour followed by addition of 7.6 g of ethyl bromoacetate, and after addition, the temperature was raised to 35-40° C. overnight, and after the reaction completed as shown by TLC, the reaction was poured into 1 L of ice-water and was added with 500 ml of ethyl acetate for extraction, the organic phase was washed with saturated sodium chloride, dried over anhydrous sodium sulfate and then concentrated to dryness by a rotary evaporator to obtain a crude product, which was purified by column eluted with 10% ethyl acetate/petroleum ether to obtain 11.0 g of an oily liquid with a yield of 83.0%.

Step 2:

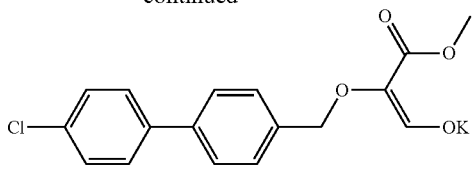

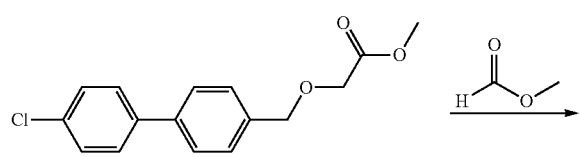

A 100 ml single necked flask was charged with 2.5 g of potassium tert-butoxide, dispersed with 15 ml of diethyl ether, a solution of 5.9 g of the product obtained from the previous step in 2.2 ml of methyl formate was added slowly under nitrogen atmosphere, the reaction solution was reacted at room temperature overnight, and after the reaction completed as shown by TLC, 50 ml of diethyl ether was added and stirred for 0.5 hour followed by suction filtration, the filter cake was dried under reduced pressure to obtain 5.6 g of a white solid.

Step 3:

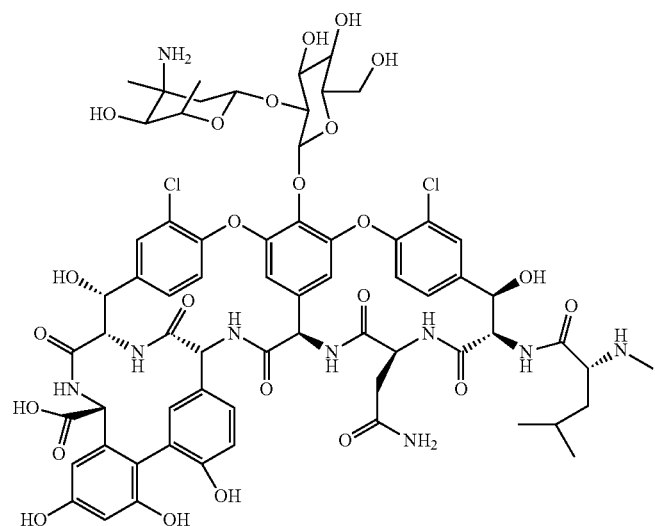

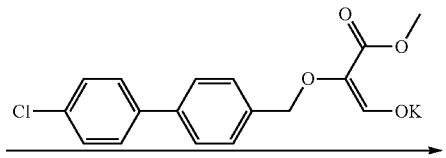

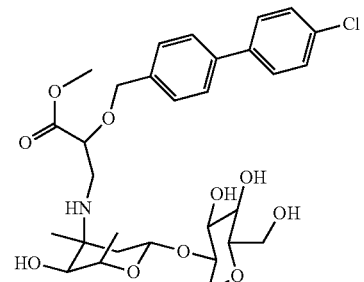

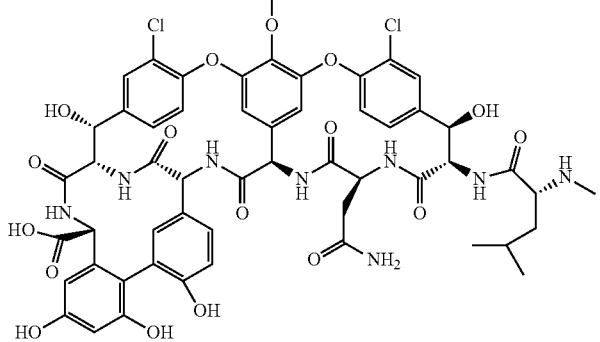

A 100 ml single necked flask was charged with 743 mg of vancomycin, which was dissolved in 40 ml of N,N-dimethylformamide at 80° C., 214 mg of the product obtained from the previous step was added, followed by addition of 63 mg of sodium cyano borohydride in batch, and after addition, the reaction was performed for 2 hours, 1 ml of acetic acid was added and stirred for 0.5 hour, the reaction solution was poured into 50 ml of diethyl ether whereupon a solid precipitated, suction filtration was performed, the filter cake was stirred/washed with 40 ml of a solvent mixture of methanol and diethyl ether (1:3) followed by suction filtration, the crude product thus obtained was isolated by preparative HPLC to obtain 100 mg of the product. MS m/e 1750.4, 1751.4, 1752.4 (M+1)

Step 4:

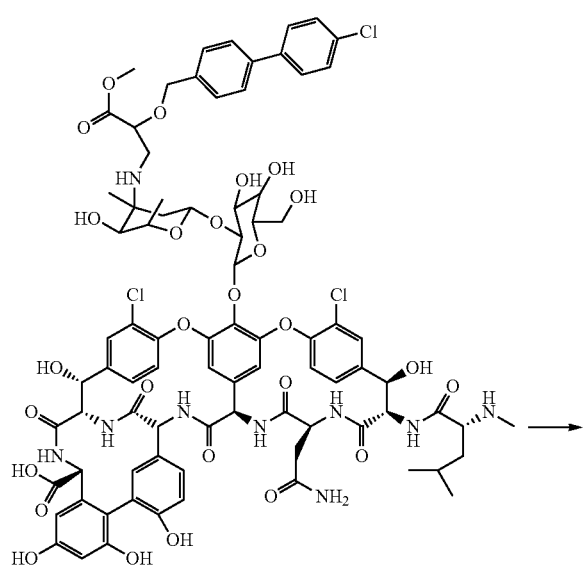

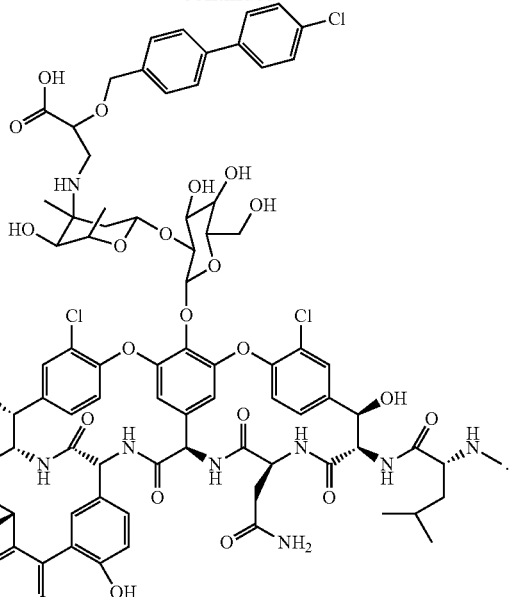

30 mg of the product obtained from the previous step was dissolved in a solvent mixture of 3 ml of tetrahydrofurane and 3 ml of water, 4.6 mg of lithium hydroxide was added with stirring, the reaction solution was stirred for 4 hours, 18 mg of acetic acid was added to quench the reaction, the organic solvent was removed by a rotary evaporator, purification by preparative HPLC obtained 9.7 mg of the product, MS m/e 1736.5, 1738.5, 1739.5 (M+1)

Example 2

Compounds V9, V11, V13, V15, V20, V21, V22, V23, V24, V25, V55, V61 and the like were prepared according to the process as described in Example 1.

Example 3

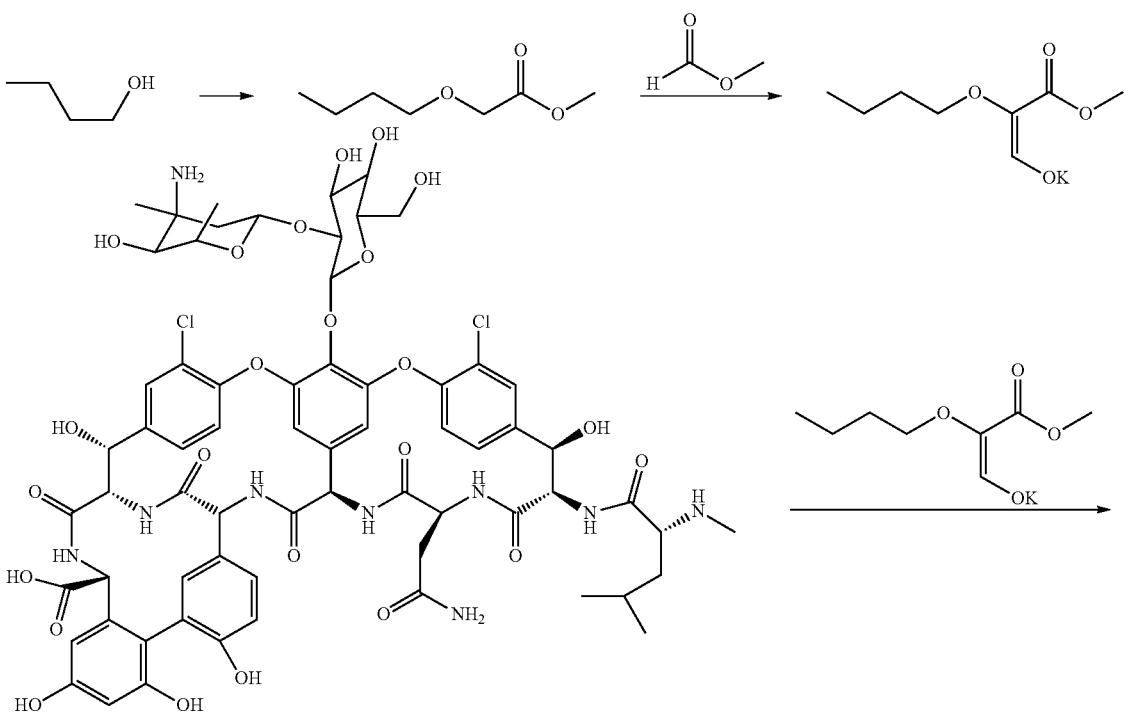

-continued

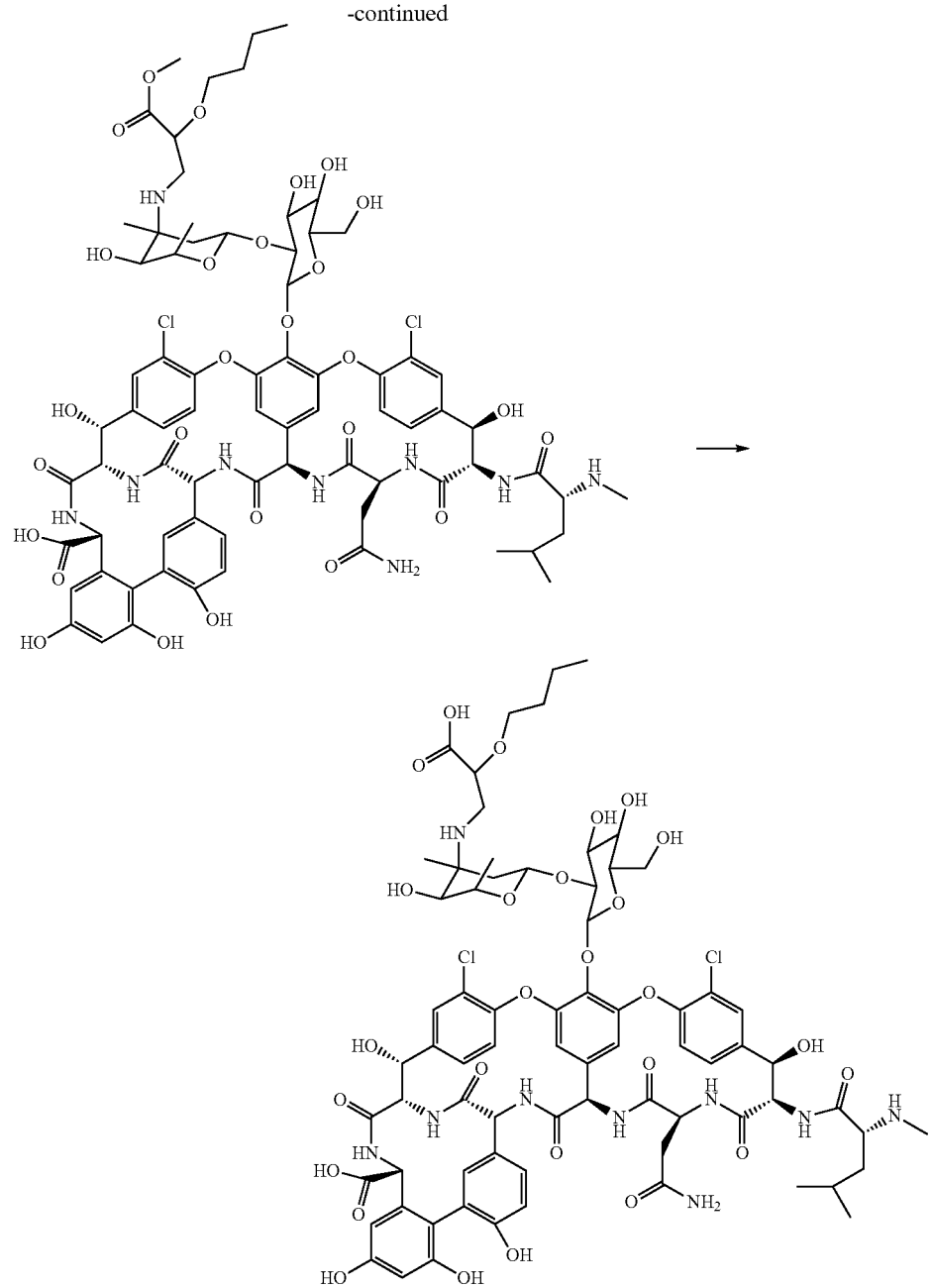

Synthetic Procedure:
Step 1:

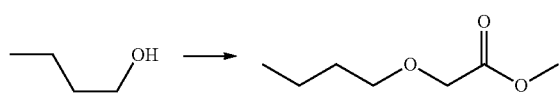

A 100 ml single necked flask was charged with 20 ml of n-butanol, 1.80 g of pieces of sodium was added in an ice-water bath, and after addition, the mixture was heated at reflux until the solid dissolved, cooled to room temperature, 10.0 g of ethyl bromoacetate was added, after which the temperature was raised to 40-50° C., stirred overnight, and after the reaction completed as shown by TLC, 100 ml of diethyl ether was added, the mixture was washed with 50 ml of water three times, the organic phase was dried by a rotary evaporator under reduced pressure to obtain 9.1 g of an oily liquid, which was directly used in the next step.

Step 2:

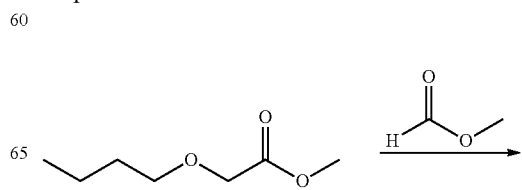

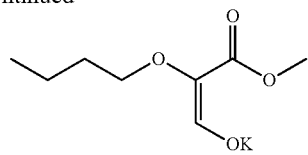

A 100 ml single necked flask was charged with 2.5 g of potassium tert-butoxide, dispersed with 15 ml of diethyl ether, a solution of 3.0 g of the product obtained from the previous step in 2.2 ml of methyl formate was added slowly under nitrogen atmosphere, the reaction solution was reacted at room temperature overnight, and after the reaction completed as shown by TLC, 50 ml of diethyl ether was added and stirred for 0.5 hour followed by suction filtration, the filter cake was dried under reduced pressure to obtain 2.9 g of a white solid.

Step 3:

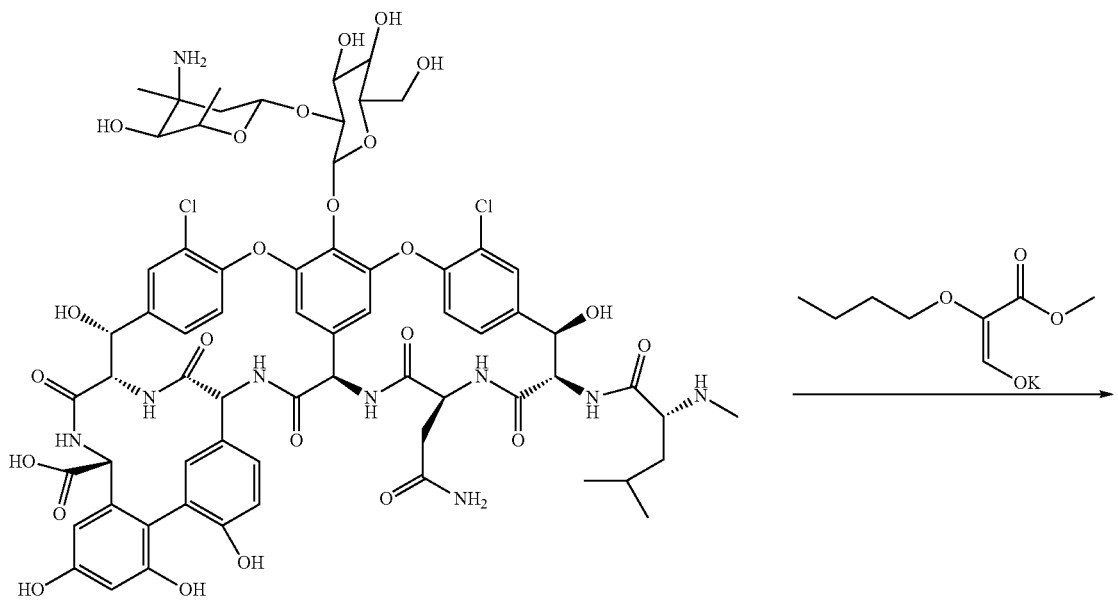

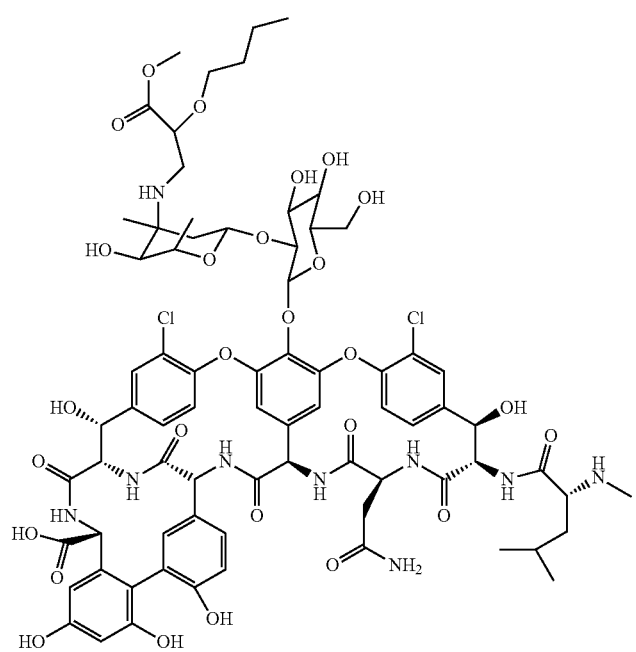

A 250 ml single necked flask was charged with 1.48 g of vancomycin, which was dissolved in 80 ml of N,N-dimethylformamide at 80° C., 276 mg of the product obtained from the previous step was added, followed by addition of 126 mg of sodium cyano borohydride in batch, and after addition, the reaction was performed for 2 hours, 5 ml of acetic acid was added and stirred for 0.5 hour, the reaction solution was poured into 100 ml of diethyl ether whereupon a solid precipitated, suction filtration was performed, the filter cake was stirred/washed with 40 ml of a solvent mixture of methanol and diethyl ether (1:3) followed by suction filtration, the crude product thus obtained was isolated by preparative HPLC to obtain 56 mg of the product. MS m/e 1606.5, 1607.5, 1608.5 (M+1)

Step 4:

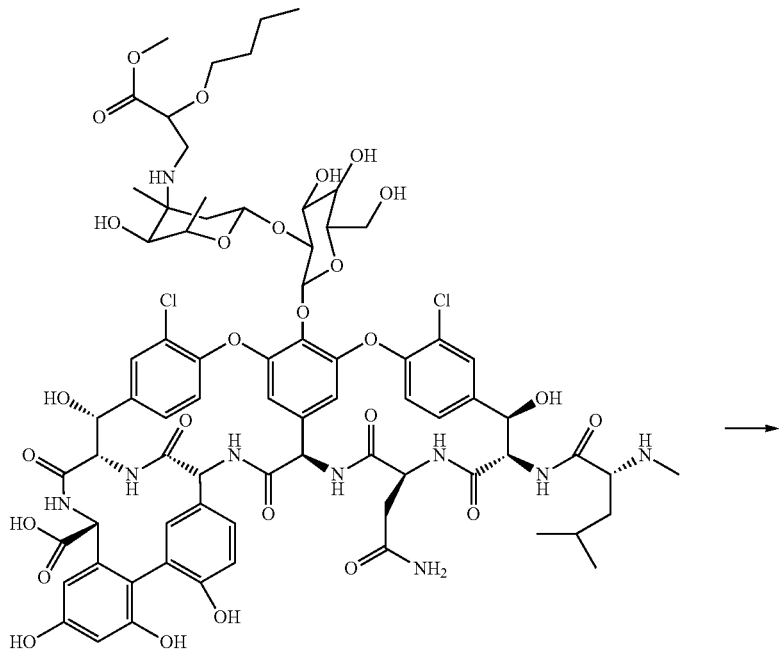

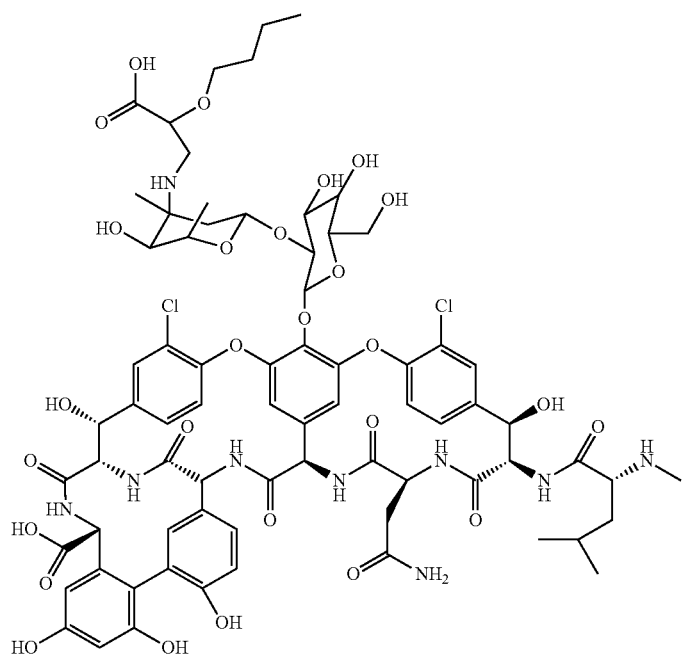

30 mg of the product obtained from the previous step was dissolved in a solvent mixture of 3 ml of tetrahydrofurane and 3 ml of water, 7.8 mg of lithium hydroxide was added with stirring, the reaction solution was stirred for 4 hours, 18 mg of acetic acid was added to quench the reaction, the organic solvent was removed by a rotary evaporator, purification by preparative HPLC obtained 5.0 mg of the product, MS m/e 1592.2, 1593.2 (M+1)

Example 4

Compounds V16, V19, V26, V27, V30, V31, V32, V33, V67, V68 and the like were prepared according to the process as described in Example 1.

Example 5

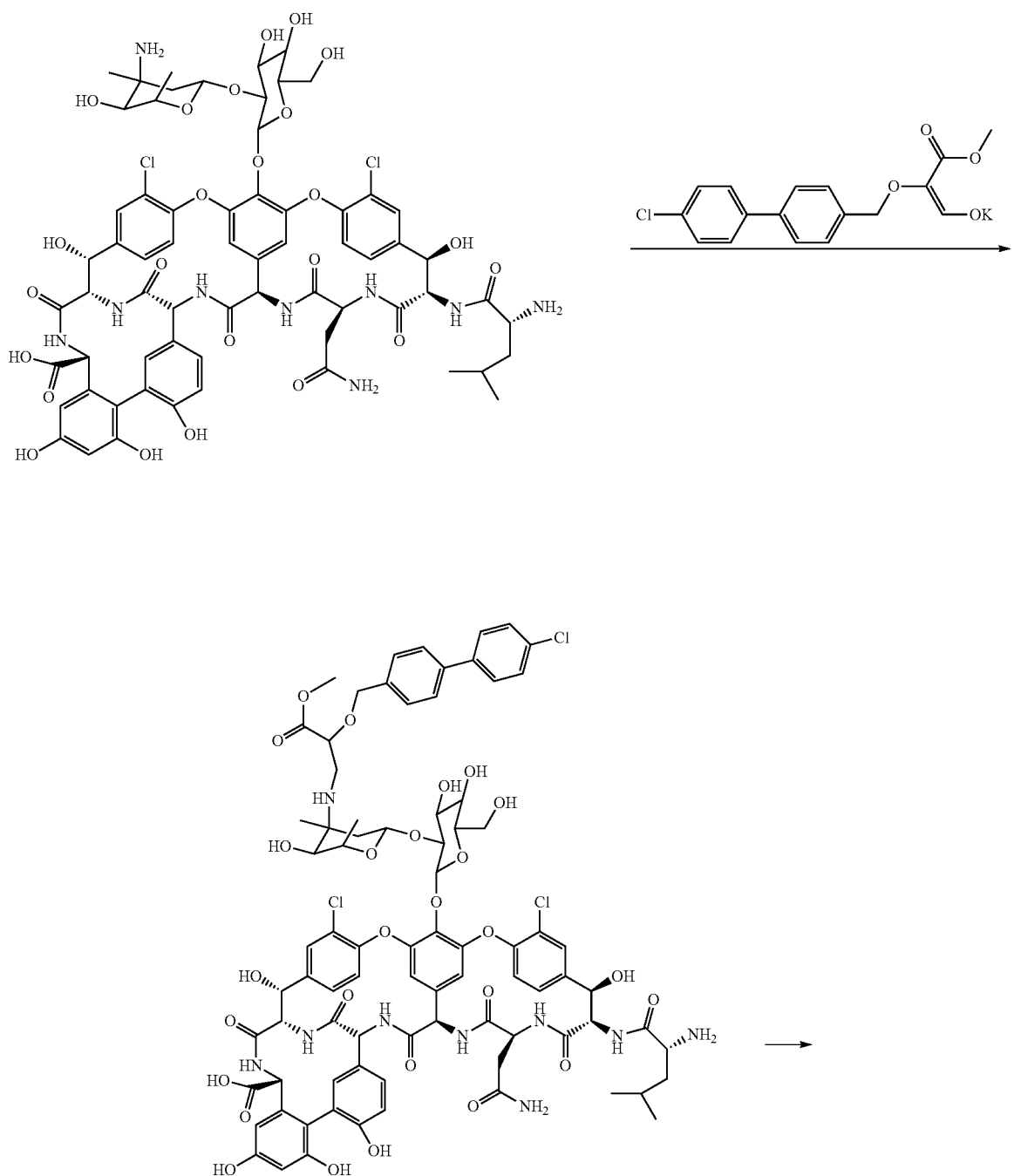

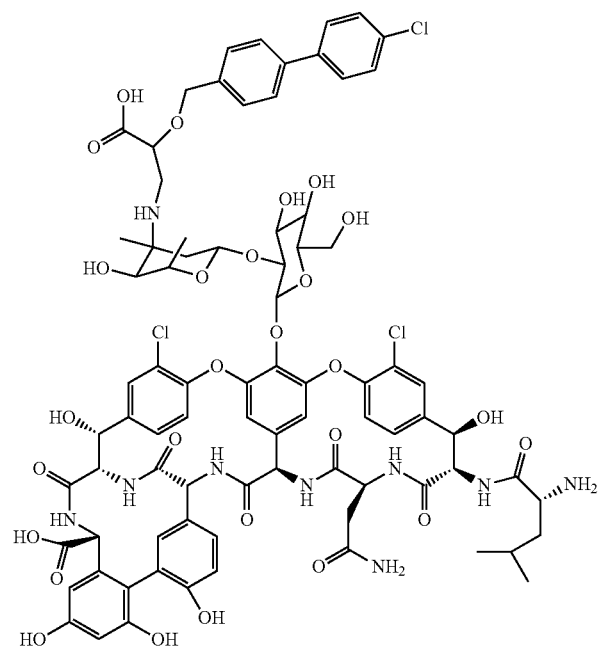
Synthetic Procedure:
Step 1:
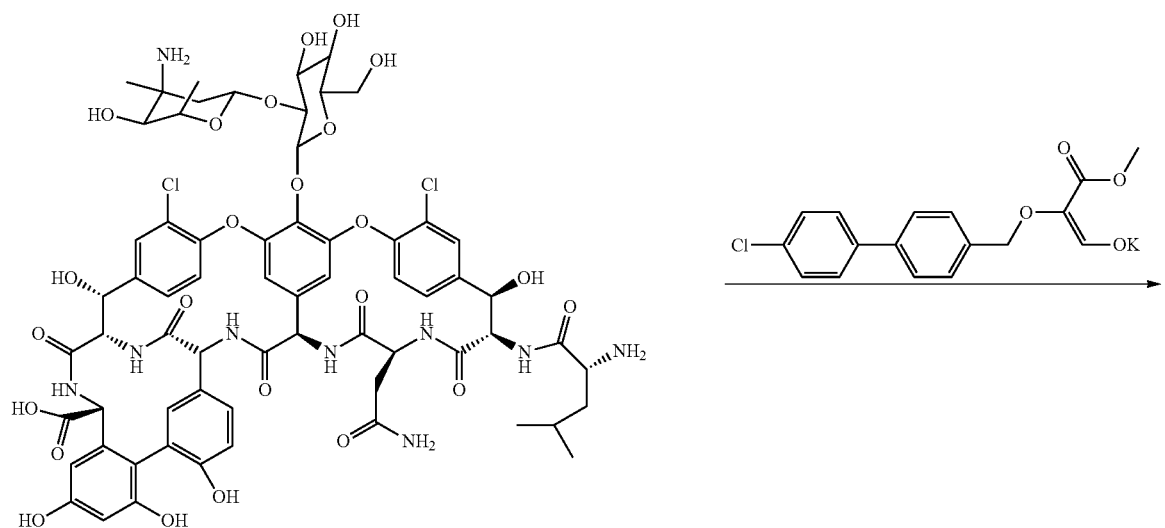

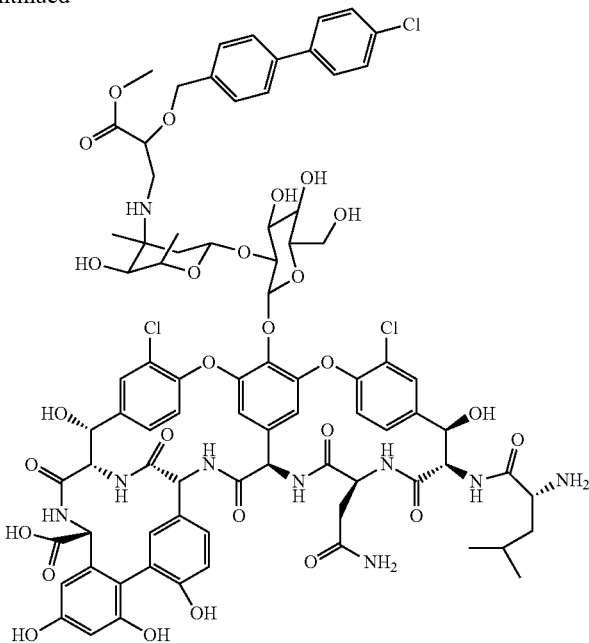

A 250 ml single necked flask was charged with 1.5 g of norvancomycin, which was dissolved in 80 ml of N,N-dimethylformamide at 80° C., 250 mg of the product obtained from Step 2 of Example 1 was added, followed by addition of 130 mg of sodium cyano borohydride in batch, and after addition, the reaction was performed for 2 hours, 5 ml of acetic acid was added and stirred for 0.5 hour, the reaction solution was poured into 100 ml of diethyl ether whereupon a solid precipitated, suction filtration was performed, the filter cake was stirred/washed with 40 ml of a solvent mixture of methanol and diethyl ether (1:3) followed by suction filtration, the crude product thus obtained was isolated by preparative HPLC to obtain 15 mg of the product. MS m/e 1736.5, 1737.5, 1738.5 (M+1)

Step 2:

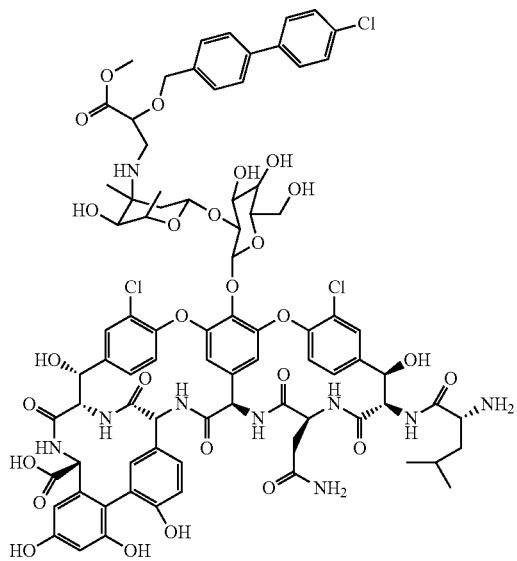

-continued

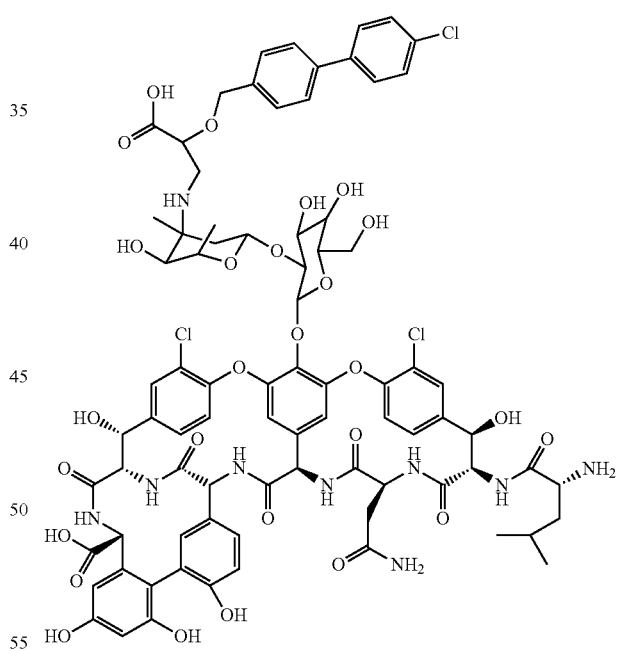

5 mg of the product obtained from the previous step was dissolved in a solvent mixture of 1 ml of tetrahydrofuran and 1 ml of water, 2.0 mg of lithium hydroxide was added with stirring, the reaction solution was stirred for 1 hour, 10 mg of acetic acid was added to quench the reaction, the organic solvent was removed by a rotary evaporator, purification by preparative HPLC obtained 3.5 mg of the product, MS m/e 1722.5, 1723.5, 1724.5 (M+1)

Example 6
Compounds V51, V52, V53, V54, V55, V57, V58, V59, V60, V68 and the like were prepared according to the process as described in Example 1.
Example 7
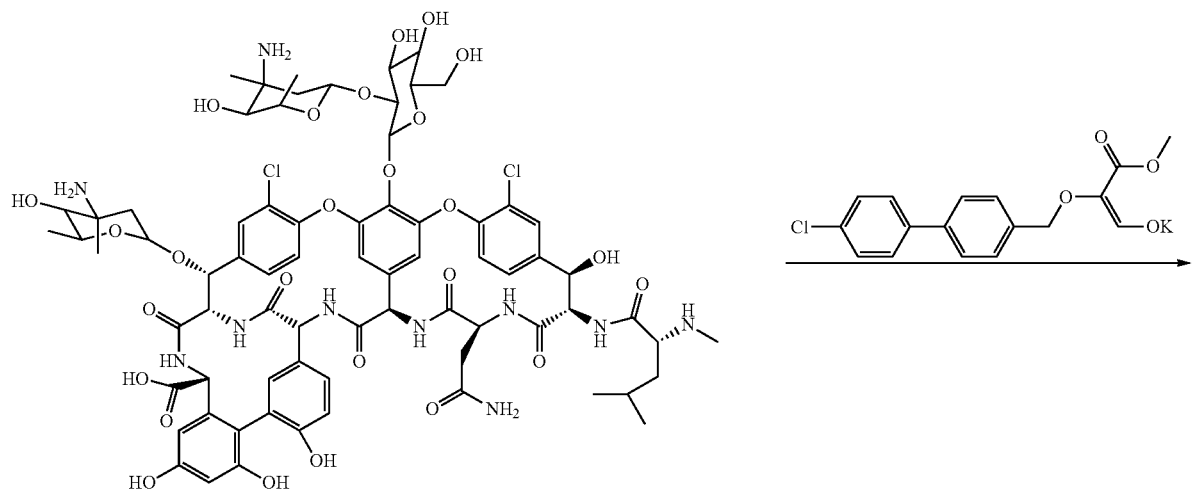
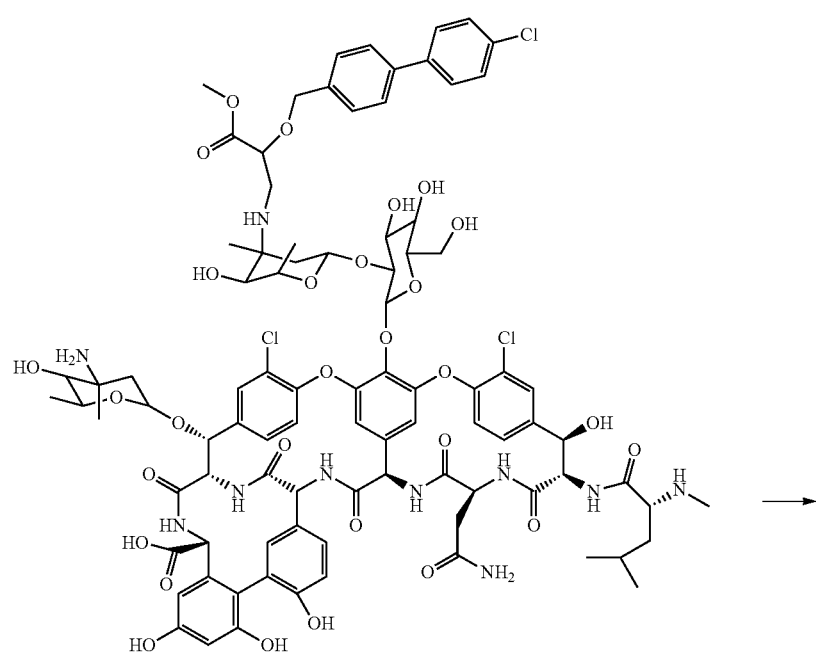

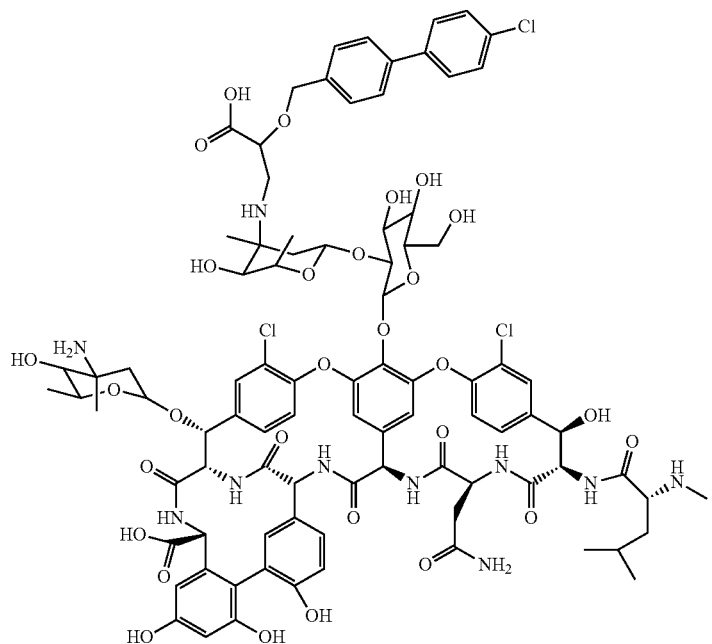
35
Synthetic Procedure:
Step 1:
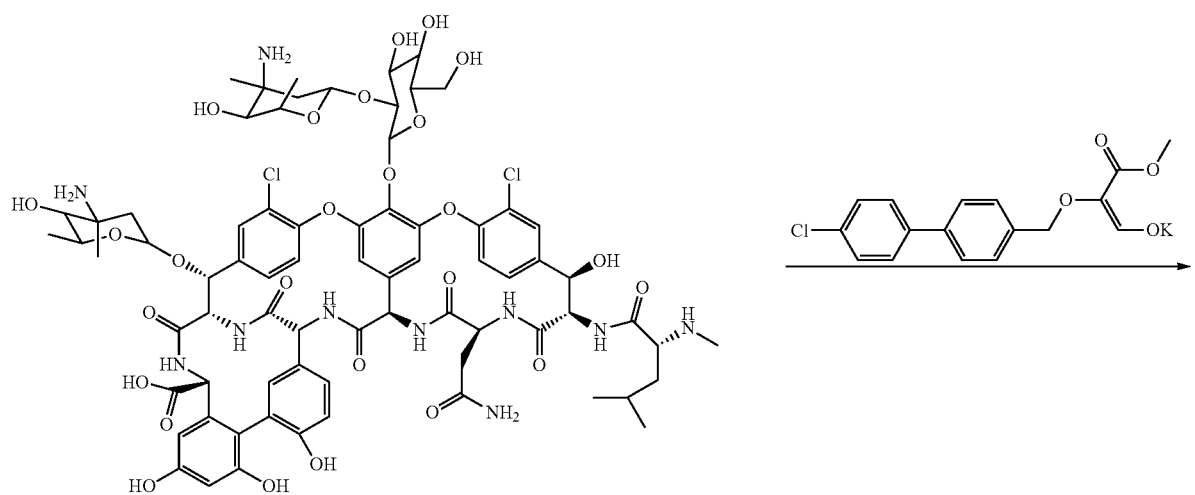

-continued

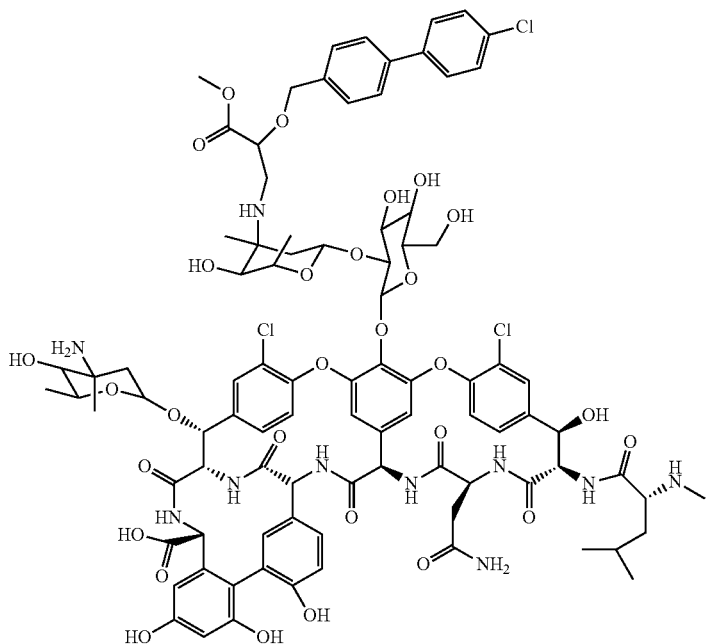

A 500 ml single necked flask was charged with 3.1 g of 4-epi-vancosaminyl vancomycin, which was dissolved in 150 ml of N,N-dimethylformamide at 80° C., 500 mg of the product obtained from Step 2 of Example 1 was added, followed by addition of 250 mg of sodium cyano borohydride in batch, and after addition, the reaction was performed for 2 hours, 7 ml of acetic acid was added and stirred for 0.5 hour, the reaction solution was poured into 150 ml of diethyl ether whereupon a solid precipitated, suction filtration was performed, the filter cake was stirred/washed with 40 ml of a solvent mixture of methanol and diethyl ether (1:3) followed by suction filtration, the crude product thus obtained was isolated by preparative HPLC to obtain 7.8 mg of the product. MS m/e 1896.5, 1893.5, 1894.5 (M+1)

Step 2:

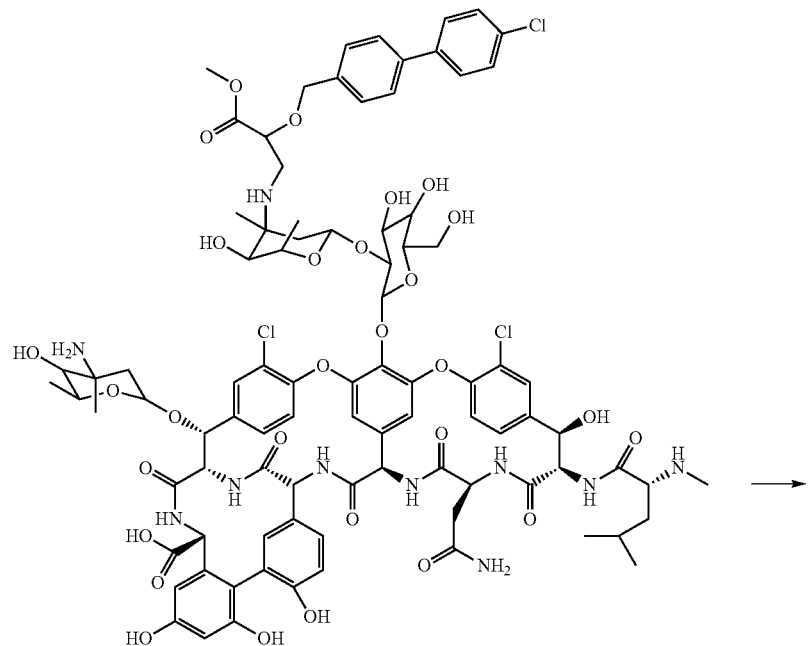

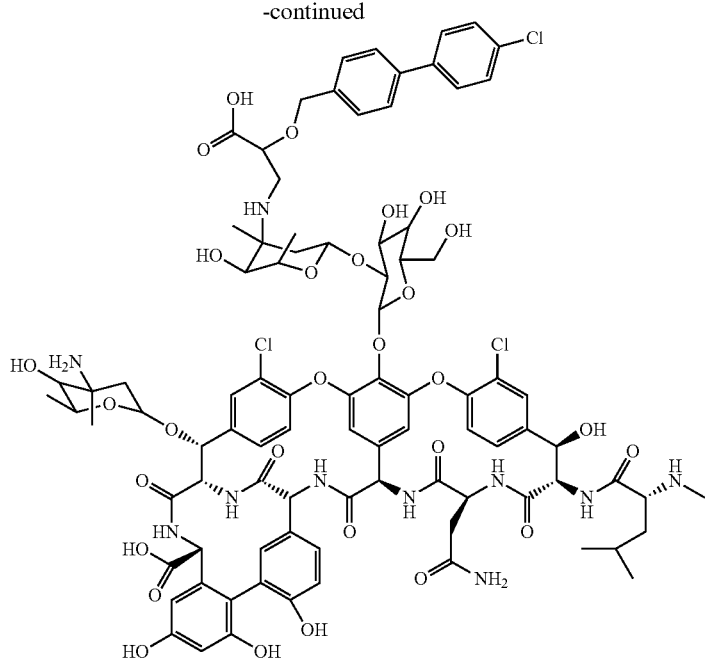

5 mg of the product obtained from the previous step was dissolved in a solvent mixture of 1 ml of tetrahydrofurane and 1 ml of water, 2.0 mg of lithium hydroxide was added with stirring, the reaction solution was stirred for 1 hour, 10 mg of acetic acid was added to quench the reaction, the organic solvent was removed by a rotary evaporator, purification by preparative HPLC obtained 1.8 mg of the product, MS m/e 1881.5, 1880.5, 1879.5 (M+1)

Example 8

Compounds V61, V62, V63, V64, V65, V66, V69 and the like were prepared according to the process as described in Example 7.

What is claimed is:
1. A vancomycin derivative of formula (I):

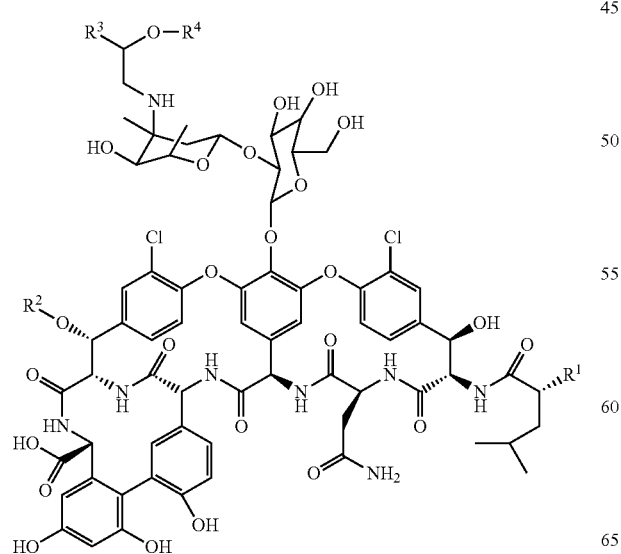

(I)

wherein:
$R^1$ is —NHCH$_3$ or —NH$_2$;
$R^2$ is H or 4-epi-vancosaminyl;
$R^3$ is —(R)COOR$^a$ or —(S)COOR$^a$ or —(R/S)COOR$^a$; wherein R$^a$ is H, C1-C20 alkyl, C5-C12 aryl, C2-C12 alkenyl or C2-C12 alkynyl;
$R^4$ is hydrogen, C1-C20 alkyl, C5-C12 aryl, C2-C12 alkenyl, C2-C12 alkynyl, (C1-C20 alkyl)-$R^5$ or (C1-C20 alkyl)-O—$R^5$; wherein $R^5$ has the following structure:
(a) unsubstituted C5-C12 aryl or mono-substituted C5-C12 aryl or poly-substituted C5-C12 aryl, wherein the substituent independently is:
(I) hydroxyl
(II) halogen
(III) nitro
(IV) amino
(V) C1-C20 alkyl
(b) the following structure:

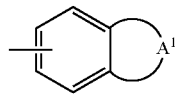

$A^1$ is —OC(A$^2$)2-C(A$^2$)2-O— or —O—C(A$^2$)2-O— or —C(A$^2$)2-O— or —C(A$^2$)2-C(A$^2$)2-C(A$^2$)2-C(A$^2$)2-, wherein A$^2$ independently is hydrogen or C1-C20 alkyl
(c) the following structure:

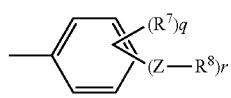

q is 0-4, wherein $R^7$ independently is the following group:
(I) hydrogen
(II) hydroxyl (III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

2. The vancomycin derivative of claim 1, wherein:
$R^1$ is —$NHCH_3$ or —$NH_2$;
$R^2$ is H or 4-epi-vancosaminyl;
$R^3$ is —(R)$COOR^a$ or —(S)$COOR^a$ or —(R/S)$COOR^a$; wherein $R^a$ is H, C1-C20 alkyl, C5-C12 aryl, C2-C12 alkenyl or C2-C12 alkynyl;
$R^4$ is C1-C20 alkyl.

3. The vancomycin derivative of claim 1, wherein:
$R^1$ is —$NHCH_3$ or —$NH_2$;
$R^2$ is H or 4-epi-vancosaminyl;
$R^3$ is —(R)$COOR^a$ or —(S)$COOR^a$ or —(R/S)$COOR^a$; wherein $R^a$ is H, C1-C20 alkyl, C5-C12 aryl, C2-C12 alkenyl or C2-C12 alkynyl;
$R^4$ is (C1-C20 alkyl)-$R^5$, wherein $R^5$ has the following structure:

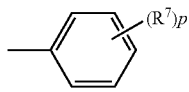

p is 1-5, wherein $R^7$ independently is the following group:
(I) hydrogen
(II) hydroxyl
(III) halogen
(IV) nitro
(V) amino
(VI) C1-C20 alkyl.

4. The vancomycin derivative of claim 1, wherein:
$R^1$ is —$NHCH_3$ or —$NH_2$;
$R^2$ is H or 4-epi-vancosaminyl;
$R^3$ is —(R)$COOR^a$ or —(S)$COOR^a$ or —(R/S)$COOR^a$; wherein $R^a$ is H, C1-C20 alkyl, C5-C12 aryl, C2-C12 alkenyl or C2-C12 alkynyl;
$R^4$ is (C1-C20 alkyl)-$R^5$, wherein $R^5$ has the following structure:

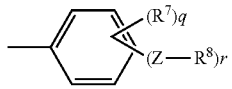

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

5. The vancomycin derivative of claim 1, wherein:
$R^1$ is —$NHCH_3$ or —$NH_2$;
$R^2$ is H or 4-epi-vancosaminyl;
$R^3$ is —(R)$COOR^a$ or —(S)$COOR^a$ or —(R/S)$COOR^a$; wherein $R^a$ is H;
$R^4$ is (C1-C20 alkyl)-$R^5$, wherein $R^5$ has the following structure:

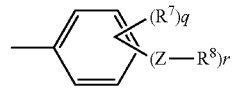

q is 0-4, wherein $R^7$ independently is the following group:
(I) hydrogen
(II) hydroxyl
(III) halogen
(IV) nitro
(V) amino
(VI) C1-C20 alkyl
r is 1-5, but q+r is no more than 5
Z is the following case:
(I) a single bond
(II) —(C1-C12)alkyl-
$R^8$ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

6. A method for treating an infection caused by a gram-positive bacteria or vancomycin-resistant bacteria comprising contacting the bacteria with a compound as described in claim 1.

7. A process for preparing the vancomycin derivative according to claim 1, comprising treating vancomycin or an analogue thereof and a compound of formula

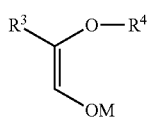
with a reductive agent in a polar solvent followed by hydrolysis, and if $R^a$ is H in the formula, the product is directly obtained after reduction;
wherein the vancomycin and the analogue thereof are vancomycin of formula (II), norvancomycin of formula (III), 4-epi-vancosaminyl vancomycin of formula (IV) or 4-epi-vancosaminyl norvancomycin of formula (V):
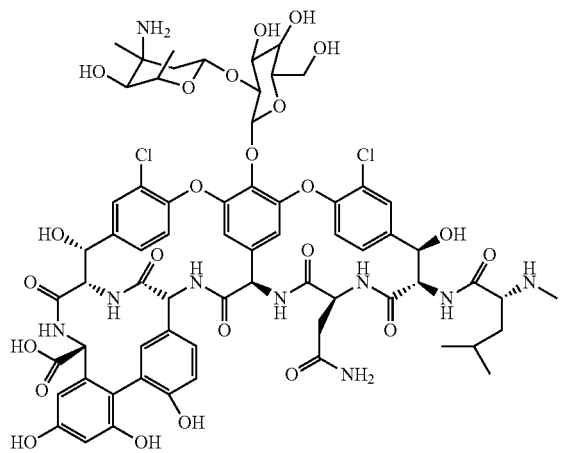
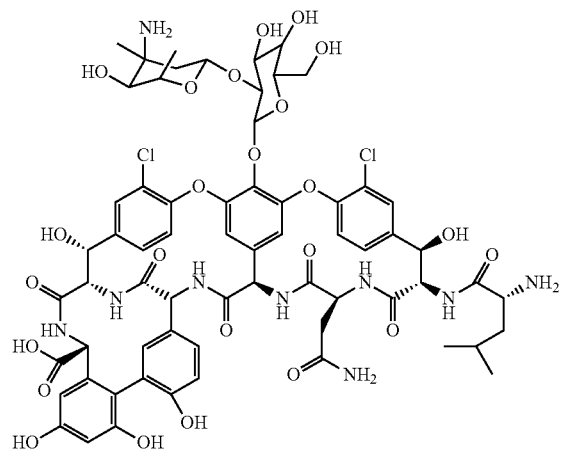
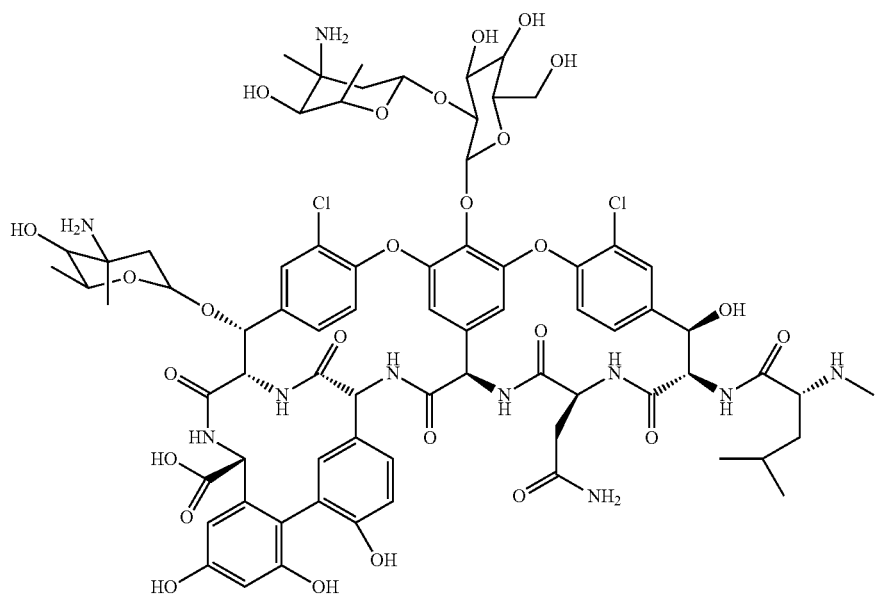

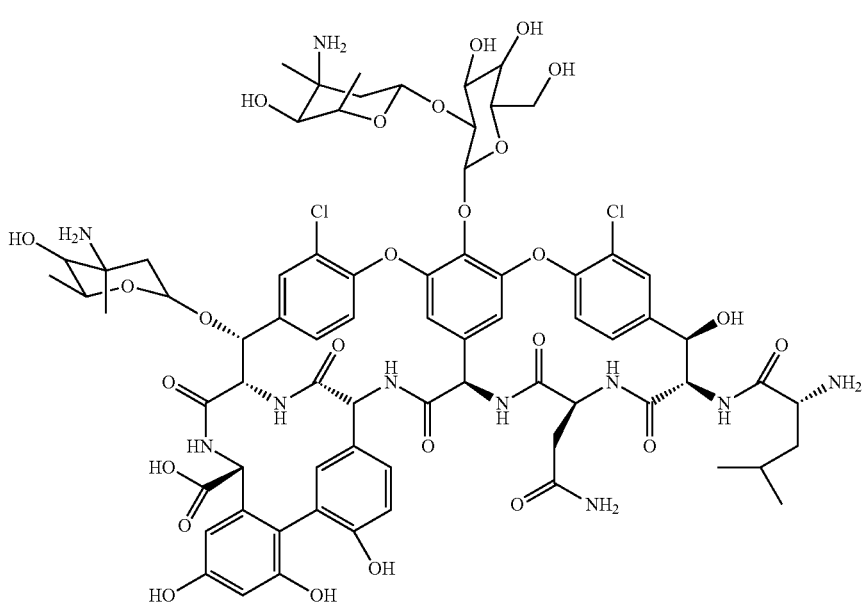

(V)

wherein

M is alkali metal or alkaline earth metal;

R³ is —(R)COORᵃ or —(S)COORᵃ or —(R/S)COORᵃ, and Rᵃ is H, C1-C20 alkyl, C5-C12 aryl, C2-C12 alkenyl or C2-C12 alkynyl;

R⁴ is hydrogen, C1-C20 alkyl, C5-C12 aryl, C2-C12 alkenyl, C2-C12 alkynyl, (C1-C20 alkyl)-R⁵ or (C1-C20 alkyl)-O—R⁵, and R⁵ has the following structure:

(a) unsubstituted C5-C12 aryl or mono-substituted C5-C12 aryl or poly-substituted C5-C12 aryl, wherein the substituent independently is:

(I) hydroxyl
(II) halogen
(III) nitro
(IV) amino
(V) C1-C20 alkyl (b) the following structure:

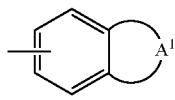

A¹ is —OC(A²)2-C(A²)2-O— or —O—C(A²)2-O— or —C(A²)2-N— or —C(A²)2-C(A²)2-C(A²)2-C(A²)2-, wherein A² independently is hydrogen or C1-C20 alkyl (c) the following structure:

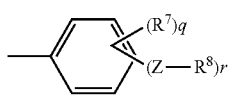

q is 0-4, wherein R⁷ independently is the following group:
(I) hydrogen
(II) hydroxyl
(III) halogen
(IV) nitro
(V) amino
(VI) C1-C20 alkyl r is 1-5, but q+r is no more than 5

Z is the following case:
(I) a single bond
(II) —(C1-C12)alkyl-

R⁸ independently is:
(I) C5-C12 aryl
(II) C5-C12 heteroaryl
(III) phenyl unsubstituted or substituted with 1 to 5 substituents independently selected from:
(a) hydrogen
(b) hydroxyl
(c) halogen
(d) nitro
(e) amino
(f) C1-C20 alkyl.

8. The process according to claim 7, wherein the polar solvent is methanol, ethanol, iso-propanol, tert-butanol, N, N-dimethylformamide, or N, N-dimethylacetamide; the temperature is between 0 and 80° C.; and the reductive agent is sodium borohydride, potassium borohydride, borane or a complex containing borane, sodium cyano borohydride, potassium cyano borohydride, sodium triacetoxy borohydride, or potassium triacetoxy borohydride.

9. A method for treating an infection caused by a gram-positive bacteria or vancomycin-resistant bacteria in an animal comprising, administering a compound as described in claim 1 to the animal.

10. The vancomycin derivative of claim1 that is selected from the group consisting of:

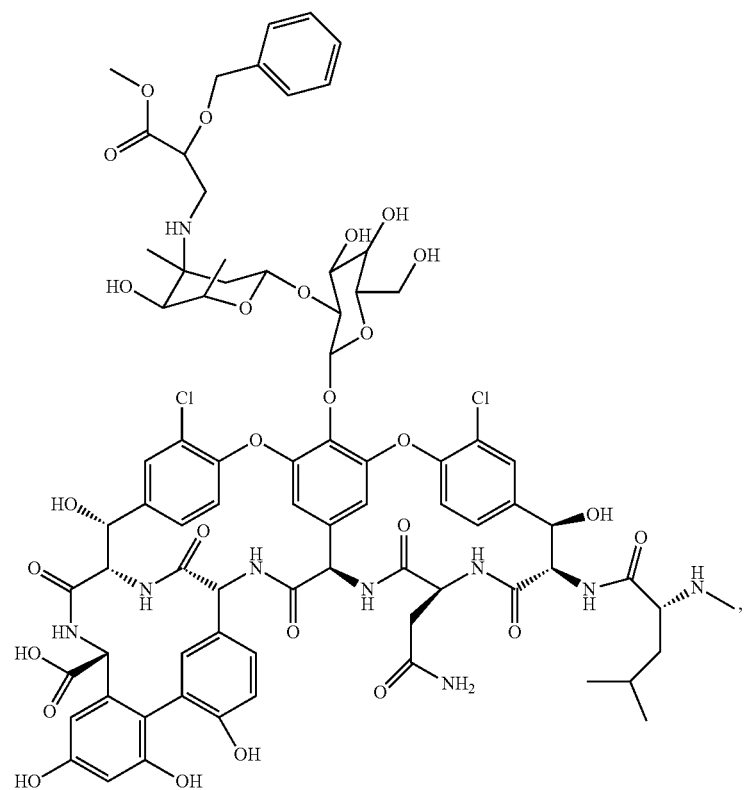
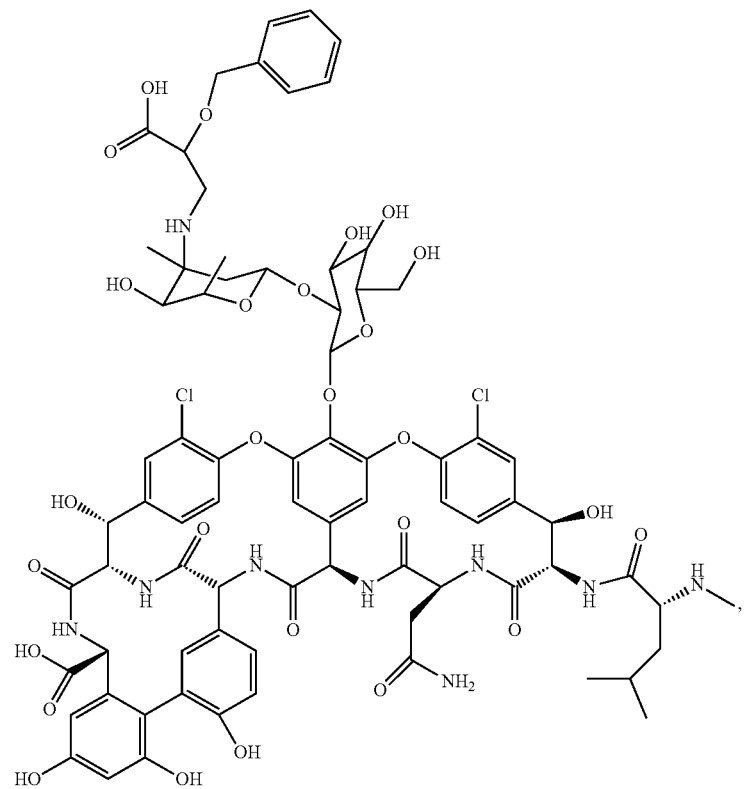

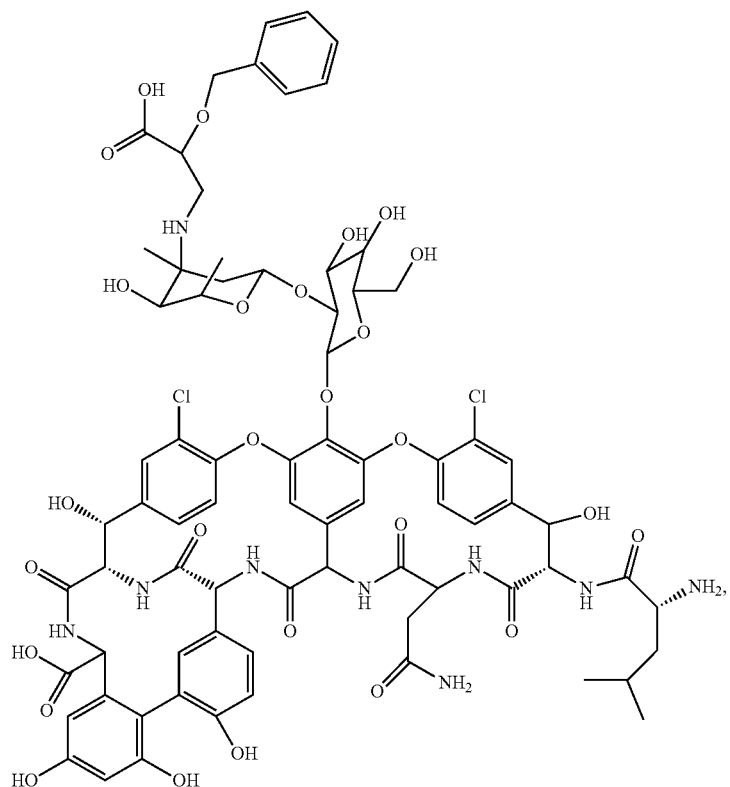
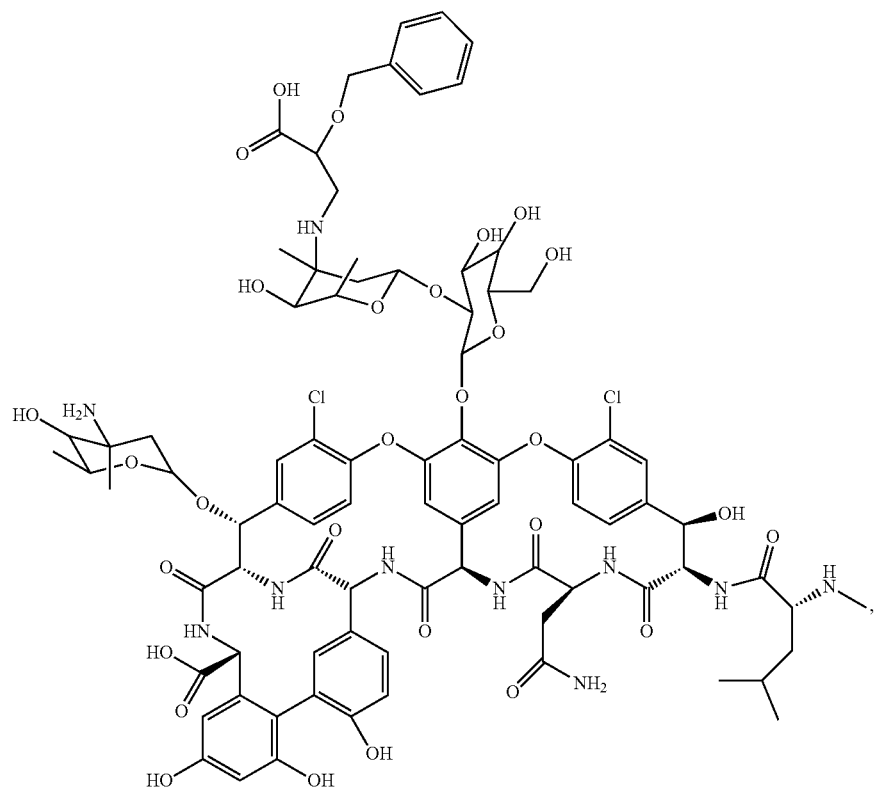

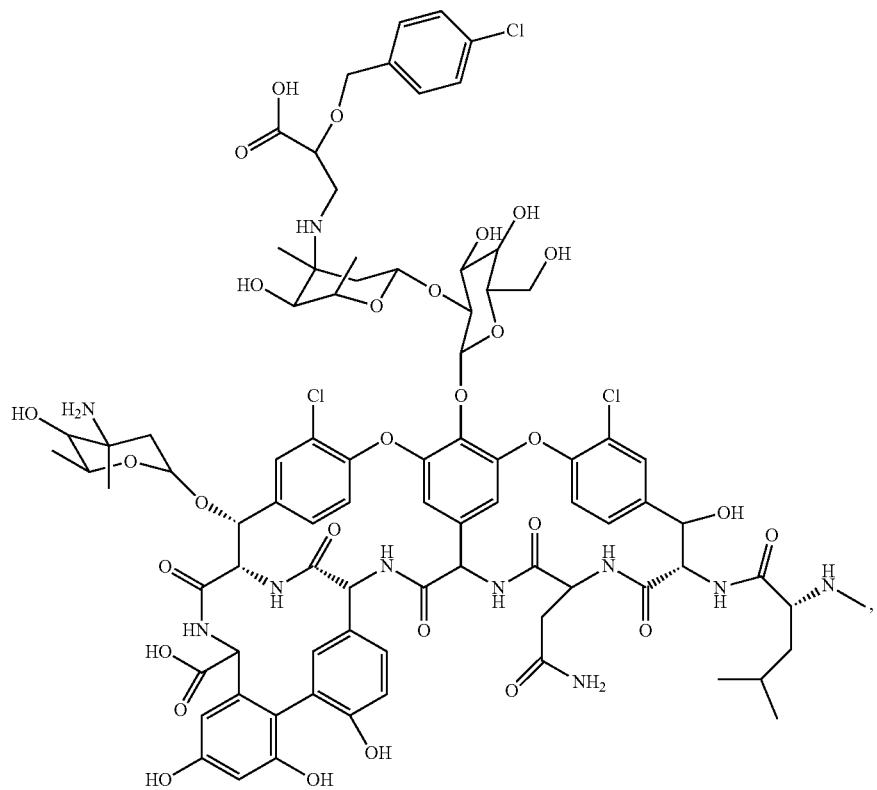
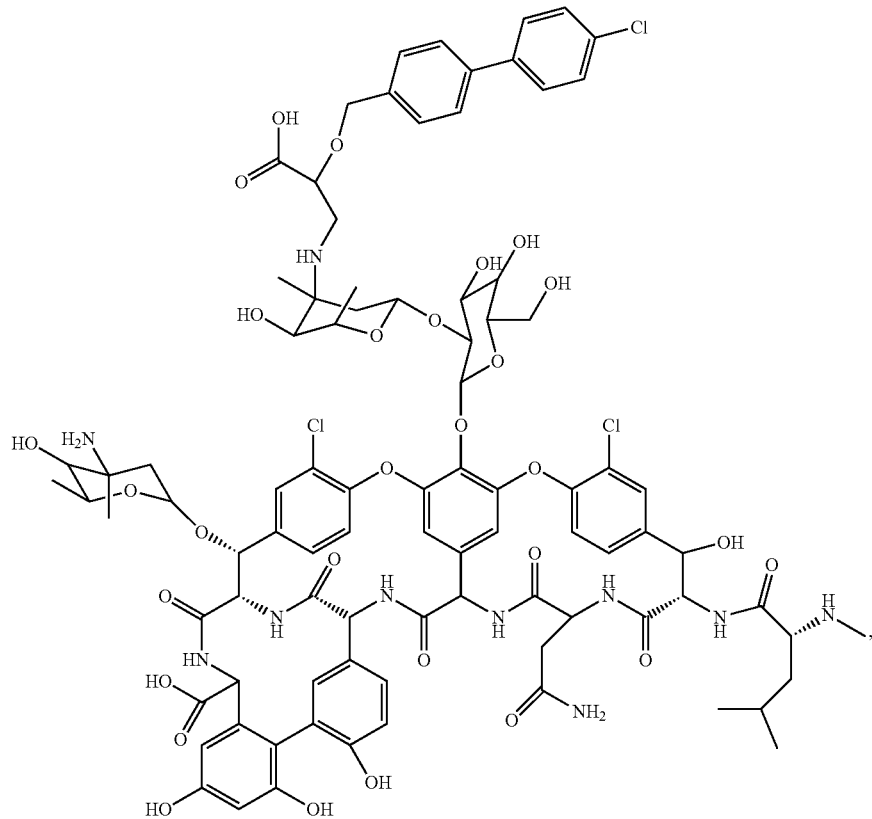

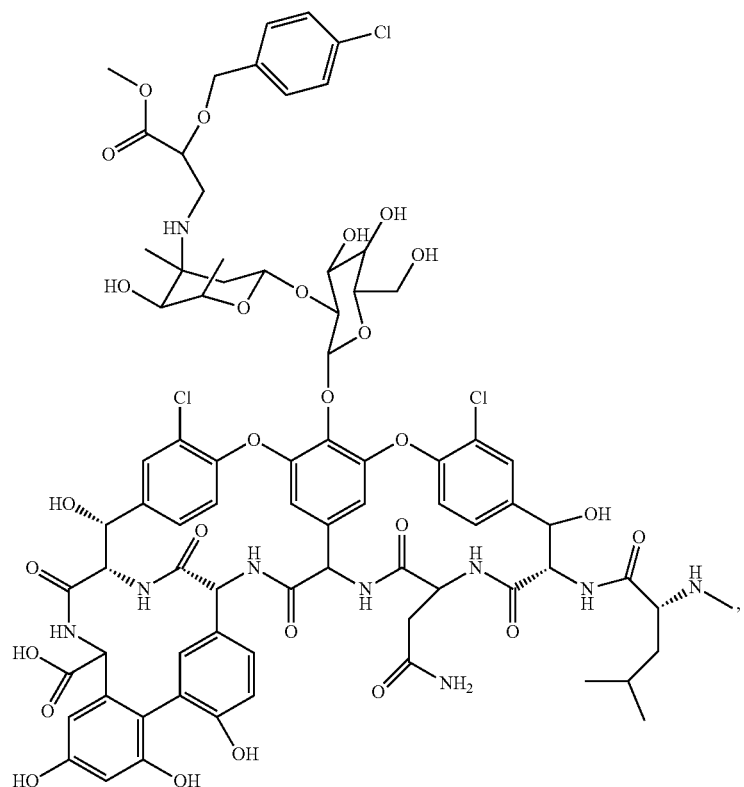
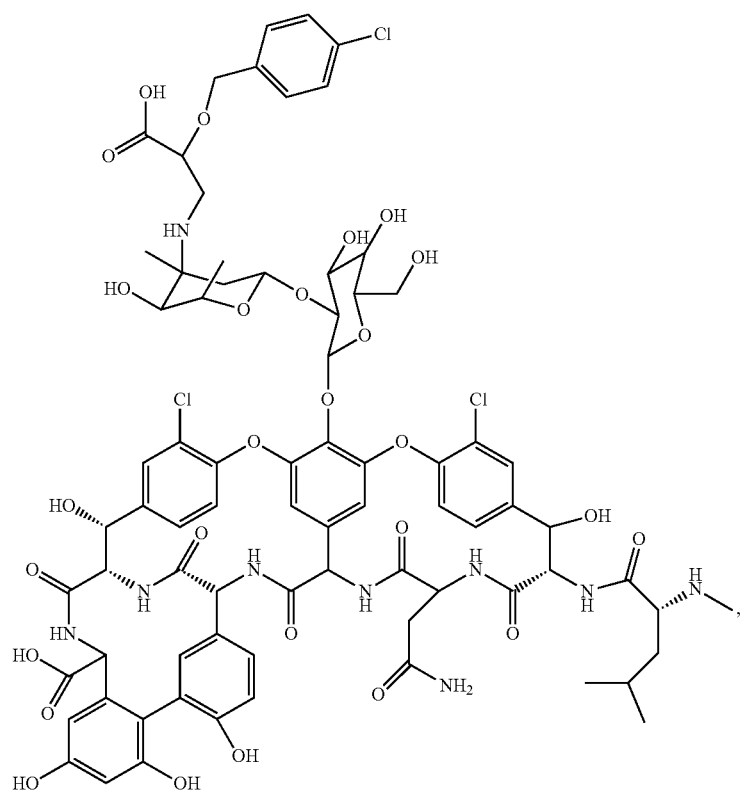

-continued
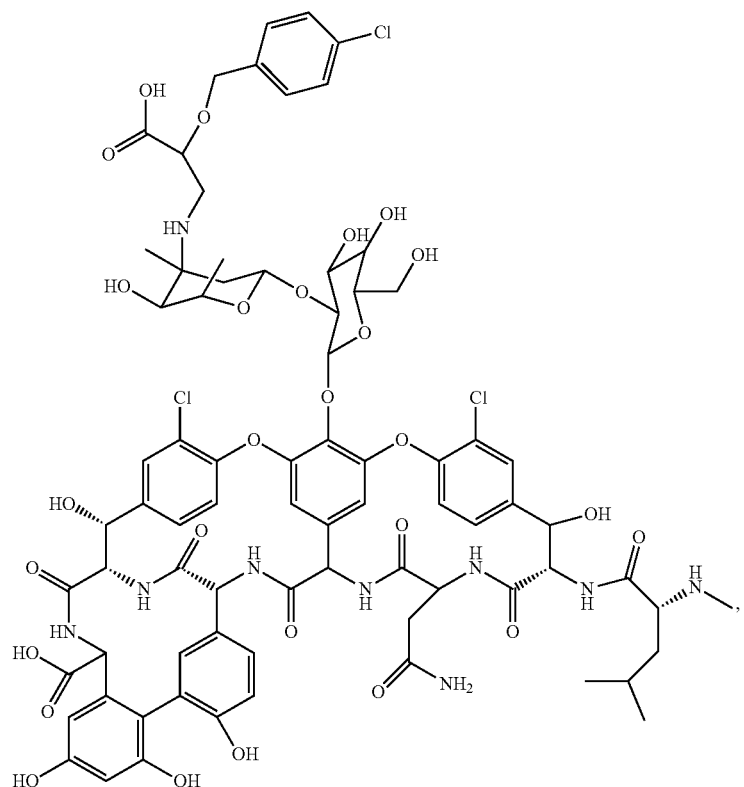
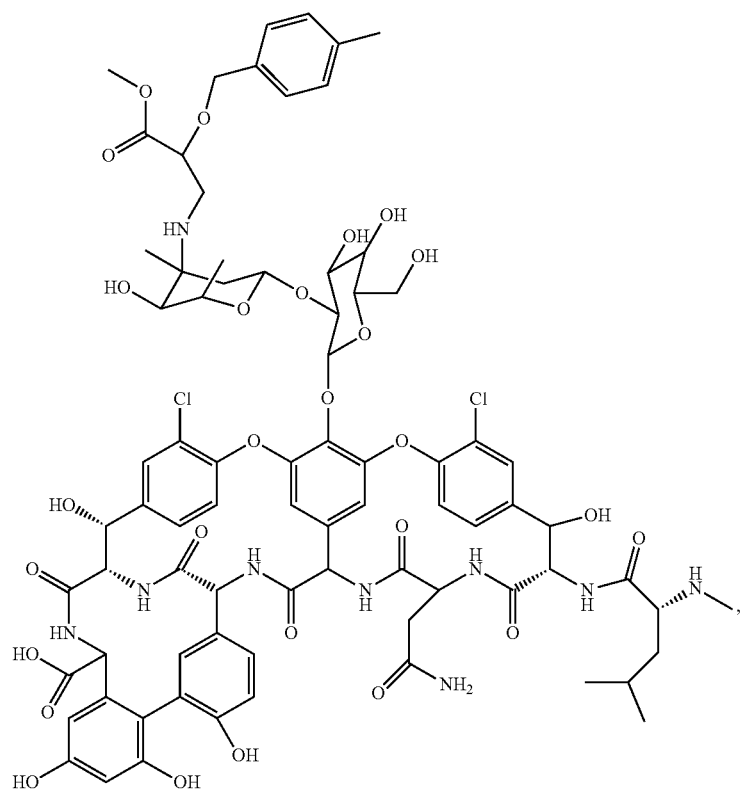

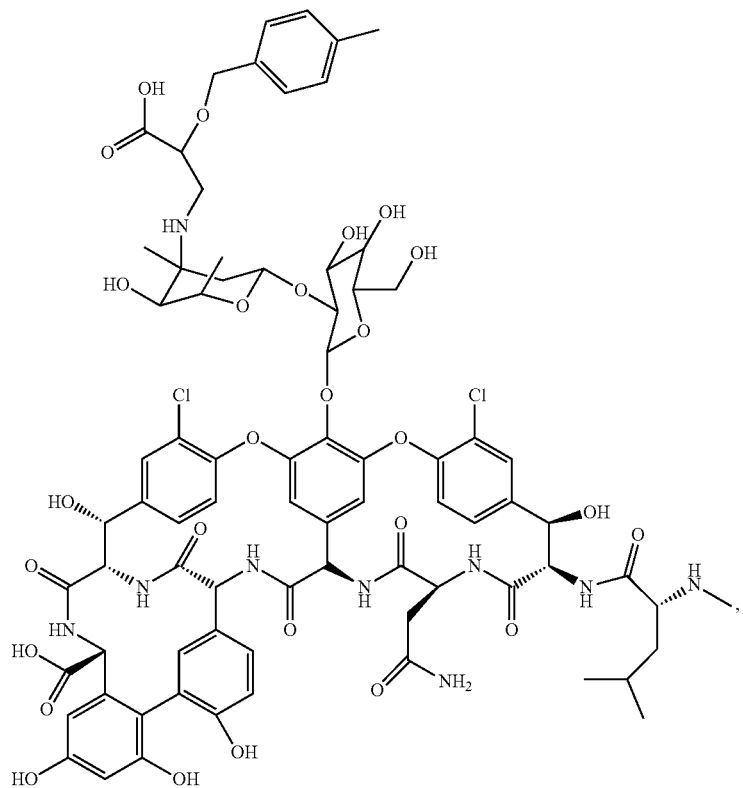
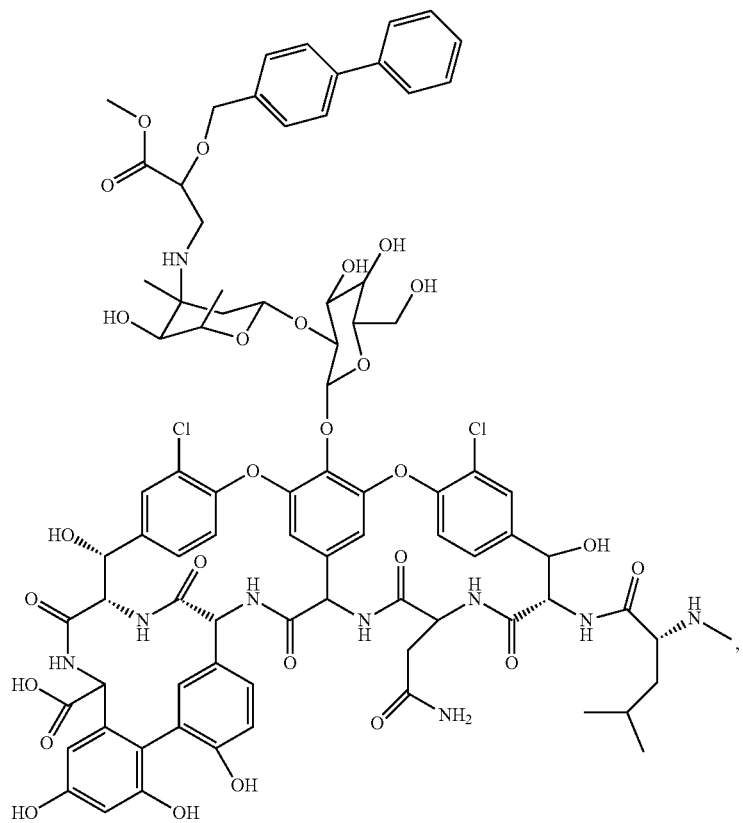

-continued
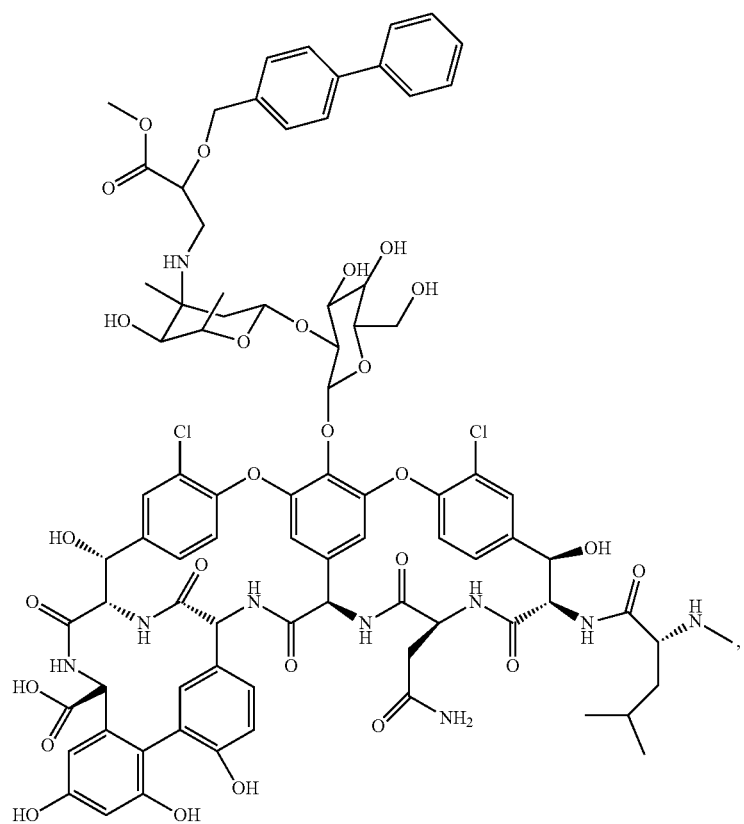
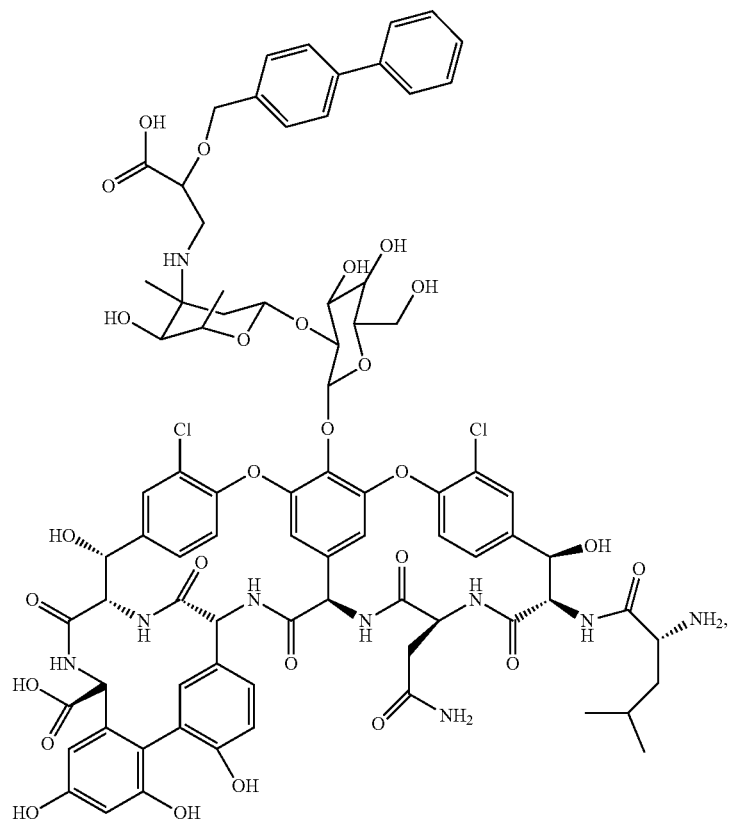

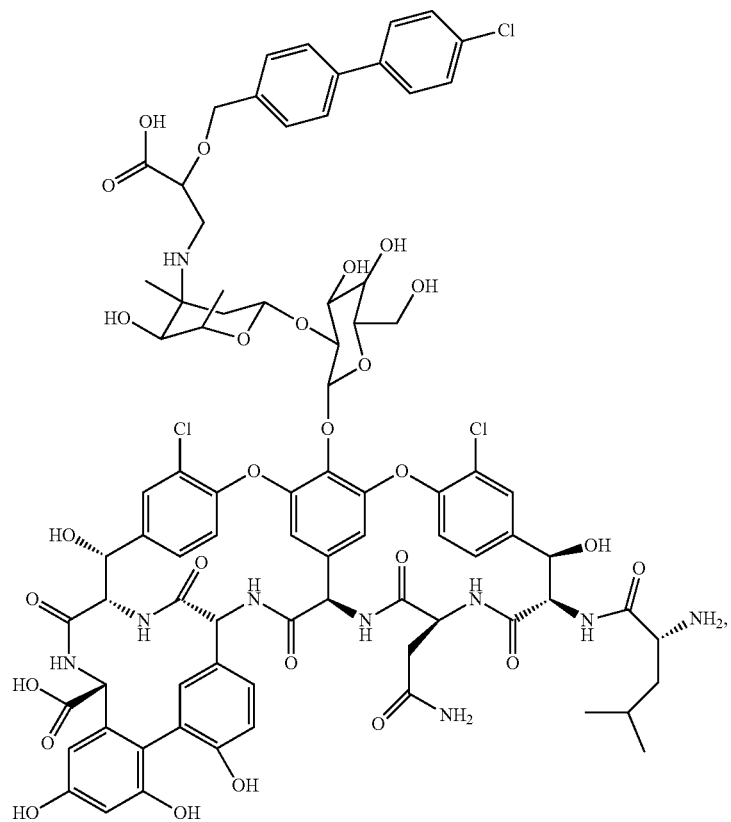
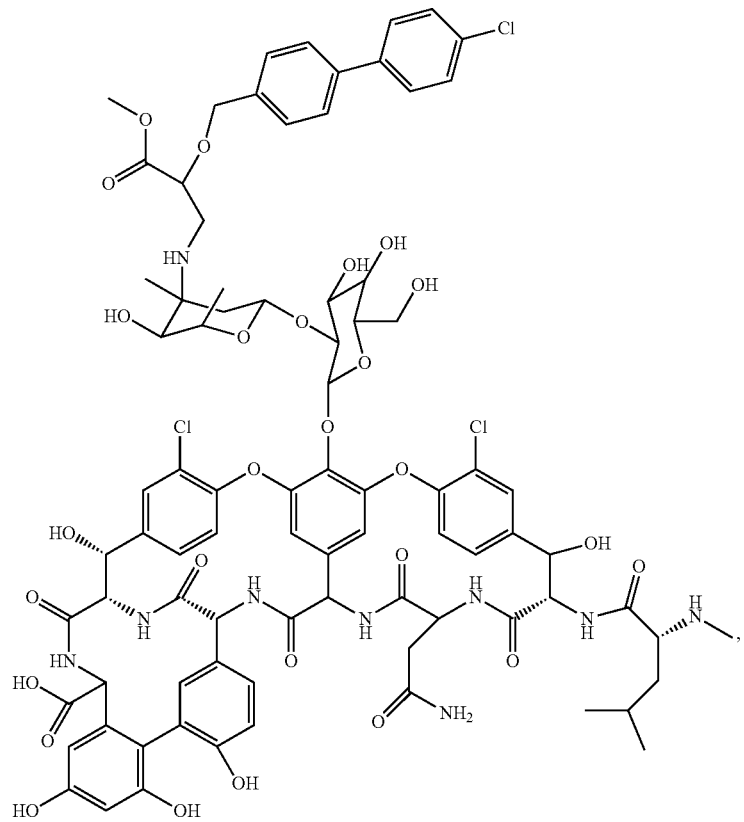

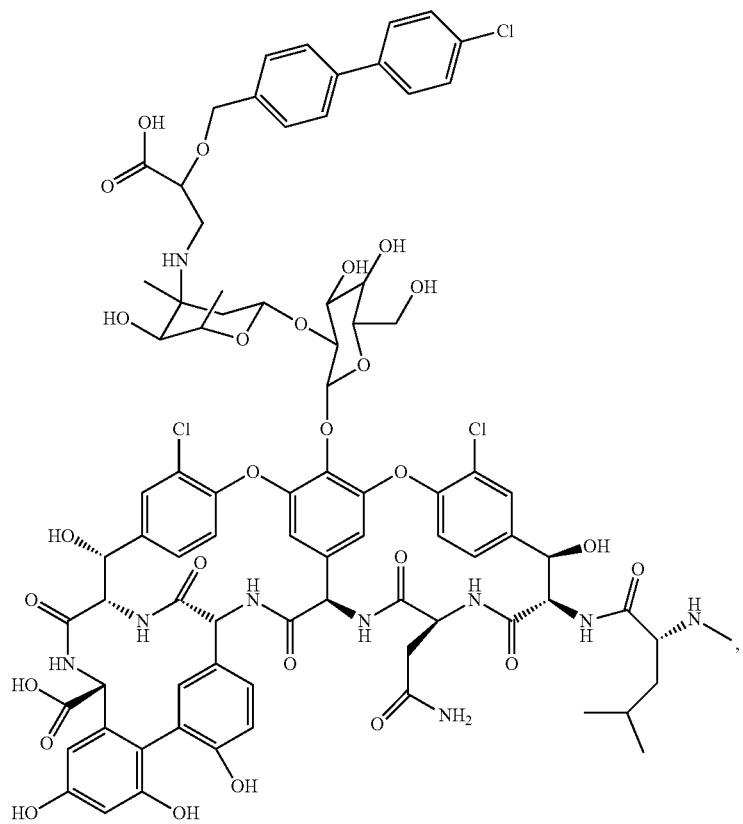
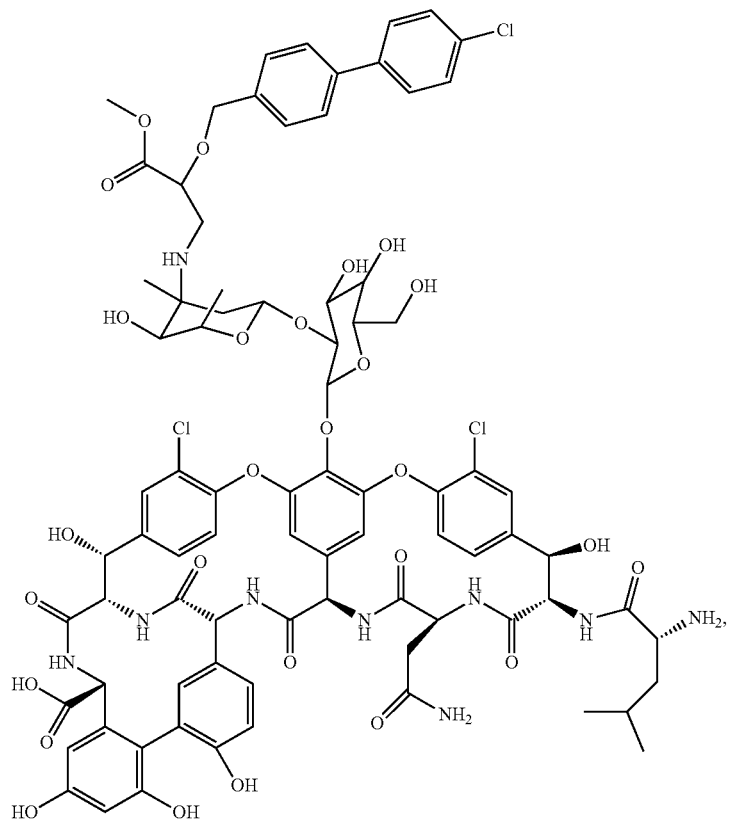

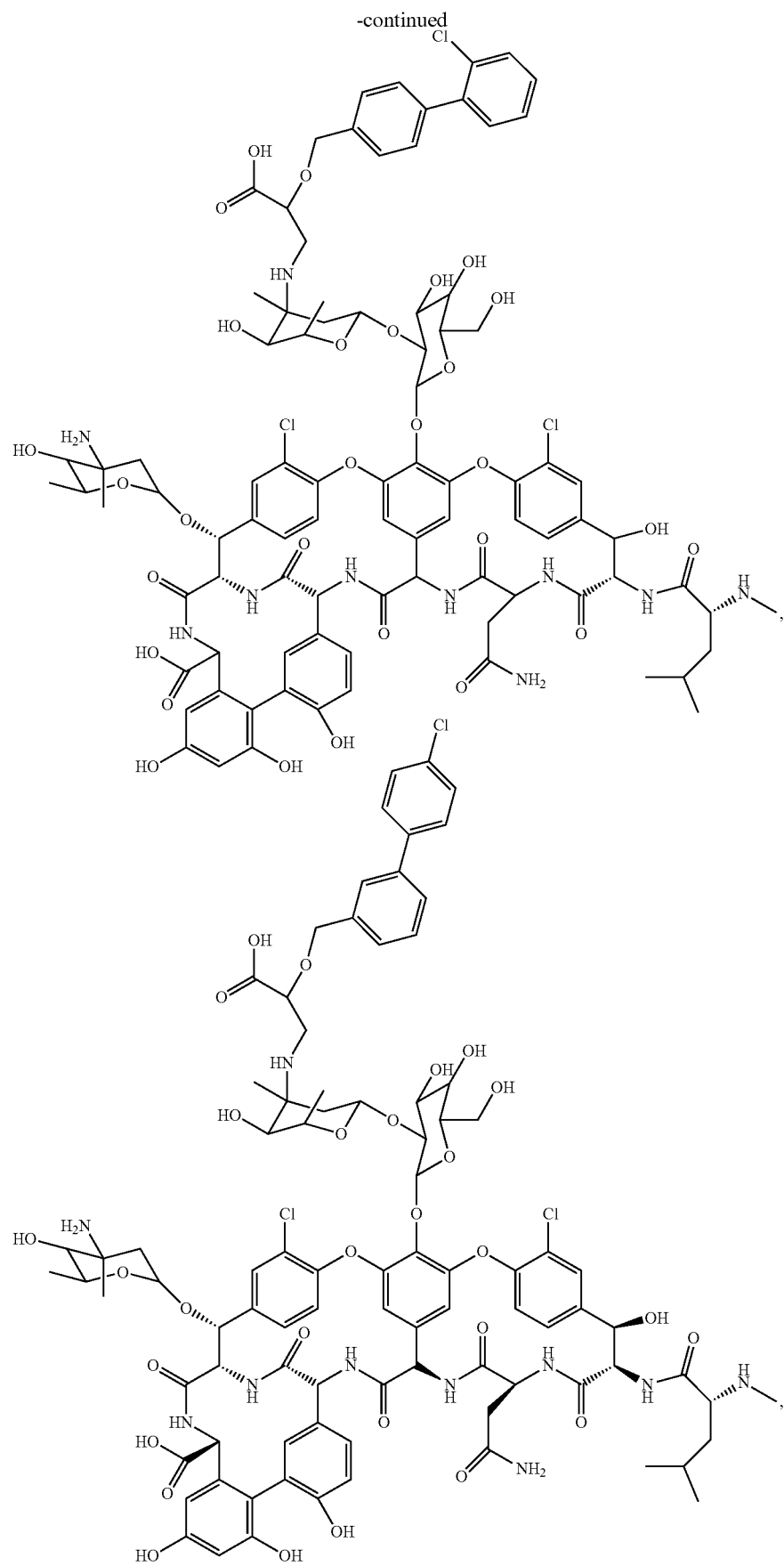

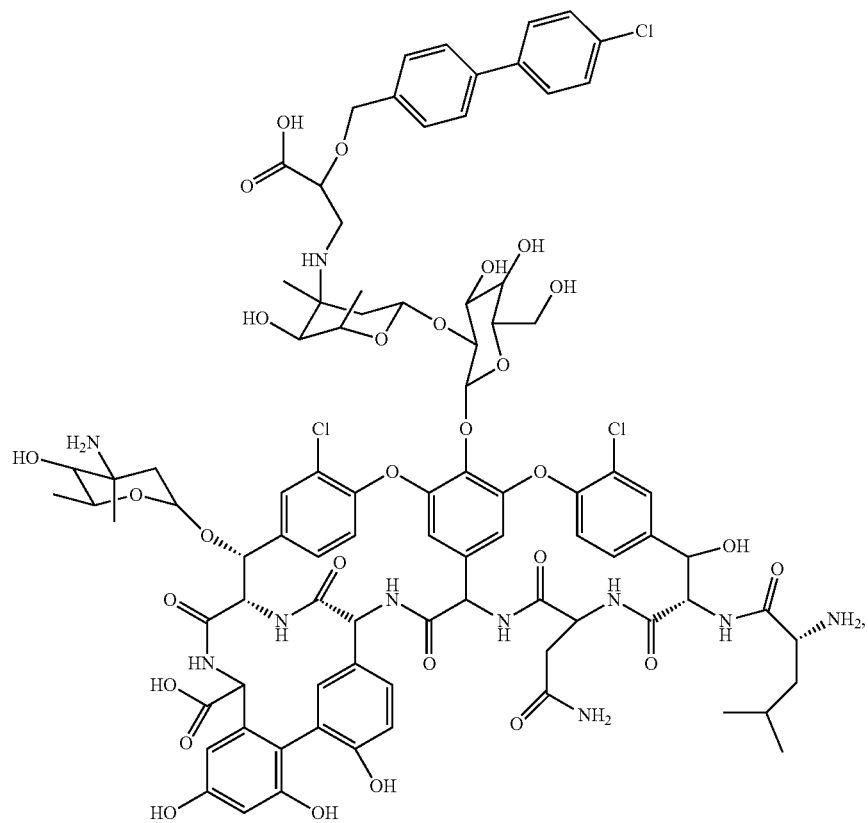
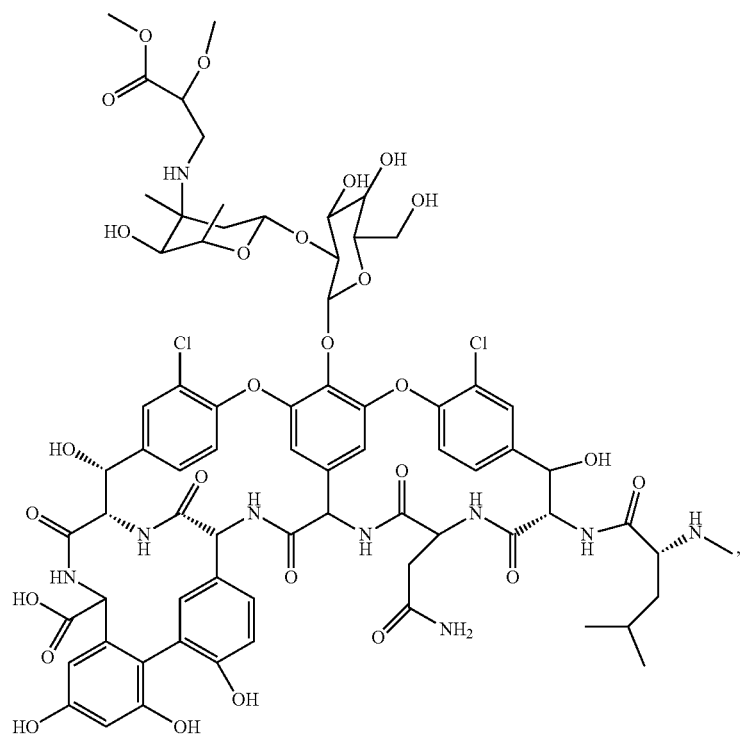

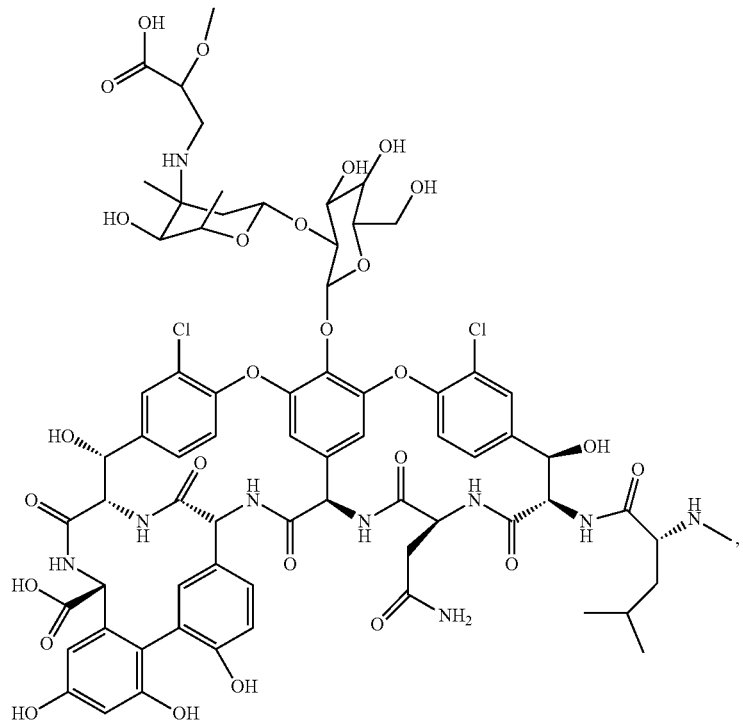
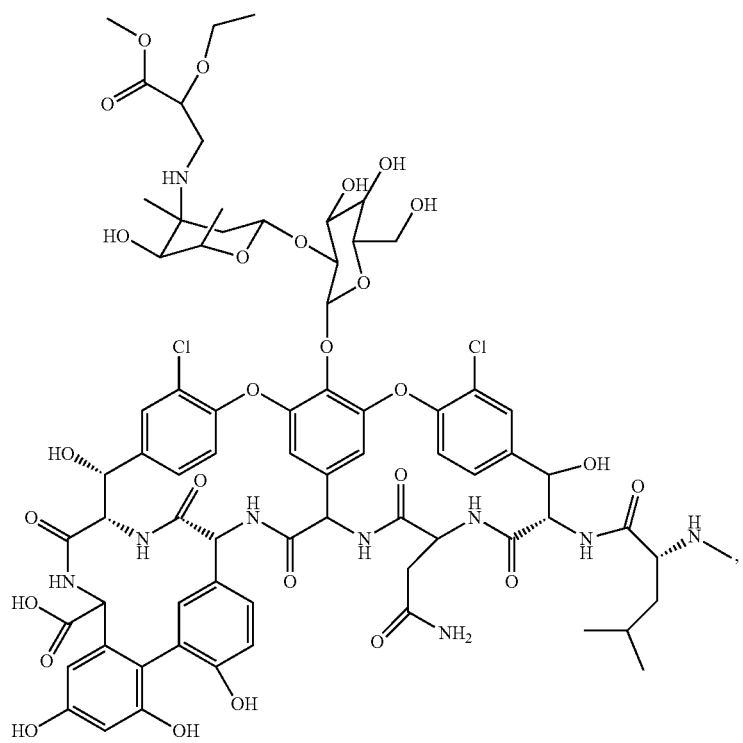

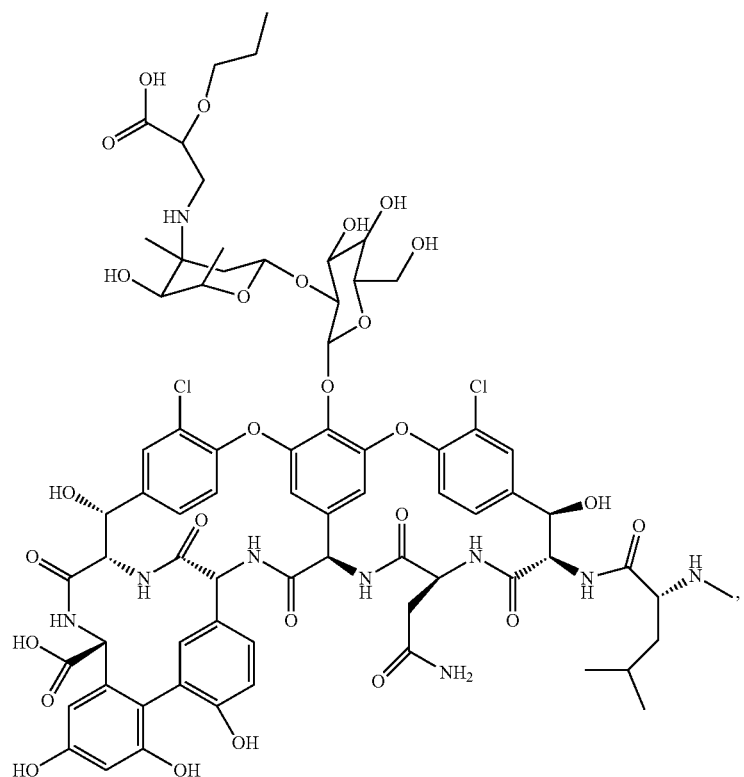
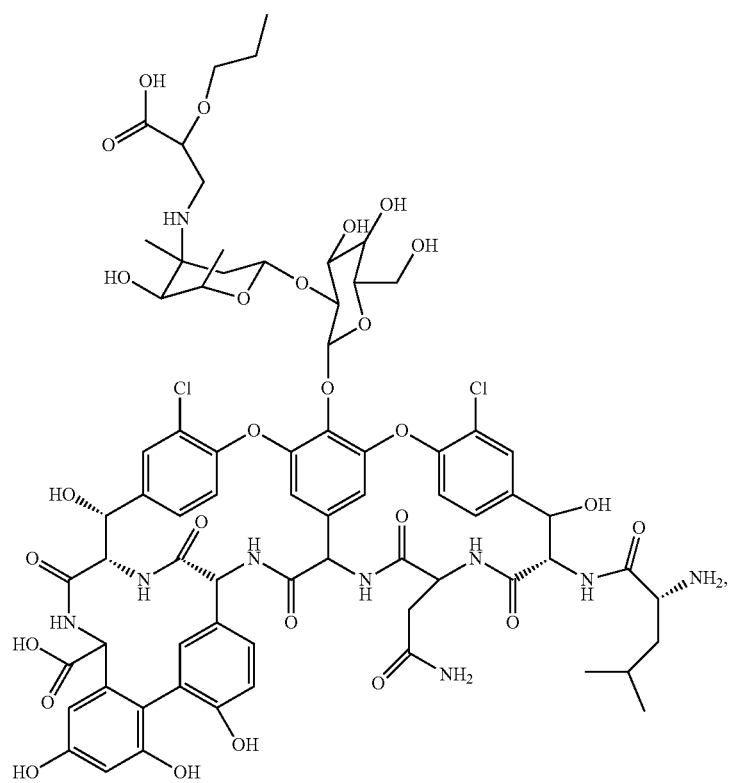

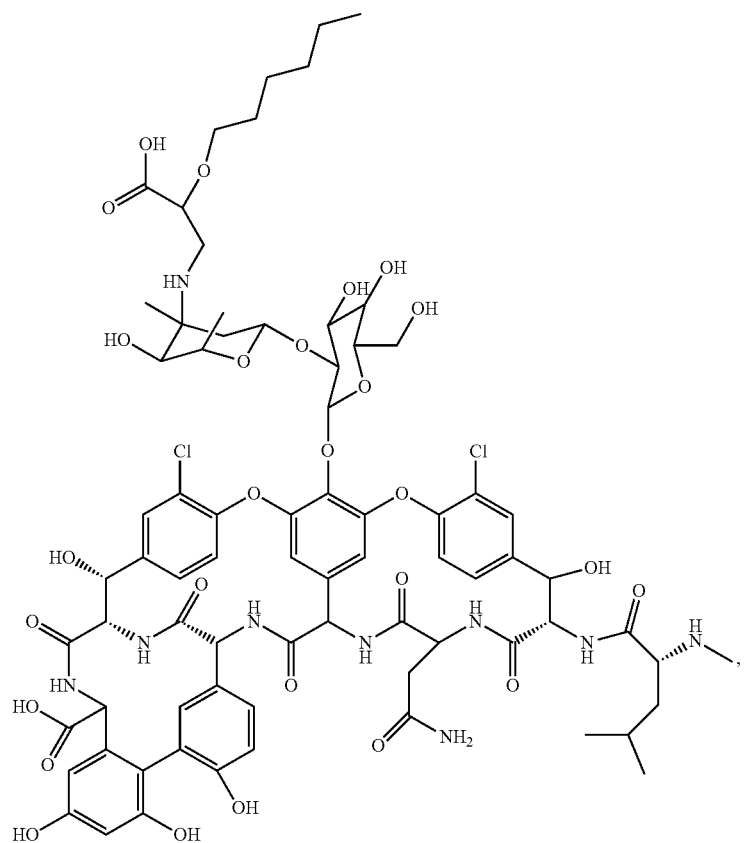
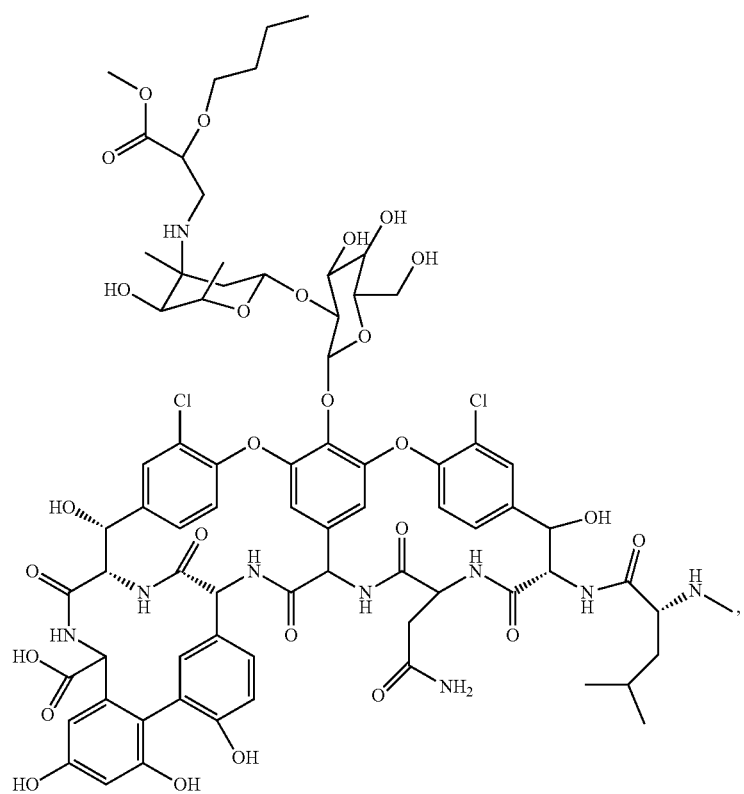

-continued
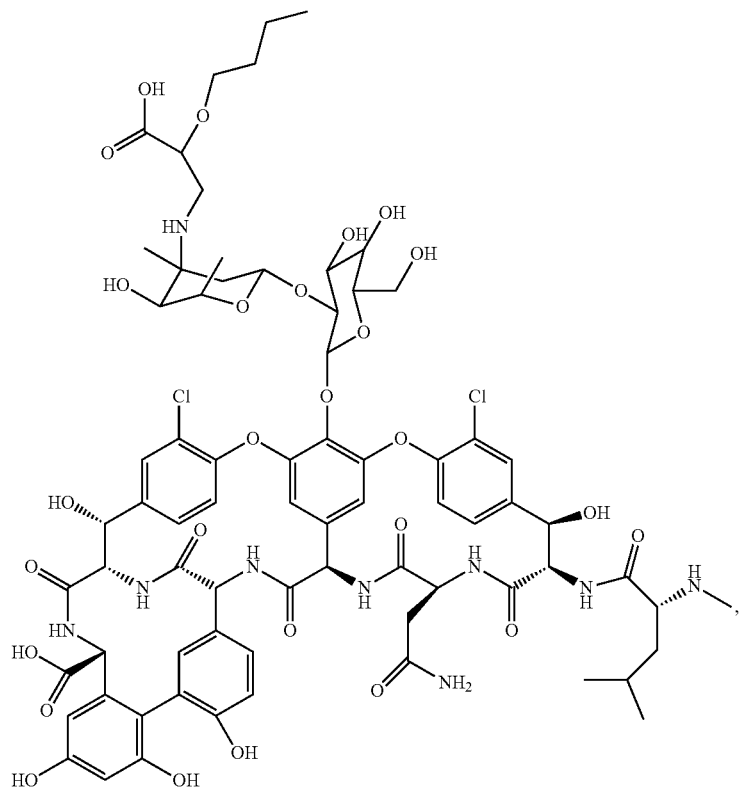
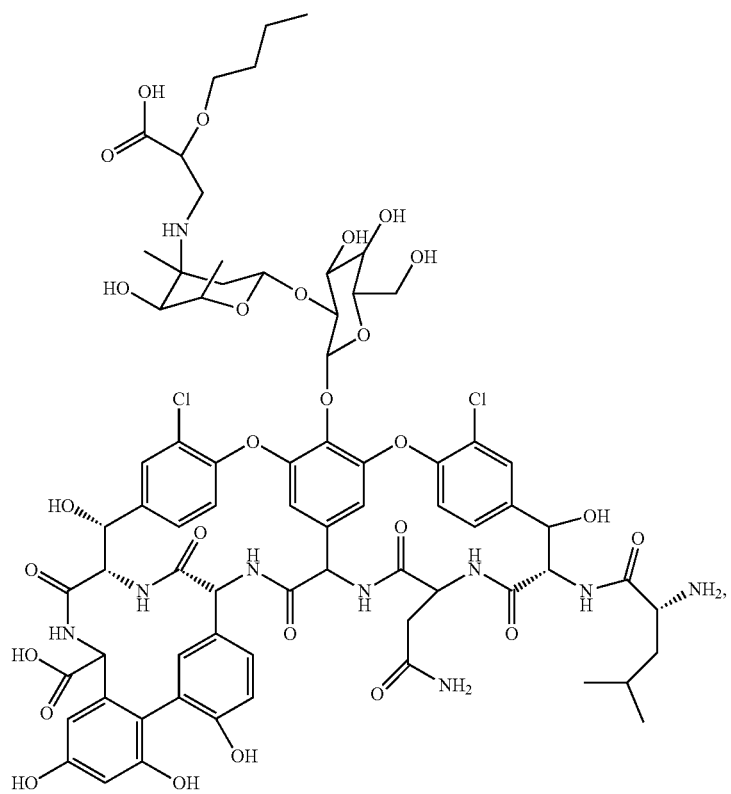

-continued
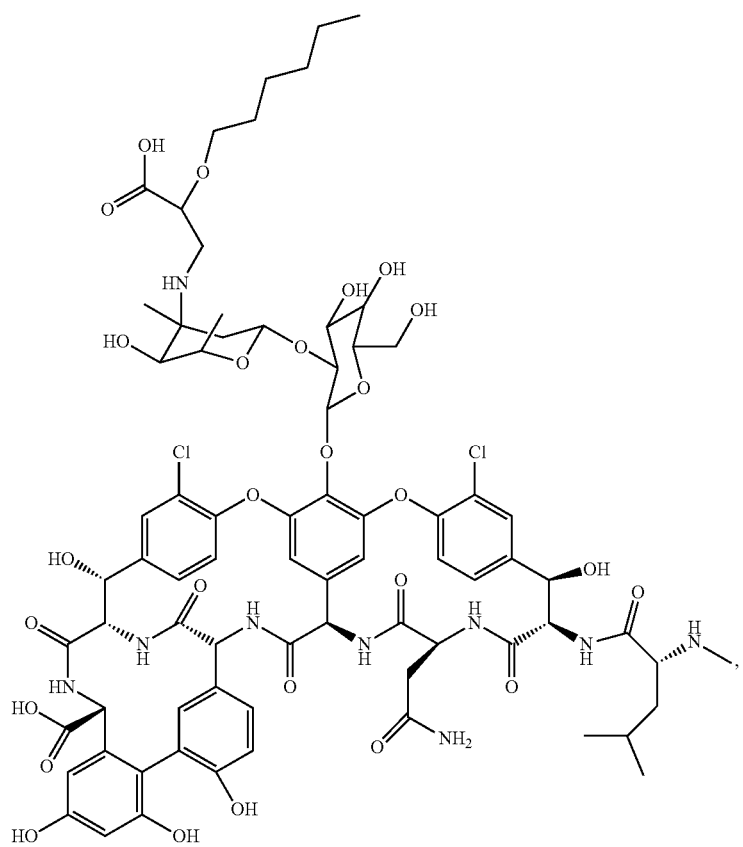
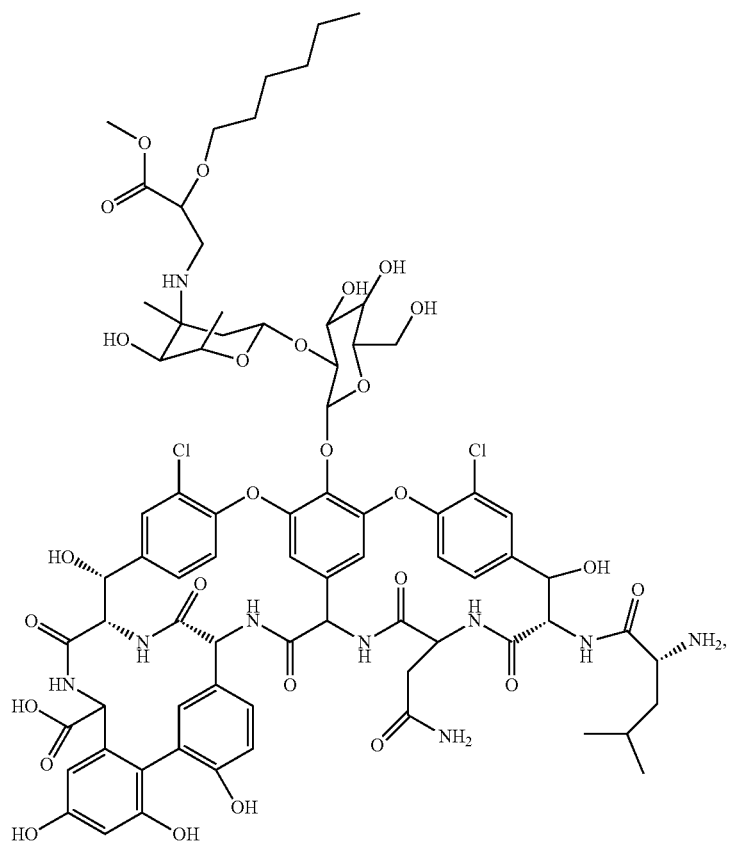

-continued
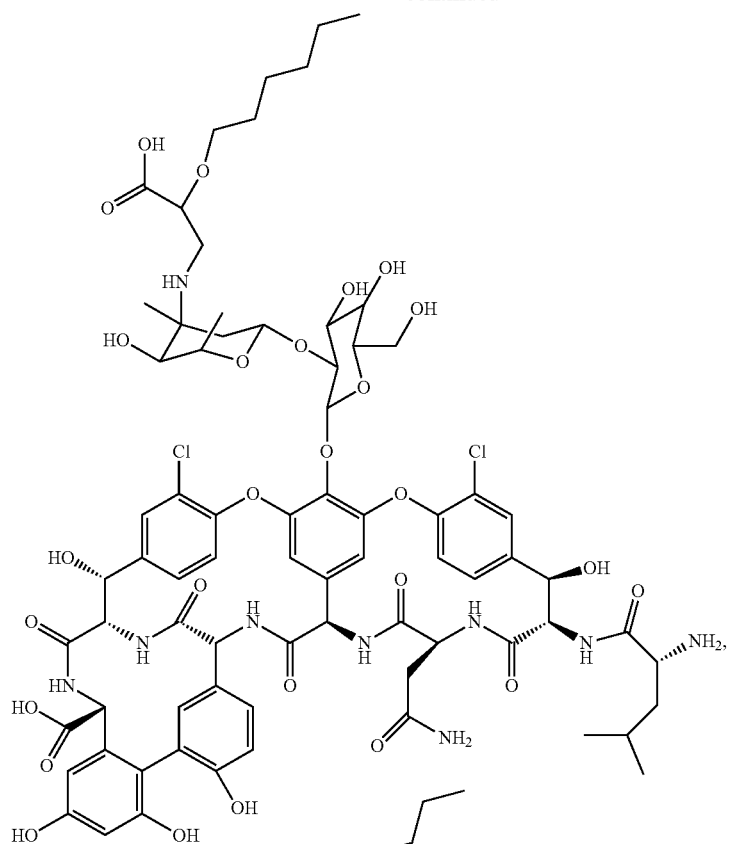
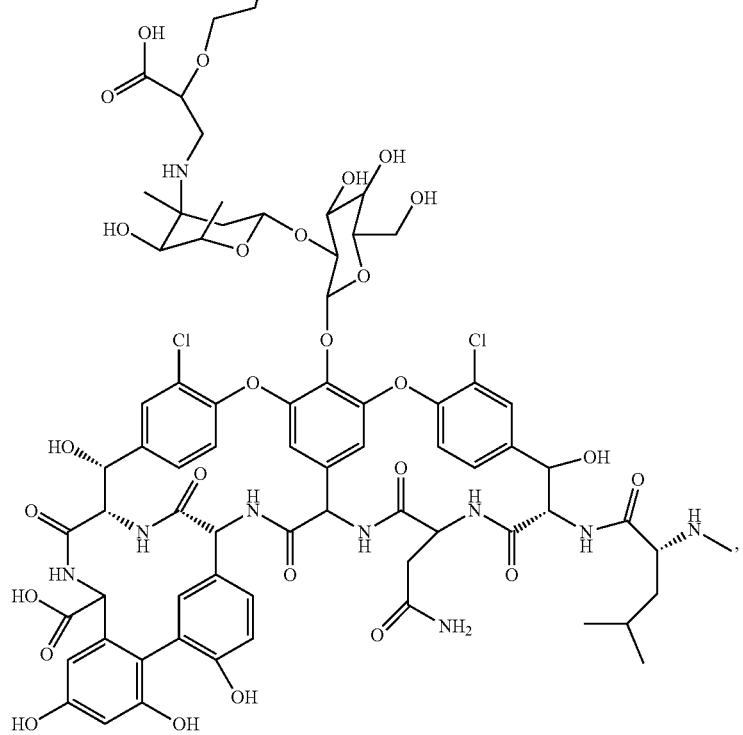

-continued
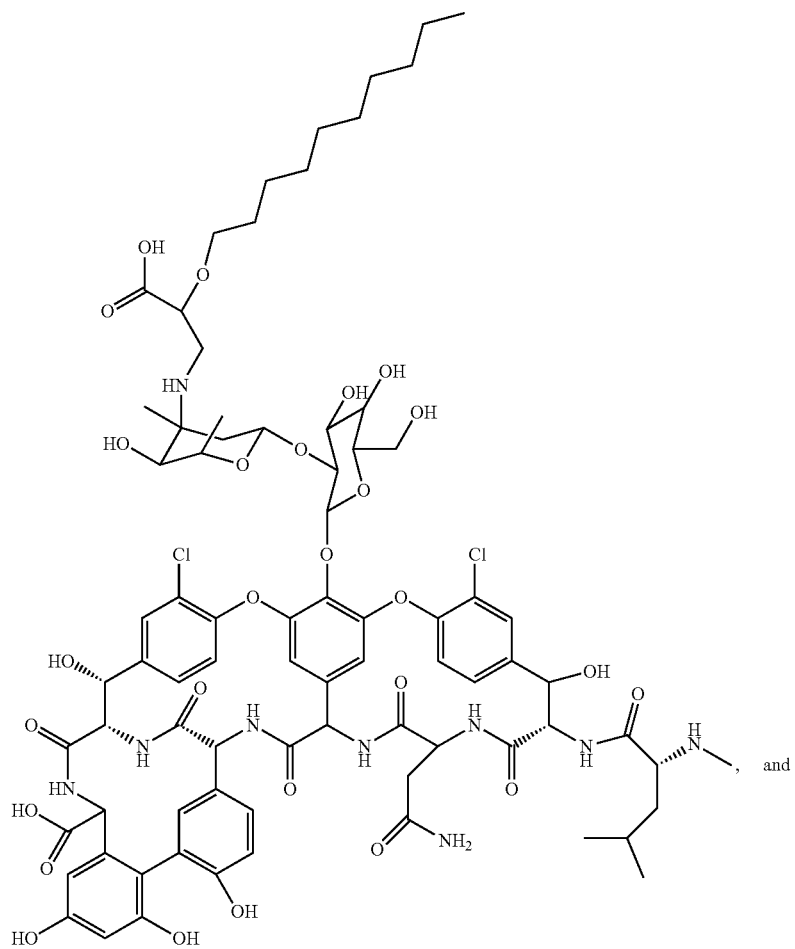
, and

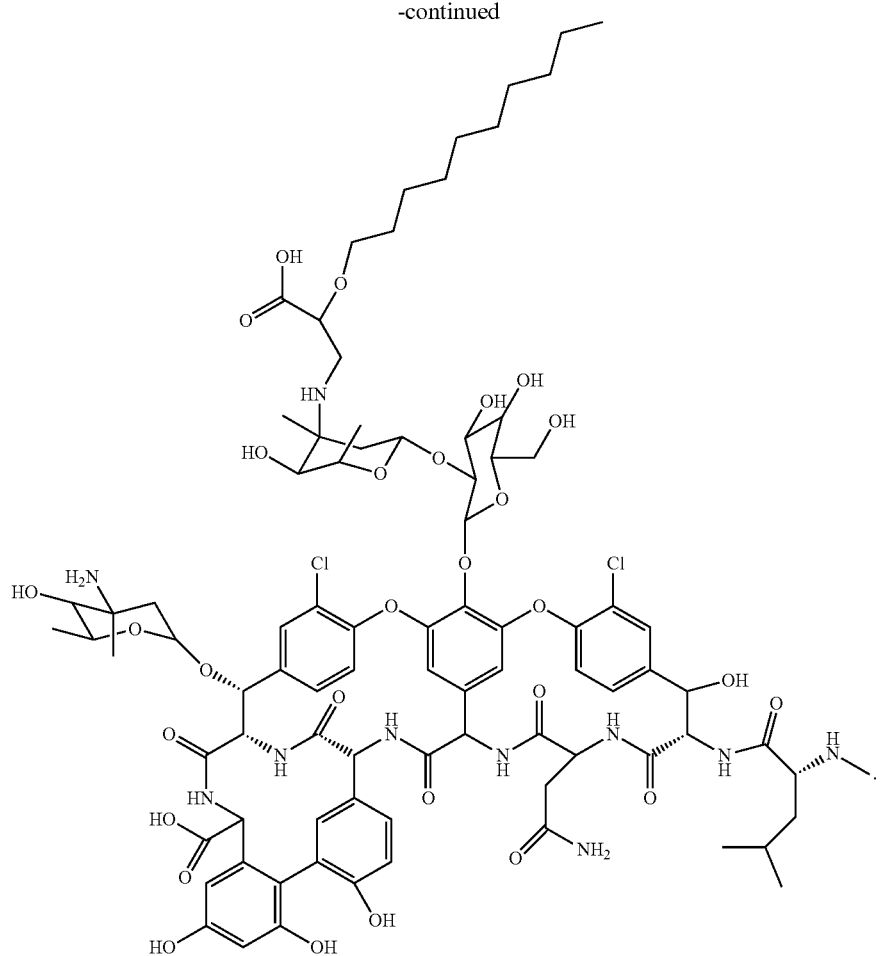

11. The vancomycin derivative of claim 1, wherein:
R$^1$ is —NHCH$_3$ or —NH$_2$;
R$^2$ is H or 4-epi-vancosaminyl;
R$^3$ is —(R)COOR$^a$ or —(S)COOR$^a$ or —(R/S)COOR$^a$; wherein R$^a$ is H, C1-C20 alkyl, C5-C12 aryl, C2-C12 alkenyl or C2-C12 alkynyl;
R$^4$ is hydrogen, C1-C20 alkyl, C5-C12 aryl, C2-C12 alkenyl, C2-C12 alkynyl, (C1-C20 alkyl)-R$^5$ or (C1-C20 alkyl)-O-R$^5$; and
R$^5$ has the following structure:

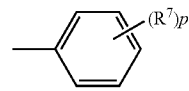

wherein, p is 1-5; and
each R$^7$ is independently:
(I) hydroxyl
(II) halogen
(III) nitro
(IV) amino or
(V) C1-C20 alkyl.

12. The process of claim 7, wherein R$^5$ has the following structure:

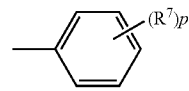

wherein p is 1-5; and
each R$^7$ is independently:
(I) hydroxyl
(II) halogen
(III) nitro
(IV) amino or
(V) C1-C20 alkyl.

* * * * *

UNITED STATES PATENT AND TRADEMARK OFFICE
CERTIFICATE OF CORRECTION

PATENT NO. : 9,828,413 B2  
APPLICATION NO. : 14/912573  
DATED : November 28, 2017  
INVENTOR(S) : Min Ge Page 1 of 3

It is certified that error appears in the above-identified patent and that said Letters Patent is hereby corrected as shown below:

In the Claims

Column 91, Lines 56-57, Claim 7, please delete "or -C(A2)2-N- or -C(A2)2-C(A2)2-C(A2)2-C(A2)2-," and insert -- or -C(A2)2-C(A2)2-C(A2)2-C(A2)2-, --;

Column 105, Claim 10, Top Structure, please delete the following structure:

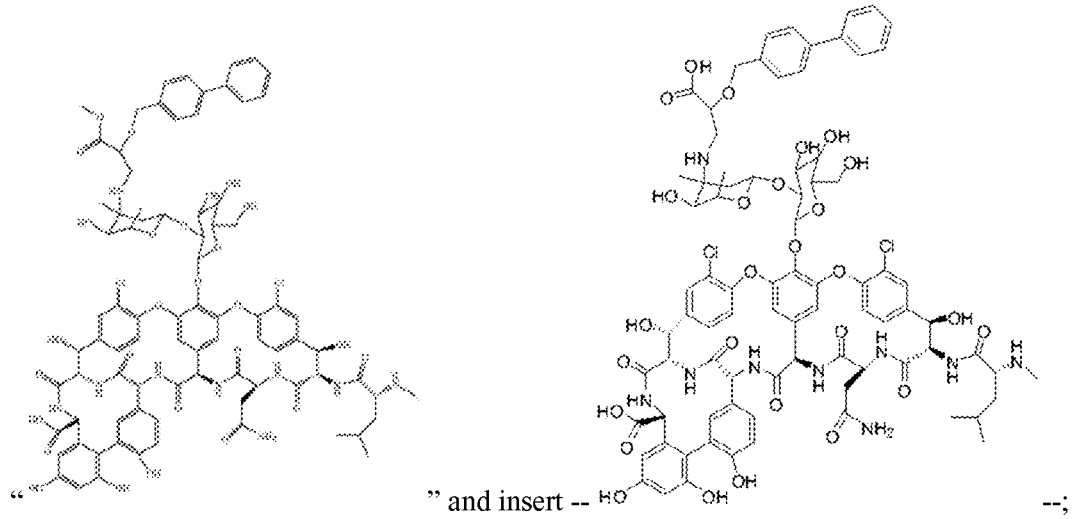

" and insert --             --;

Signed and Sealed this  
Tenth Day of July, 2018

Andrei Iancu  
*Director of the United States Patent and Trademark Office*

CERTIFICATE OF CORRECTION (continued)
U.S. Pat. No. 9,828,413 B2

Column 105, Claim 10, Bottom Structure, please delete the following structure:

" 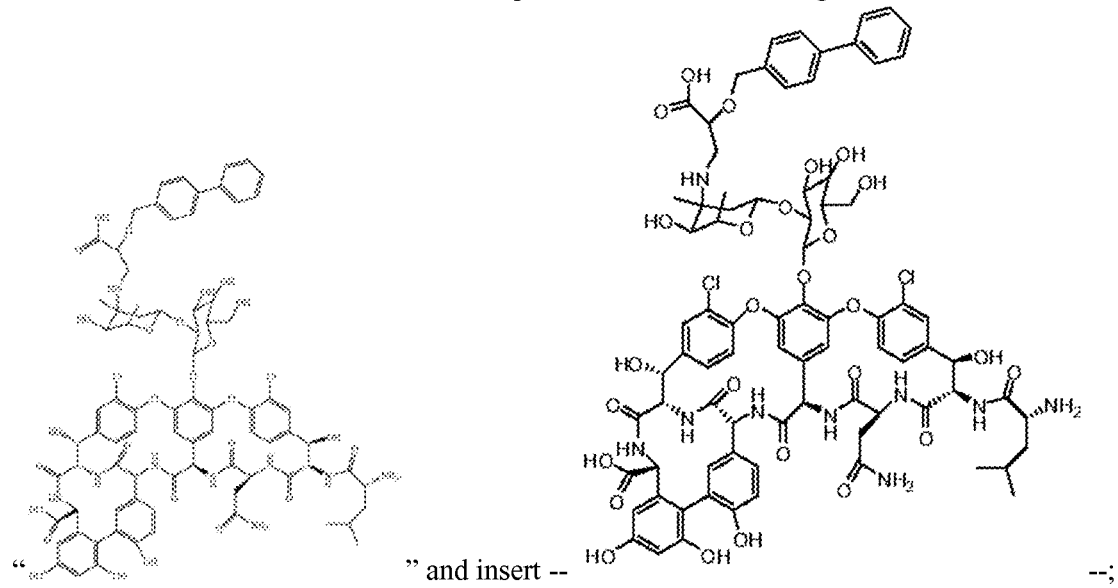 " and insert -- --;

Column 111, Claim 10, Bottom Structure, please delete the following structure:

" 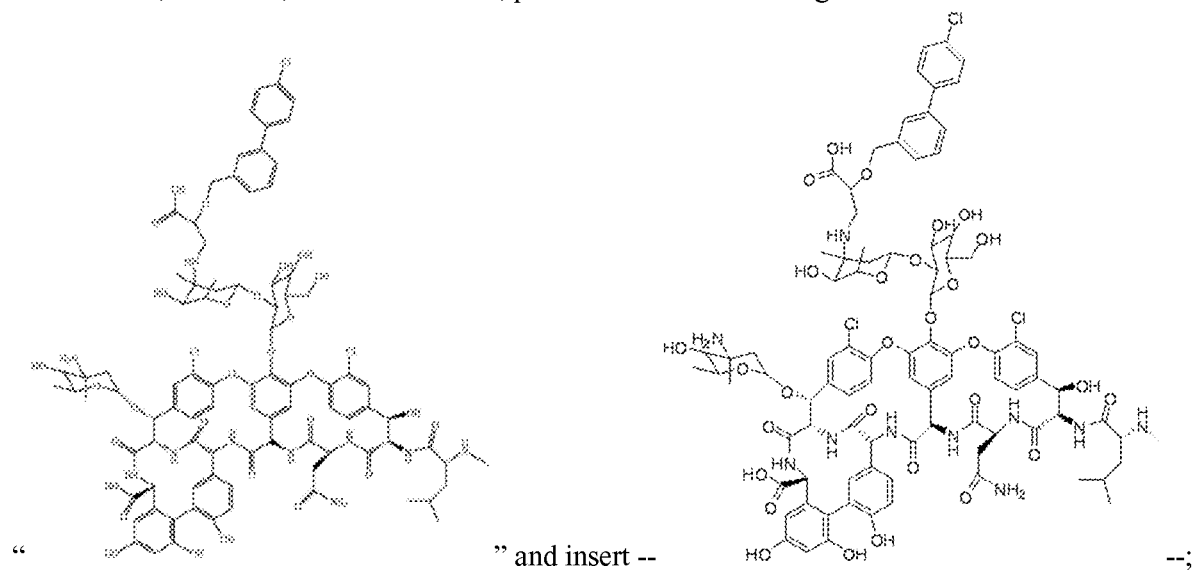 " and insert -- --;

CERTIFICATE OF CORRECTION (continued)  Page 3 of 3
U.S. Pat. No. 9,828,413 B2

Column 127, Claim 10, please delete the following structure:

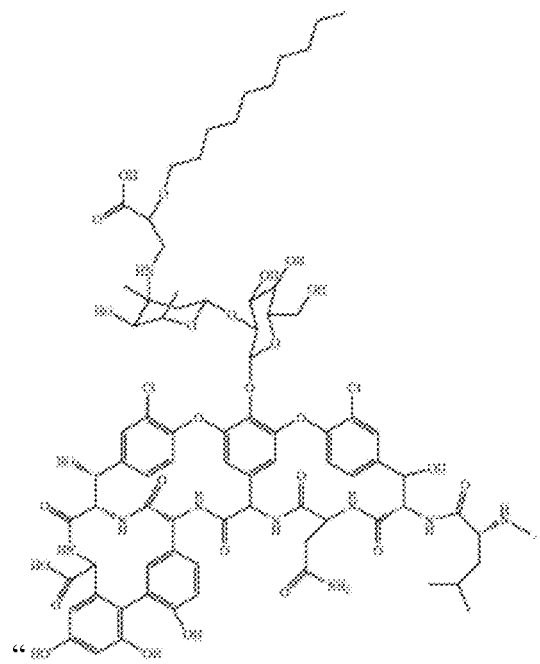

" and insert

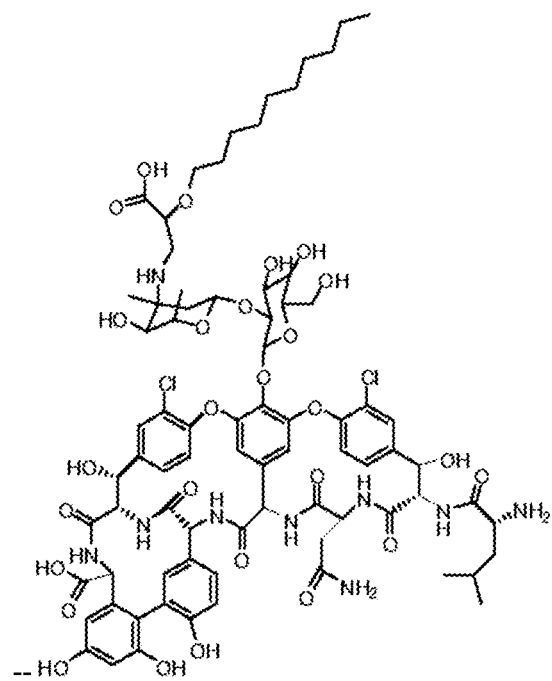

-- therefor.